US011065116B2

(12) United States Patent
Tegels

(10) Patent No.: US 11,065,116 B2
(45) Date of Patent: Jul. 20, 2021

(54) APPARATUS AND METHODS FOR TRANS-SEPTAL RETRIEVAL OF PROSTHETIC HEART VALVES

(71) Applicant: Tendyne Holdings, Inc., St. Paul, MN (US)

(72) Inventor: Zachary J. Tegels, Minneapolis, MN (US)

(73) Assignee: Tendyne Holdings, Inc., St. Paul, MN (US)

( * ) Notice: Subject to any disclaimer, the term of this patent is extended or adjusted under 35 U.S.C. 154(b) by 380 days.

(21) Appl. No.: 16/316,102

(22) PCT Filed: Jul. 11, 2017

(86) PCT No.: PCT/US2017/041454
§ 371 (c)(1),
(2) Date: Jan. 8, 2019

(87) PCT Pub. No.: WO2018/013515
PCT Pub. Date: Jan. 18, 2018

(65) Prior Publication Data
US 2020/0121457 A1    Apr. 23, 2020

Related U.S. Application Data

(60) Provisional application No. 62/361,228, filed on Jul. 12, 2016.

(51) Int. Cl.
*A61F 2/24* (2006.01)
*A61F 2/95* (2013.01)

(52) U.S. Cl.
CPC .......... *A61F 2/2427* (2013.01); *A61F 2/2418* (2013.01); *A61F 2002/9511* (2013.01);
(Continued)

(58) Field of Classification Search
CPC ...... A61F 2/2427; A61F 2/243; A61F 2/2439; A61F 2/2436; A61F 2/011; A61B 17/32056; A61B 2017/00358
See application file for complete search history.

(56) References Cited

U.S. PATENT DOCUMENTS 2,697,008 A    12/1954 Ross
3,409,013 A    11/1968 Berry
(Continued)

FOREIGN PATENT DOCUMENTS

CN    1486161 A    3/2004
CN    1961845 A    5/2007
(Continued)

OTHER PUBLICATIONS

US 9,155,620 B2, 10/2015, Gross et al. (withdrawn)
(Continued)

*Primary Examiner* — Wade Miles
(74) *Attorney, Agent, or Firm* — Lerner, David, Littenberg, Krumholz & Mentlik, LLP

(57) ABSTRACT

In some embodiments, a method for transfemoral retrieval and/or repositioning of a prosthetic valve (400) implanted within a heart includes inserting a retrieval assembly through a femoral vein and into a heart until a distal end portion of the retrieval assembly is disposed in an atrium of the heart. The prosthetic valve is formed with a shape-memory material. The retrieval assembly (402) includes an outer catheter (403), a middle catheter (404), a snare catheter (406), and a snare member (415). The snare member is moved distally out of a lumen of the snare catheter and into engagement with an inner frame (440) of the prosthetic valve. The retrieval assembly can invert an outer frame (410) of the prosthetic valve to collapse and retract the valve into a lumen of the retrieval assembly. In some embodiments, a positioning catheter (419) can be inserted through (Continued)

the apex of the heart to assist in positioning and inverting the prosthetic valve.

16 Claims, 29 Drawing Sheets

(52) U.S. Cl.
CPC .............. *A61F 2002/9534* (2013.01); *A61F 2210/0014* (2013.01)

(56) References Cited

U.S. PATENT DOCUMENTS

| | | |
|---|---|---|
| 3,472,230 A | 10/1969 | Fogarty et al. |
| 3,476,101 A | 11/1969 | Ross |
| 3,548,417 A | 12/1970 | Kischer |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,976,079 A | 8/1976 | Samuels et al. |
| 4,003,382 A | 1/1977 | Dyke |
| 4,035,849 A | 7/1977 | Angell et al. |
| 4,056,854 A | 11/1977 | Boretos et al. |
| 4,073,438 A | 2/1978 | Meyer |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,490,859 A | 1/1985 | Black et al. |
| 4,535,483 A | 8/1985 | Klawitter et al. |
| 4,574,803 A | 3/1986 | Storz |
| 4,585,705 A | 4/1986 | Broderick et al. |
| 4,592,340 A | 6/1986 | Boyles |
| 4,605,407 A | 8/1986 | Black et al. |
| 4,612,011 A | 9/1986 | Kautzky |
| 4,626,255 A | 12/1986 | Reichart et al. |
| 4,638,886 A | 1/1987 | Marietta |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,824,180 A | 4/1989 | Levrai |
| 4,829,990 A | 5/1989 | Thuroff et al. |
| 4,830,117 A | 5/1989 | Capasso |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,923,013 A | 5/1990 | De Gennaro |
| 4,960,424 A | 10/1990 | Grooters |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 4,996,873 A | 3/1991 | Takeuchi |
| 5,007,896 A | 4/1991 | Shiber |
| 5,026,366 A | 6/1991 | Leckrone |
| 5,032,128 A | 7/1991 | Alonso |
| 5,035,706 A | 7/1991 | Giantureo et al. |
| 5,037,434 A | 8/1991 | Lane |
| 5,047,041 A | 9/1991 | Samuels |
| 5,059,177 A | 10/1991 | Towne et al. |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,201,880 A | 4/1993 | Wright et al. |
| 5,266,073 A | 11/1993 | Wall |
| 5,282,847 A | 2/1994 | Trescony et al. |
| 5,295,958 A | 3/1994 | Shturman |
| 5,306,296 A | 4/1994 | Wright et al. |
| 5,332,402 A | 7/1994 | Teitelbaum |
| 5,336,616 A | 8/1994 | Livesey et al. |
| 5,344,442 A | 9/1994 | Deac |
| 5,360,444 A | 11/1994 | Kusuhara |
| 5,364,407 A | 11/1994 | Poll |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,415,667 A | 5/1995 | Frater |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,184 A | 9/1996 | Machiraju |
| 5,554,185 A | 9/1996 | Block et al. |
| 5,571,175 A | 11/1996 | Vanney et al. |
| 5,591,185 A | 1/1997 | Kilmer et al. |
| 5,607,462 A | 3/1997 | Imran |
| 5,607,464 A | 3/1997 | Trescony et al. |
| 5,609,626 A | 3/1997 | Quijano et al. |
| 5,639,274 A | 6/1997 | Fischell et al. |
| 5,662,704 A | 9/1997 | Gross |
| 5,665,115 A | 9/1997 | Cragg |
| 5,674,279 A | 10/1997 | Wright et al. |
| 5,697,905 A | 12/1997 | d'Ambrosio |
| 5,702,368 A | 12/1997 | Stevens et al. |
| 5,716,417 A | 2/1998 | Girard et al. |
| 5,728,068 A | 3/1998 | Leone et al. |
| 5,728,151 A | 3/1998 | Garrison et al. |
| 5,735,842 A | 4/1998 | Krueger et al. |
| 5,741,333 A | 4/1998 | Frid |
| 5,749,890 A | 5/1998 | Shaknovich |
| 5,756,476 A | 5/1998 | Epstein et al. |
| 5,769,812 A | 6/1998 | Stevens et al. |
| 5,792,179 A | 8/1998 | Sideris |
| 5,800,508 A | 9/1998 | Goicoechea et al. |
| 5,833,673 A | 11/1998 | Ockuly et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,904,697 A | 5/1999 | Gifford, III et al. |
| 5,925,063 A | 7/1999 | Khosravi |
| 5,957,949 A | 9/1999 | Leonhardt et al. |
| 5,968,052 A | 10/1999 | Sullivan, III et al. |
| 5,968,068 A | 10/1999 | Dehdashtian et al. |
| 5,972,030 A | 10/1999 | Garrison et al. |
| 5,993,481 A | 11/1999 | Marcade et al. |
| 6,027,525 A | 2/2000 | Suh et al. |
| 6,042,607 A | 3/2000 | Williamson, IV et al. |
| 6,045,497 A | 4/2000 | Schweich, Jr. et al. |
| 6,063,112 A | 5/2000 | Sgro |
| 6,077,214 A | 6/2000 | Mortier et al. |
| 6,099,508 A | 8/2000 | Bousquet |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,183,411 B1 | 2/2001 | Mortier et al. |
| 6,210,408 B1 | 4/2001 | Chandrasekaran et al. |

(56) References Cited

U.S. PATENT DOCUMENTS

| | | |
|---|---|---|
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,287,339 B1 | 9/2001 | Vazquez et al. |
| 6,299,637 B1 | 10/2001 | Shaolian et al. |
| 6,302,906 B1 | 10/2001 | Goicoechea et al. |
| 6,312,465 B1 | 11/2001 | Griffin et al. |
| 6,332,893 B1 | 12/2001 | Mortier et al. |
| 6,350,277 B1 | 2/2002 | Kocur |
| 6,358,277 B1 | 3/2002 | Duran |
| 6,379,372 B1 | 4/2002 | Dehdashtian et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,537,198 B1 | 3/2003 | Vidlund et al. |
| 6,540,782 B1 | 4/2003 | Snyders |
| 6,569,196 B1 | 5/2003 | Vesely |
| 6,575,252 B2 | 6/2003 | Reed |
| 6,582,462 B1 | 6/2003 | Andersen et al. |
| 6,605,112 B1 | 8/2003 | Moll et al. |
| 6,616,684 B1 | 9/2003 | Vidlund et al. |
| 6,622,730 B2 | 9/2003 | Ekvall et al. |
| 6,629,534 B1 | 10/2003 | St. Goar et al. |
| 6,629,921 B1 | 10/2003 | Schweich, Jr. et al. |
| 6,648,077 B2 | 11/2003 | Hoffman |
| 6,648,921 B2 | 11/2003 | Anderson et al. |
| 6,652,578 B2 | 11/2003 | Bailey et al. |
| 6,669,724 B2 | 12/2003 | Park et al. |
| 6,706,065 B2 | 3/2004 | Langberg et al. |
| 6,709,456 B2 | 3/2004 | Langberg et al. |
| 6,723,038 B1 | 4/2004 | Schroeder et al. |
| 6,726,715 B2 | 4/2004 | Sutherland |
| 6,730,118 B2 | 5/2004 | Spenser et al. |
| 6,733,525 B2 | 5/2004 | Yang et al. |
| 6,740,105 B2 | 5/2004 | Yodfat et al. |
| 6,746,401 B2 | 6/2004 | Panescu |
| 6,746,471 B2 | 6/2004 | Mortier et al. |
| 6,752,813 B2 | 6/2004 | Goldfarb et al. |
| 6,764,510 B2 | 7/2004 | Vidlund et al. |
| 6,797,002 B2 | 9/2004 | Spence et al. |
| 6,810,882 B2 | 11/2004 | Langberg et al. |
| 6,830,584 B1 | 12/2004 | Seguin |
| 6,854,668 B2 | 2/2005 | Wancho et al. |
| 6,855,144 B2 | 2/2005 | Lesh |
| 6,858,001 B1 | 2/2005 | Aboul-Hosn |
| 6,890,353 B2 | 5/2005 | Cohn et al. |
| 6,893,460 B2 | 5/2005 | Spenser et al. |
| 6,896,690 B1 | 5/2005 | Lambrecht et al. |
| 6,908,424 B2 | 6/2005 | Mortier et al. |
| 6,908,481 B2 | 6/2005 | Cribier |
| 6,936,067 B2 | 8/2005 | Buchanan |
| 6,945,996 B2 | 9/2005 | Sedransk |
| 6,955,175 B2 | 10/2005 | Stevens et al. |
| 6,974,476 B2 | 12/2005 | McGuckin, Jr. et al. |
| 6,976,543 B1 | 12/2005 | Fischer |
| 6,997,950 B2 | 2/2006 | Chawla |
| 7,018,406 B2 | 3/2006 | Seguin et al. |
| 7,018,408 B2 | 3/2006 | Bailey et al. |
| 7,044,905 B2 | 5/2006 | Vidlund et al. |
| 7,060,021 B1 | 6/2006 | Wilk |
| 7,077,862 B2 | 7/2006 | Vidlund et al. |
| 7,087,064 B1 | 8/2006 | Hyde |
| 7,100,614 B2 | 9/2006 | Stevens et al. |
| 7,101,395 B2 | 9/2006 | Tremulis et al. |
| 7,108,717 B2 | 9/2006 | Freidberg |
| 7,112,219 B2 | 9/2006 | Vidlund et al. |
| 7,115,141 B2 | 10/2006 | Menz et al. |
| 7,141,064 B2 | 11/2006 | Scott et al. |
| 7,175,656 B2 | 2/2007 | Khairkhahan |
| 7,198,646 B2 | 4/2007 | Figulla et al. |
| 7,201,772 B2 | 4/2007 | Schwammenthal et al. |
| 7,247,134 B2 | 7/2007 | Vidlund et al. |
| 7,252,682 B2 | 8/2007 | Seguin |
| 7,267,686 B2 | 9/2007 | DiMatteo et al. |
| 7,275,604 B1 | 10/2007 | Wall |
| 7,276,078 B2 | 10/2007 | Spenser et al. |
| 7,276,084 B2 | 10/2007 | Yang et al. |
| 7,316,706 B2 | 1/2008 | Bloom et al. |
| 7,318,278 B2 | 1/2008 | Zhang et al. |
| 7,326,236 B2 | 2/2008 | Andreas et al. |
| 7,329,278 B2 | 2/2008 | Seguin et al. |
| 7,331,991 B2 | 2/2008 | Kheradvar et al. |
| 7,335,213 B1 | 2/2008 | Hyde et al. |
| 7,374,571 B2 | 5/2008 | Pease et al. |
| 7,377,941 B2 | 5/2008 | Rhee et al. |
| 7,381,210 B2 | 6/2008 | Zarbatany et al. |
| 7,381,218 B2 | 6/2008 | Schreck |
| 7,393,360 B2 | 7/2008 | Spenser et al. |
| 7,404,824 B1 | 7/2008 | Webler et al. |
| 7,416,554 B2 | 8/2008 | Lam et al. |
| 7,422,072 B2 | 9/2008 | Dade |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,470,285 B2 | 12/2008 | Nugent et al. |
| 7,500,989 B2 | 3/2009 | Solem et al. |
| 7,503,931 B2 | 3/2009 | Kowalsky et al. |
| 7,510,572 B2 | 3/2009 | Gabbay |
| 7,510,575 B2 | 3/2009 | Spenser et al. |
| 7,513,908 B2 | 4/2009 | Lattouf |
| 7,524,330 B2 | 4/2009 | Berreklouw |
| 7,527,647 B2 | 5/2009 | Spence |
| 7,534,260 B2 | 5/2009 | Lattouf |
| 7,556,646 B2 | 7/2009 | Yang et al. |
| 7,579,381 B2 | 8/2009 | Dove |
| 7,585,321 B2 | 9/2009 | Cribier |
| 7,591,847 B2 | 9/2009 | Navia et al. |
| 7,618,446 B2 | 11/2009 | Andersen et al. |
| 7,618,447 B2 | 11/2009 | Case et al. |
| 7,621,948 B2 | 11/2009 | Herrmann et al. |
| 7,632,304 B2 | 12/2009 | Park |
| 7,632,308 B2 | 12/2009 | Loulmet |
| 7,635,386 B1 | 12/2009 | Gammie |
| 7,674,222 B2 | 3/2010 | Nikolic et al. |
| 7,674,286 B2 | 3/2010 | Alfieri et al. |
| 7,695,510 B2 | 4/2010 | Bloom et al. |
| 7,708,775 B2 | 5/2010 | Rowe et al. |
| 7,748,389 B2 | 7/2010 | Salahieh et al. |
| 7,766,961 B2 | 8/2010 | Patel et al. |
| 7,789,909 B2 | 9/2010 | Andersen et al. |
| 7,803,168 B2 | 9/2010 | Gifford et al. |
| 7,803,184 B2 | 9/2010 | McGuckin, Jr. et al. |
| 7,803,185 B2 | 9/2010 | Gabbay |
| 7,806,928 B2 | 10/2010 | Rowe et al. |
| 7,837,727 B2 | 11/2010 | Goetz et al. |
| 7,854,762 B2 | 12/2010 | Speziali et al. |
| 7,892,281 B2 | 2/2011 | Seguin et al. |
| 7,896,915 B2 | 3/2011 | Guyenot et al. |
| 7,901,454 B2 | 3/2011 | Kapadia et al. |
| 7,927,370 B2 | 4/2011 | Webler et al. |
| 7,931,630 B2 | 4/2011 | Nishtala et al. |
| 7,942,928 B2 | 5/2011 | Webler et al. |
| 7,955,247 B2 | 6/2011 | Levine et al. |
| 7,955,385 B2 | 6/2011 | Crittenden |
| 7,972,378 B2 | 7/2011 | Tabor et al. |
| 7,988,727 B2 | 8/2011 | Santamore et al. |
| 7,993,394 B2 | 8/2011 | Hariton et al. |
| 8,007,992 B2 | 8/2011 | Tian et al. |
| 8,029,556 B2 | 10/2011 | Rowe |
| 8,043,368 B2 | 10/2011 | Crabtree |

(56) References Cited

U.S. PATENT DOCUMENTS

| | | |
|---|---|---|
| 8,052,749 B2 | 11/2011 | Salahieh et al. |
| 8,052,750 B2 | 11/2011 | Tuval et al. |
| 8,052,751 B2 | 11/2011 | Aklog et al. |
| 8,062,355 B2 | 11/2011 | Figulla et al. |
| 8,062,359 B2 | 11/2011 | Marquez et al. |
| 8,070,802 B2 | 12/2011 | Lamphere et al. |
| 8,109,996 B2 | 2/2012 | Stacchino et al. |
| 8,142,495 B2 | 3/2012 | Hasenkam et al. |
| 8,152,821 B2 | 4/2012 | Gambale et al. |
| 8,157,810 B2 | 4/2012 | Case et al. |
| 8,167,932 B2 | 5/2012 | Bourang et al. |
| 8,167,934 B2 | 5/2012 | Styrc et al. |
| 8,187,299 B2 | 5/2012 | Goldfarb et al. |
| 8,206,439 B2 | 6/2012 | Gomez Duran |
| 8,216,301 B2 | 7/2012 | Bonhoeffer et al. |
| 8,226,711 B2 | 7/2012 | Mortier et al. |
| 8,236,045 B2 | 8/2012 | Benichou et al. |
| 8,241,274 B2 | 8/2012 | Keogh et al. |
| 8,252,051 B2 | 8/2012 | Chau et al. |
| 8,303,653 B2 | 11/2012 | Bonhoeffer et al. |
| 8,308,796 B2 | 11/2012 | Lashinski et al. |
| 8,323,334 B2 | 12/2012 | Deem et al. |
| 8,353,955 B2 | 1/2013 | Styrc et al. |
| RE44,075 E | 3/2013 | Williamson et al. |
| 8,449,599 B2 | 5/2013 | Chau et al. |
| 8,454,656 B2 | 6/2013 | Tuval |
| 8,470,028 B2 | 6/2013 | Thornton et al. |
| 8,480,730 B2 | 7/2013 | Maurer et al. |
| 8,486,138 B2 | 7/2013 | Vesely |
| 8,506,623 B2 | 8/2013 | Wilson et al. |
| 8,506,624 B2 | 8/2013 | Vidlund et al. |
| 8,578,705 B2 | 11/2013 | Sindano et al. |
| 8,579,913 B2 | 11/2013 | Nielsen |
| 8,591,573 B2 | 11/2013 | Barone |
| 8,591,576 B2 | 11/2013 | Hasenkam et al. |
| 8,597,347 B2 | 12/2013 | Maurer et al. |
| 8,685,086 B2 | 4/2014 | Navia et al. |
| 8,790,394 B2 | 7/2014 | Miller et al. |
| 8,845,717 B2 | 9/2014 | Khairkhahan et al. |
| 8,888,843 B2 | 11/2014 | Khairkhahan et al. |
| 8,900,214 B2 | 12/2014 | Nance et al. |
| 8,900,295 B2 | 12/2014 | Migliazza et al. |
| 8,926,696 B2 | 1/2015 | Cabiri et al. |
| 8,932,342 B2 | 1/2015 | McHugo et al. |
| 8,932,348 B2 | 1/2015 | Solem et al. |
| 8,945,208 B2 | 2/2015 | Jimenez et al. |
| 8,956,407 B2 | 2/2015 | Macoviak et al. |
| 8,979,922 B2 | 3/2015 | Jayasinghe et al. |
| 8,986,376 B2 | 3/2015 | Solem |
| 9,011,522 B2 | 4/2015 | Annest |
| 9,023,099 B2 | 5/2015 | Duffy et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,039,759 B2 | 5/2015 | Alkhatib et al. |
| 9,078,645 B2 | 7/2015 | Conklin et al. |
| 9,078,749 B2 | 7/2015 | Lutter et al. |
| 9,084,676 B2 | 7/2015 | Chau et al. |
| 9,095,433 B2 | 8/2015 | Lutter et al. |
| 9,125,742 B2 | 9/2015 | Yoganathan et al. |
| 9,149,357 B2 | 10/2015 | Seguin |
| 9,161,837 B2 | 10/2015 | Kapadia |
| 9,168,137 B2 | 10/2015 | Subramanian et al. |
| 9,232,995 B2 | 1/2016 | Kovalsky et al. |
| 9,232,998 B2 | 1/2016 | Wilson et al. |
| 9,232,999 B2 | 1/2016 | Maurer et al. |
| 9,241,702 B2 | 1/2016 | Maisano et al. |
| 9,254,192 B2 | 2/2016 | Lutter et al. |
| 9,265,608 B2 | 2/2016 | Miller et al. |
| 9,289,295 B2 | 3/2016 | Aklog et al. |
| 9,289,297 B2 | 3/2016 | Wilson et al. |
| 9,345,573 B2 | 5/2016 | Nyuli et al. |
| 9,480,557 B2 | 11/2016 | Pellegrini et al. |
| 9,480,559 B2 | 11/2016 | Vidlund et al. |
| 9,526,611 B2 | 12/2016 | Tegels et al. |
| 9,597,181 B2 | 3/2017 | Christianson et al. |
| 9,610,159 B2 | 4/2017 | Christianson et al. |
| 9,675,454 B2 | 6/2017 | Vidlund et al. |
| 9,730,792 B2 | 8/2017 | Lutter et al. |
| 9,827,092 B2 | 11/2017 | Vidlund et al. |
| 9,833,315 B2 | 12/2017 | Vidlund et al. |
| 9,867,700 B2 | 1/2018 | Bakis et al. |
| 9,883,941 B2 | 2/2018 | Hastings et al. |
| 9,895,221 B2 | 2/2018 | Vidlund |
| 9,986,993 B2 | 6/2018 | Vidlund et al. |
| 10,327,894 B2 | 6/2019 | Vidlund et al. |
| 2001/0018611 A1 | 8/2001 | Solem et al. |
| 2001/0021872 A1 | 9/2001 | Bailey et al. |
| 2001/0025171 A1 | 9/2001 | Mortier et al. |
| 2002/0010427 A1 | 1/2002 | Scarfone et al. |
| 2002/0116054 A1 | 8/2002 | Lundell et al. |
| 2002/0139056 A1 | 10/2002 | Finnell |
| 2002/0151961 A1 | 10/2002 | Lashinski et al. |
| 2002/0161377 A1 | 10/2002 | Rabkin |
| 2002/0173842 A1 | 11/2002 | Buchanan |
| 2002/0183827 A1 | 12/2002 | Derus et al. |
| 2003/0010509 A1 | 1/2003 | Hoffman |
| 2003/0036698 A1 | 2/2003 | Kohler et al. |
| 2003/0050694 A1 | 3/2003 | Yang et al. |
| 2003/0078652 A1 | 4/2003 | Sutherland |
| 2003/0100939 A1 | 5/2003 | Yodfat et al. |
| 2003/0105519 A1 | 6/2003 | Fasol et al. |
| 2003/0105520 A1 | 6/2003 | Alferness et al. |
| 2003/0120340 A1 | 6/2003 | Liska et al. |
| 2003/0130731 A1 | 7/2003 | Vidlund et al. |
| 2003/0149476 A1 | 8/2003 | Damm et al. |
| 2003/0212454 A1 | 11/2003 | Scott et al. |
| 2004/0039436 A1 | 2/2004 | Spenser et al. |
| 2004/0049266 A1 | 3/2004 | Anduiza et al. |
| 2004/0064014 A1 | 4/2004 | Melvin et al. |
| 2004/0092858 A1 | 5/2004 | Wilson et al. |
| 2004/0093075 A1 | 5/2004 | Kuehne |
| 2004/0097865 A1 | 5/2004 | Anderson et al. |
| 2004/0127983 A1 | 7/2004 | Mortier et al. |
| 2004/0133263 A1 | 7/2004 | Dusbabek et al. |
| 2004/0147958 A1 | 7/2004 | Lam et al. |
| 2004/0152947 A1 | 8/2004 | Schroeder et al. |
| 2004/0162610 A1 | 8/2004 | Liska et al. |
| 2004/0163828 A1 | 8/2004 | Silverstein et al. |
| 2004/0181239 A1 | 9/2004 | Dorn et al. |
| 2004/0186565 A1 | 9/2004 | Schreck |
| 2004/0186566 A1 | 9/2004 | Hindrichs et al. |
| 2004/0260317 A1 | 12/2004 | Bloom et al. |
| 2004/0260389 A1 | 12/2004 | Case et al. |
| 2005/0004652 A1 | 1/2005 | van der Burg et al. |
| 2005/0004666 A1 | 1/2005 | Alfieri et al. |
| 2005/0075727 A1 | 4/2005 | Wheatley |
| 2005/0080402 A1 | 4/2005 | Santamore et al. |
| 2005/0085900 A1 | 4/2005 | Case et al. |
| 2005/0096498 A1 | 5/2005 | Houser et al. |
| 2005/0107661 A1 | 5/2005 | Lau et al. |
| 2005/0113798 A1 | 5/2005 | Slater et al. |
| 2005/0113810 A1 | 5/2005 | Houser et al. |
| 2005/0113811 A1 | 5/2005 | Houser et al. |
| 2005/0119519 A9 | 6/2005 | Girard et al. |
| 2005/0121206 A1 | 6/2005 | Dolan |
| 2005/0125012 A1 | 6/2005 | Houser et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0137698 A1 | 6/2005 | Salahieh et al. |
| 2005/0148815 A1 | 7/2005 | Mortier et al. |
| 2005/0177180 A1 | 8/2005 | Kaganov et al. |
| 2005/0197695 A1 | 9/2005 | Stacchino et al. |
| 2005/0203614 A1 | 9/2005 | Forster et al. |
| 2005/0203615 A1 | 9/2005 | Forster et al. |
| 2005/0203617 A1 | 9/2005 | Forster et al. |
| 2005/0234546 A1 | 10/2005 | Nugent et al. |
| 2005/0240200 A1 | 10/2005 | Bergheim |
| 2005/0251209 A1 | 11/2005 | Saadat et al. |
| 2005/0256567 A1 | 11/2005 | Lim et al. |
| 2005/0283231 A1 | 12/2005 | Haug et al. |
| 2005/0288766 A1 | 12/2005 | Plain et al. |
| 2006/0004442 A1 | 1/2006 | Spenser et al. |

(56) References Cited

U.S. PATENT DOCUMENTS

| | | |
|---|---|---|
| 2006/0025784 A1 | 2/2006 | Starksen et al. |
| 2006/0025857 A1 | 2/2006 | Bergheim et al. |
| 2006/0030885 A1 | 2/2006 | Hyde |
| 2006/0042803 A1 | 3/2006 | Gallaher |
| 2006/0047338 A1 | 3/2006 | Jenson et al. |
| 2006/0052868 A1 | 3/2006 | Mortier et al. |
| 2006/0058872 A1 | 3/2006 | Salahieh et al. |
| 2006/0094983 A1 | 5/2006 | Burbank et al. |
| 2006/0129025 A1 | 6/2006 | Levine et al. |
| 2006/0142784 A1 | 6/2006 | Kontos |
| 2006/0161040 A1 | 7/2006 | McCarthy et al. |
| 2006/0161249 A1 | 7/2006 | Realyvasquez et al. |
| 2006/0167541 A1 | 7/2006 | Lattouf |
| 2006/0195134 A1 | 8/2006 | Crittenden |
| 2006/0195183 A1 | 8/2006 | Navia et al. |
| 2006/0229708 A1 | 10/2006 | Powell et al. |
| 2006/0229719 A1 | 10/2006 | Marquez et al. |
| 2006/0241745 A1 | 10/2006 | Solem |
| 2006/0247491 A1 | 11/2006 | Vidlund et al. |
| 2006/0252984 A1 | 11/2006 | Randert et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0276874 A1 | 12/2006 | Wilson et al. |
| 2006/0282161 A1 | 12/2006 | Huynh et al. |
| 2006/0287716 A1 | 12/2006 | Banbury et al. |
| 2006/0287717 A1 | 12/2006 | Rowe et al. |
| 2007/0005131 A1 | 1/2007 | Taylor |
| 2007/0005231 A1 | 1/2007 | Seguchi |
| 2007/0010877 A1 | 1/2007 | Salahieh et al. |
| 2007/0016286 A1 | 1/2007 | Herrmann et al. |
| 2007/0016288 A1 | 1/2007 | Gurskis et al. |
| 2007/0027535 A1 | 2/2007 | Purdy et al. |
| 2007/0038291 A1 | 2/2007 | Case et al. |
| 2007/0050020 A1 | 3/2007 | Spence |
| 2007/0061010 A1 | 3/2007 | Hauser et al. |
| 2007/0066863 A1 | 3/2007 | Rafiee et al. |
| 2007/0073387 A1 | 3/2007 | Forster et al. |
| 2007/0078297 A1 | 4/2007 | Rafiee et al. |
| 2007/0083076 A1 | 4/2007 | Lichtenstein |
| 2007/0083259 A1 | 4/2007 | Bloom et al. |
| 2007/0093890 A1 | 4/2007 | Eliasen et al. |
| 2007/0100439 A1 | 5/2007 | Cangialosi et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0118210 A1 | 5/2007 | Pinchuk |
| 2007/0118213 A1 | 5/2007 | Loulmet |
| 2007/0142906 A1 | 6/2007 | Figulla et al. |
| 2007/0161846 A1 | 7/2007 | Nikolic et al. |
| 2007/0162048 A1 | 7/2007 | Quinn et al. |
| 2007/0162103 A1 | 7/2007 | Case et al. |
| 2007/0168024 A1 | 7/2007 | Khairkhahan |
| 2007/0185565 A1 | 8/2007 | Schwammenthal et al. |
| 2007/0185571 A1 | 8/2007 | Kapadia et al. |
| 2007/0203575 A1 | 8/2007 | Forster et al. |
| 2007/0213813 A1 | 9/2007 | Von Segesser et al. |
| 2007/0215362 A1 | 9/2007 | Rodgers |
| 2007/0221388 A1 | 9/2007 | Johnson |
| 2007/0233239 A1 | 10/2007 | Navia et al. |
| 2007/0239265 A1 | 10/2007 | Birdsall |
| 2007/0256843 A1 | 11/2007 | Pahila |
| 2007/0265658 A1 | 11/2007 | Nelson et al. |
| 2007/0267202 A1 | 11/2007 | Mariller |
| 2007/0270932 A1 | 11/2007 | Headley et al. |
| 2007/0270943 A1 | 11/2007 | Solem et al. |
| 2007/0293944 A1 | 12/2007 | Spenser et al. |
| 2008/0009940 A1 | 1/2008 | Cribier |
| 2008/0033543 A1 | 2/2008 | Gurskis et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0082163 A1 | 4/2008 | Woo |
| 2008/0082166 A1 | 4/2008 | Styrc et al. |
| 2008/0091264 A1 | 4/2008 | Machold et al. |
| 2008/0114442 A1 | 5/2008 | Mitchell et al. |
| 2008/0125861 A1 | 5/2008 | Webler et al. |
| 2008/0147179 A1 | 6/2008 | Cai et al. |
| 2008/0154355 A1 | 6/2008 | Benichou et al. |
| 2008/0154356 A1 | 6/2008 | Obermiller et al. |
| 2008/0161911 A1 | 7/2008 | Revuelta et al. |
| 2008/0172035 A1 | 7/2008 | Starksen et al. |
| 2008/0177381 A1 | 7/2008 | Navia et al. |
| 2008/0183203 A1 | 7/2008 | Fitzgerald et al. |
| 2008/0183273 A1 | 7/2008 | Mesana et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0243150 A1 | 10/2008 | Starksen et al. |
| 2008/0243245 A1 | 10/2008 | Thambar et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2008/0288060 A1 | 11/2008 | Kaye et al. |
| 2008/0293996 A1 | 11/2008 | Evans et al. |
| 2009/0005863 A1 | 1/2009 | Goetz et al. |
| 2009/0048668 A1 | 2/2009 | Wilson et al. |
| 2009/0054723 A1* | 2/2009 | Khairkhahan ..... A61B 17/0057 600/16 |
| 2009/0054968 A1 | 2/2009 | Bonhoeffer et al. |
| 2009/0054974 A1 | 2/2009 | McGuckin, Jr. et al. |
| 2009/0062908 A1 | 3/2009 | Bonhoeffer et al. |
| 2009/0076598 A1 | 3/2009 | Salahieh et al. |
| 2009/0082619 A1 | 3/2009 | De Marchena |
| 2009/0088836 A1 | 4/2009 | Bishop et al. |
| 2009/0099410 A1 | 4/2009 | De Marchena |
| 2009/0112309 A1 | 4/2009 | Jaramillo et al. |
| 2009/0131849 A1 | 5/2009 | Maurer et al. |
| 2009/0132035 A1 | 5/2009 | Roth et al. |
| 2009/0137861 A1 | 5/2009 | Goldberg et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0177266 A1 | 7/2009 | Powell et al. |
| 2009/0192601 A1 | 7/2009 | Rafiee et al. |
| 2009/0210052 A1 | 8/2009 | Forster et al. |
| 2009/0216322 A1 | 8/2009 | Le et al. |
| 2009/0222076 A1 | 9/2009 | Figulla et al. |
| 2009/0224529 A1 | 9/2009 | Gill |
| 2009/0234318 A1 | 9/2009 | Loulmet et al. |
| 2009/0234435 A1 | 9/2009 | Johnson et al. |
| 2009/0234443 A1 | 9/2009 | Ottma et al. |
| 2009/0240320 A1 | 9/2009 | Tuval et al. |
| 2009/0248149 A1 | 10/2009 | Gabbay |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0292262 A1 | 11/2009 | Adams et al. |
| 2009/0319037 A1 | 12/2009 | Rowe et al. |
| 2009/0326575 A1 | 12/2009 | Galdonik et al. |
| 2010/0016958 A1 | 1/2010 | St. Goar et al. |
| 2010/0021382 A1 | 1/2010 | Dorshow et al. |
| 2010/0023117 A1 | 1/2010 | Yoganathan et al. |
| 2010/0036479 A1 | 2/2010 | Hill et al. |
| 2010/0049313 A1 | 2/2010 | Alon et al. |
| 2010/0082094 A1 | 4/2010 | Quadri et al. |
| 2010/0161041 A1 | 6/2010 | Maisano et al. |
| 2010/0168839 A1 | 7/2010 | Braido et al. |
| 2010/0179641 A1 | 7/2010 | Ryan et al. |
| 2010/0185277 A1 | 7/2010 | Braido et al. |
| 2010/0185278 A1 | 7/2010 | Schankereli |
| 2010/0191326 A1 | 7/2010 | Alkhatib |
| 2010/0192402 A1 | 8/2010 | Yamaguchi et al. |
| 2010/0204781 A1 | 8/2010 | Alkhatib |
| 2010/0210899 A1 | 8/2010 | Schankereli |

(56) References Cited

U.S. PATENT DOCUMENTS

| | | |
|---|---|---|
| 2010/0217382 A1 | 8/2010 | Chau et al. |
| 2010/0249489 A1 | 9/2010 | Jarvik |
| 2010/0249923 A1 | 9/2010 | Alkhatib et al. |
| 2010/0280604 A1 | 11/2010 | Zipory et al. |
| 2010/0286768 A1 | 11/2010 | Alkhatib |
| 2010/0298755 A1 | 11/2010 | McNamara et al. |
| 2010/0298931 A1 | 11/2010 | Quadri et al. |
| 2011/0004296 A1 | 1/2011 | Lutter et al. |
| 2011/0015616 A1 | 1/2011 | Straubinger et al. |
| 2011/0015728 A1 | 1/2011 | Jimenez et al. |
| 2011/0015729 A1 | 1/2011 | Jimenez et al. |
| 2011/0029072 A1 | 2/2011 | Gabbay |
| 2011/0066231 A1 | 3/2011 | Cartledge et al. |
| 2011/0066233 A1 | 3/2011 | Thornton et al. |
| 2011/0112632 A1 | 5/2011 | Chau et al. |
| 2011/0137397 A1 | 6/2011 | Chau et al. |
| 2011/0137408 A1 | 6/2011 | Bergheim |
| 2011/0224655 A1 | 9/2011 | Asirvatham et al. |
| 2011/0224678 A1 | 9/2011 | Gabbay |
| 2011/0224728 A1 | 9/2011 | Martin et al. |
| 2011/0224784 A1 | 9/2011 | Quinn |
| 2011/0245911 A1 | 10/2011 | Quill et al. |
| 2011/0251682 A1 | 10/2011 | Murray, III et al. |
| 2011/0264191 A1 | 10/2011 | Rothstein |
| 2011/0264206 A1 | 10/2011 | Tabor |
| 2011/0288637 A1 | 11/2011 | De Marchena |
| 2011/0319988 A1 | 12/2011 | Schankereli et al. |
| 2011/0319989 A1 | 12/2011 | Lane et al. |
| 2012/0010694 A1 | 1/2012 | Lutter et al. |
| 2012/0016468 A1 | 1/2012 | Robin et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0053686 A1 | 3/2012 | McNamara et al. |
| 2012/0059487 A1 | 3/2012 | Cunanan et al. |
| 2012/0089171 A1 | 4/2012 | Hastings et al. |
| 2012/0101571 A1 | 4/2012 | Thambar et al. |
| 2012/0101572 A1 | 4/2012 | Kovalsky et al. |
| 2012/0116351 A1 | 5/2012 | Chomas et al. |
| 2012/0123529 A1 | 5/2012 | Levi et al. |
| 2012/0165930 A1 | 6/2012 | Gifford, III et al. |
| 2012/0179244 A1 | 7/2012 | Schankereli et al. |
| 2012/0203336 A1 | 8/2012 | Annest |
| 2012/0215303 A1 | 8/2012 | Quadri et al. |
| 2012/0226348 A1 | 9/2012 | Lane et al. |
| 2012/0283824 A1 | 11/2012 | Lutter et al. |
| 2012/0289945 A1 | 11/2012 | Segermark |
| 2013/0030522 A1 | 1/2013 | Rowe et al. |
| 2013/0053950 A1 | 2/2013 | Rowe et al. |
| 2013/0066341 A1 | 3/2013 | Ketai et al. |
| 2013/0079873 A1 | 3/2013 | Migliazza et al. |
| 2013/0131788 A1 | 5/2013 | Quadri et al. |
| 2013/0172978 A1 | 7/2013 | Vidlund et al. |
| 2013/0184811 A1 | 7/2013 | Rowe et al. |
| 2013/0190860 A1 | 7/2013 | Sundt, III |
| 2013/0190861 A1 | 7/2013 | Chau et al. |
| 2013/0197622 A1 | 8/2013 | Mitra et al. |
| 2013/0226288 A1 | 8/2013 | Goldwasser et al. |
| 2013/0231735 A1 | 9/2013 | Deem et al. |
| 2013/0274874 A1 | 10/2013 | Hammer |
| 2013/0282101 A1 | 10/2013 | Eidenschink et al. |
| 2013/0310928 A1 | 11/2013 | Morriss et al. |
| 2013/0317603 A1 | 11/2013 | McLean et al. |
| 2013/0325041 A1 | 12/2013 | Annest et al. |
| 2013/0325110 A1 | 12/2013 | Khalil et al. |
| 2013/0338752 A1 | 12/2013 | Geusen et al. |
| 2014/0046433 A1 | 2/2014 | Kovalsky |
| 2014/0081323 A1 | 3/2014 | Hawkins |
| 2014/0094918 A1 | 4/2014 | Vishnubholta et al. |
| 2014/0142691 A1 | 5/2014 | Pouletty |
| 2014/0163668 A1 | 6/2014 | Rafiee |
| 2014/0194981 A1 | 7/2014 | Menk et al. |
| 2014/0194983 A1 | 7/2014 | Kovalsky et al. |
| 2014/0214159 A1 | 7/2014 | Vidlund et al. |
| 2014/0222142 A1 | 8/2014 | Kovalsky et al. |
| 2014/0243966 A1 | 8/2014 | Garde et al. |
| 2014/0277419 A1 | 9/2014 | Garde et al. |
| 2014/0296969 A1 | 10/2014 | Tegels et al. |
| 2014/0296970 A1 | 10/2014 | Ekvall et al. |
| 2014/0296971 A1 | 10/2014 | Tegels et al. |
| 2014/0296972 A1 | 10/2014 | Tegels et al. |
| 2014/0296975 A1 | 10/2014 | Tegels et al. |
| 2014/0303718 A1 | 10/2014 | Tegels et al. |
| 2014/0309732 A1 | 10/2014 | Solem |
| 2014/0316516 A1 | 10/2014 | Vidlund et al. |
| 2014/0324160 A1 | 10/2014 | Benichou et al. |
| 2014/0324161 A1 | 10/2014 | Tegels et al. |
| 2014/0324164 A1 | 10/2014 | Gross et al. |
| 2014/0331475 A1 | 11/2014 | Duffy et al. |
| 2014/0358224 A1 | 12/2014 | Tegels et al. |
| 2014/0364942 A1 | 12/2014 | Straubinger et al. |
| 2014/0364944 A1 | 12/2014 | Lutter et al. |
| 2014/0379076 A1 | 12/2014 | Vidlund et al. |
| 2015/0005874 A1 | 1/2015 | Vidlund et al. |
| 2015/0011821 A1 | 1/2015 | Gorman et al. |
| 2015/0025553 A1 | 1/2015 | Del Nido et al. |
| 2015/0057705 A1 | 2/2015 | Vidlund |
| 2015/0073542 A1 | 3/2015 | Heldman |
| 2015/0073545 A1 | 3/2015 | Braido |
| 2015/0094802 A1 | 4/2015 | Buchbinder et al. |
| 2015/0105856 A1 | 4/2015 | Rowe et al. |
| 2015/0119936 A1 | 4/2015 | Gilmore et al. |
| 2015/0119978 A1 | 4/2015 | Tegels et al. |
| 2015/0127093 A1 | 5/2015 | Hosmer et al. |
| 2015/0127096 A1 | 5/2015 | Rowe et al. |
| 2015/0134050 A1 | 5/2015 | Solem et al. |
| 2015/0142100 A1 | 5/2015 | Morriss et al. |
| 2015/0142101 A1 | 5/2015 | Coleman et al. |
| 2015/0142103 A1 | 5/2015 | Vidlund |
| 2015/0142104 A1 | 5/2015 | Braido |
| 2015/0173897 A1 | 6/2015 | Raanani et al. |
| 2015/0196393 A1 | 7/2015 | Vidlund et al. |
| 2015/0196688 A1 | 7/2015 | James |
| 2015/0202044 A1 | 7/2015 | Chau et al. |
| 2015/0216653 A1 | 8/2015 | Freudenthal |
| 2015/0216660 A1 | 8/2015 | Pintor |
| 2015/0223820 A1 | 8/2015 | Olson |
| 2015/0223934 A1 | 8/2015 | Vidlund et al. |
| 2015/0238312 A1* | 8/2015 | Lashinski .............. A61F 2/2487 623/2.18 |
| 2015/0238729 A1 | 8/2015 | Jenson et al. |
| 2015/0272731 A1 | 10/2015 | Racchini et al. |
| 2015/0305860 A1 | 10/2015 | Wang et al. |
| 2015/0305864 A1 | 10/2015 | Quadri et al. |
| 2015/0305868 A1 | 10/2015 | Lutter et al. |
| 2015/0327995 A1 | 11/2015 | Morin et al. |
| 2015/0328001 A1 | 11/2015 | McLean |
| 2015/0335424 A1 | 11/2015 | McLean |
| 2015/0335429 A1 | 11/2015 | Morriss et al. |
| 2015/0342717 A1 | 12/2015 | O'Donnell et al. |
| 2015/0351903 A1 | 12/2015 | Morriss et al. |
| 2015/0351906 A1 | 12/2015 | Hammer et al. |
| 2016/0000562 A1 | 1/2016 | Siegel |
| 2016/0008131 A1 | 1/2016 | Christianson et al. |
| 2016/0067042 A1 | 3/2016 | Murad et al. |
| 2016/0074160 A1 | 3/2016 | Christianson et al. |
| 2016/0106537 A1 | 4/2016 | Christianson et al. |
| 2016/0113764 A1 | 4/2016 | Sheahan |
| 2016/0143736 A1 | 5/2016 | Vidlund |
| 2016/0151155 A1 | 6/2016 | Lutter et al. |
| 2016/0206280 A1 | 7/2016 | Vidlund et al. |
| 2016/0242902 A1 | 8/2016 | Morriss |
| 2016/0262879 A1 | 9/2016 | Meiri et al. |
| 2016/0262881 A1 | 9/2016 | Schankereli et al. |
| 2016/0278955 A1 | 9/2016 | Liu et al. |
| 2016/0317290 A1 | 11/2016 | Chau |
| 2016/0324635 A1 | 11/2016 | Vidlund et al. |
| 2016/0331527 A1 | 11/2016 | Vidlund et al. |
| 2016/0346086 A1 | 12/2016 | Solem |
| 2016/0367365 A1 | 12/2016 | Conklin |
| 2016/0367367 A1 | 12/2016 | Maisano et al. |
| 2016/0367368 A1 | 12/2016 | Vidlund et al. |
| 2017/0079790 A1* | 3/2017 | Vidlund .............. A61F 2/2418 |

(56) References Cited

U.S. PATENT DOCUMENTS

| | | | |
|---|---|---|---|
| 2017/0100248 A1 | 4/2017 | Tegels et al. | |
| 2017/0128208 A1 | 5/2017 | Christianson et al. | |
| 2017/0181835 A1* | 6/2017 | Kleshinski | A61F 2/013 |
| 2017/0181854 A1 | 6/2017 | Christianson et al. | |
| 2017/0196688 A1 | 7/2017 | Christianson et al. | |
| 2017/0252153 A1 | 9/2017 | Chau et al. | |
| 2017/0266001 A1 | 9/2017 | Vidlund et al. | |
| 2017/0281343 A1 | 10/2017 | Christianson et al. | |
| 2017/0312076 A1 | 11/2017 | Lutter et al. | |
| 2017/0312077 A1 | 11/2017 | Vidlund et al. | |
| 2017/0319333 A1 | 11/2017 | Tegels et al. | |
| 2018/0028314 A1 | 2/2018 | Ekvall et al. | |
| 2018/0078368 A1 | 3/2018 | Vidlund et al. | |
| 2018/0078370 A1 | 3/2018 | Kovalsky et al. | |
| 2018/0147055 A1 | 5/2018 | Vidlund et al. | |

FOREIGN PATENT DOCUMENTS

| | | |
|---|---|---|
| CN | 2902226 Y | 5/2007 |
| CN | 101146484 A | 3/2008 |
| CN | 101180010 A | 5/2008 |
| CN | 101984938 A | 3/2011 |
| CN | 102639179 A | 8/2012 |
| CN | 102869317 A | 1/2013 |
| CN | 102869318 A | 1/2013 |
| CN | 102869321 A | 1/2013 |
| CN | 103220993 A | 7/2013 |
| DE | 2246526 | 3/1973 |
| DE | 19532846 A1 | 3/1997 |
| DE | 19546692 A1 | 6/1997 |
| DE | 19857887 A1 | 7/2000 |
| DE | 19907646 A1 | 8/2000 |
| DE | 10049812 A1 | 4/2002 |
| DE | 10049813 C1 | 4/2002 |
| DE | 10049815 A1 | 4/2002 |
| DE | 102006052564 B3 | 12/2007 |
| DE | 102006052710 A1 | 5/2008 |
| DE | 102007043830 A1 | 4/2009 |
| DE | 102007043831 A1 | 4/2009 |
| EP | 0103546 A1 | 3/1984 |
| EP | 1057460 A1 | 12/2000 |
| EP | 1088529 A2 | 4/2001 |
| EP | 1469797 B1 | 11/2005 |
| EP | 2111800 A1 | 10/2009 |
| EP | 2193762 A1 | 6/2010 |
| EP | 2278944 A2 | 2/2011 |
| EP | 2747707 A1 | 7/2014 |
| EP | 2918248 A1 | 9/2015 |
| FR | 2788217 A1 | 7/2000 |
| FR | 2815844 A1 | 5/2002 |
| JP | 2003505146 A | 2/2003 |
| JP | 2005515836 A | 6/2005 |
| JP | 2009514628 A | 4/2009 |
| JP | 2009519783 A | 5/2009 |
| JP | 2013512765 A | 4/2013 |
| NL | 1017275 C2 | 8/2002 |
| SU | 1271508 | 11/1986 |
| WO | 9217118 A1 | 10/1992 |
| WO | 9301768 A1 | 2/1993 |
| WO | 9829057 A1 | 7/1998 |
| WO | 9940964 A1 | 8/1999 |
| WO | 9940964 A1 | 9/1999 |
| WO | 2000018333 A1 | 4/2000 |
| WO | 2000030550 A1 | 6/2000 |
| WO | 2000041652 A1 | 7/2000 |
| WO | 200047139 A1 | 8/2000 |
| WO | 2001035878 A2 | 5/2001 |
| WO | 2001049213 A2 | 7/2001 |
| WO | 0154625 A1 | 8/2001 |
| WO | 2001054624 A1 | 8/2001 |
| WO | 2001056512 A1 | 8/2001 |
| WO | 2001061289 A1 | 8/2001 |
| WO | 200176510 A2 | 10/2001 |
| WO | 2001082840 A1 | 11/2001 |
| WO | 2002004757 A1 | 1/2002 |
| WO | 2002022054 A1 | 3/2002 |
| WO | 2002028321 A2 | 4/2002 |
| WO | 0236048 A1 | 5/2002 |
| WO | 2002041789 A2 | 5/2002 |
| WO | 2002043620 A1 | 6/2002 |
| WO | 2002049540 A2 | 6/2002 |
| WO | 2002076348 A1 | 10/2002 |
| WO | 2003003943 A2 | 1/2003 |
| WO | 2003030776 A2 | 4/2003 |
| WO | 2003047468 A1 | 6/2003 |
| WO | 2003049619 A2 | 6/2003 |
| WO | 2004019825 A1 | 3/2004 |
| WO | 2005102181 A1 | 11/2005 |
| WO | 2006014233 A2 | 2/2006 |
| WO | 2006034008 A2 | 3/2006 |
| WO | 2006064490 A1 | 6/2006 |
| WO | 2006070372 A2 | 7/2006 |
| WO | 2006105009 A1 | 10/2006 |
| WO | 2006113906 A1 | 10/2006 |
| WO | 2006127756 A2 | 11/2006 |
| WO | 2007081412 A1 | 7/2007 |
| WO | 2007100408 A2 | 9/2007 |
| WO | 2008005405 A2 | 1/2008 |
| WO | 2008035337 A2 | 3/2008 |
| WO | 2008091515 A2 | 7/2008 |
| WO | 2008125906 A2 | 10/2008 |
| WO | 2008147964 A1 | 12/2008 |
| WO | 2009024859 A2 | 2/2009 |
| WO | 2009026563 A2 | 2/2009 |
| WO | 2009045338 A1 | 4/2009 |
| WO | 2009132187 A1 | 10/2009 |
| WO | 2010090878 A2 | 8/2010 |
| WO | 2010098857 A1 | 9/2010 |
| WO | 2010121076 A2 | 10/2010 |
| WO | 2011017440 A2 | 2/2011 |
| WO | 2011022658 A1 | 2/2011 |
| WO | 2011069048 A2 | 6/2011 |
| WO | 2011072084 A2 | 6/2011 |
| WO | 2011106735 A1 | 9/2011 |
| WO | 2011109813 A2 | 9/2011 |
| WO | 2011159342 A1 | 12/2011 |
| WO | 2011163275 A2 | 12/2011 |
| WO | 2012027487 A2 | 3/2012 |
| WO | 2012036742 A2 | 3/2012 |
| WO | 2012095116 A1 | 7/2012 |
| WO | 2012177942 A2 | 12/2012 |
| WO | 2013/028387 A2 | 2/2013 |
| WO | 2013045262 A1 | 4/2013 |
| WO | 2013059747 A1 | 4/2013 |
| WO | 2013096411 A1 | 6/2013 |
| WO | 2013175468 A2 | 11/2013 |
| WO | 2014121280 A2 | 8/2014 |
| WO | 2014144937 A2 | 9/2014 |
| WO | 2014162306 A2 | 10/2014 |
| WO | 2014189974 A1 | 11/2014 |
| WO | 2014210124 A1 | 12/2014 |
| WO | 2015051430 A1 | 4/2015 |
| WO | 2015058039 A1 | 4/2015 |
| WO | 2015063580 A2 | 5/2015 |
| WO | 2015065646 A1 | 5/2015 |
| WO | 2015/120122 A2 | 8/2015 |
| WO | 2015138306 A2 | 9/2015 |
| WO | 2015173609 A1 | 11/2015 |
| WO | 2016112085 A2 | 7/2016 |
| WO | 2016126942 A2 | 8/2016 |
| WO | 2016168609 A1 | 10/2016 |
| WO | 2016196933 A1 | 12/2016 |
| WO | 2017096157 A1 | 6/2017 |
| WO | 2017/132008 A1 | 8/2017 |
| WO | 2017218375 A1 | 12/2017 |
| WO | 2018005779 A1 | 1/2018 |
| WO | 2018013515 A1 | 1/2018 |

OTHER PUBLICATIONS

PCT/US2017/041454 Search Report completed Oct. 25, 2017.
Al Zaibag, Muayed, et al., "Percutaneous Balloon Valvotomy in

(56) References Cited

OTHER PUBLICATIONS

Tricuspid Stenos's," British Heart Journal, Jan. 1987, vol. 57, No. 1, pp. 51-53.
Al-Khaja, N. et al., "Eleven Years' Experience with Carpentier-Edwards Biological Valves in Relation to Survival and Complications," European Journal of Cardiothoracic Surgery, Jun. 30, 1989, 3:305-311.
Almagor, Y. et al., "Balloon Expandable Stent Implantation in Stenotic Right Heart Valved Conduits," Journal of the American College of Cardiology, Nov. 1, 1990, 16(6):1310-1314.
H. R. Andersen et al., "Transluminal Implantation of Artificial Heart Valves: Description of a New Expandable Aortic Valve and Initial Results with Implantation by Catheter Technique in Closed Chest Pigs," European Heart Journal, 1992, Issue 5, vol. 13, pp. 704-708.
Andersen, H. R., "History of Percutaneous Aortic Valve Prosthesis," Herz, Aug. 2009, 34(5):343-346.
Andersen, H. R., "Transluminal catheter implanted prosthetic heart valves," International Journal of Angiology, 1998, 7(2):102-106.
Robert C. Ashton Jr., "Development of an Intraluminal Device for the Treatment of Aortic Regurgitation: Prototype and in Vitro Testing System," Journal of Thoracic and Cardiovascular Surgery, 1996, Issue/vol. 112, pp. 979-983.
Benchimol, A. et al., "Simultaneous Left Ventricular Echocardiography and Aortic Blood Velocity During Rapid Right Ventricular Pacing in Man," The American Journal of the Medical Sciences, Jan.-Feb. 1977, 273(1):55-62.
G. M. Bernacca, et al., "Polyurethane Heart Valves: Fatigue Failure, Calcification, and Polyurethane Structure," Journal of Biomedical Materials Research, Mar. 5, 1997, Issue 3, vol. 34, pp. 371-379.
Boudjemline, Y. et al., "Steps Toward the Percutaneous Replacement of Atrioventricular Valves: An Experimental Study," Journal of the American College of Cardiology, Jul. 2005, 46(2):360-365.
Buckberg, G. et al., "Restoring Papillary Muscle Dimensions During Restoration in Dilated Hearts," Interactive cardiovascular and Thoracic Surgery, 2005, 4:475-477.
Chamberlain, G., "Ceramics Replace Body Parts," Design News, Jun. 9, 1997, Issue 11, vol. 52, 5 pages.
Choo, S. J. et al., "Aortic Root Geometry: Pattern of Differences Between Leaflets and Sinuses of Valsava," The Journal of Heart Valve Disease, Jul. 1999, 8:407-415.
Declaration of Malcolm J. R. Dalrymple-Hay, Nov. 9, 2012, pp. 1-11; with Curriculum Vitae, Oct. 4, 2012.
Dotter, C. T. et al., "Transluminal Treatment of Arteriosclerotic Obstruction. Description of a New Technic and a Preliminary Report of its Application," Circulation, Nov. 1964, 30:654-670.
Drawbaugh, K., "Feature—Heart Surgeons Explore Minimally Invasive Methods," Reuters Limited, Jul. 16, 1996, 3 pages.
Gray, H., The Aorta, Anatomy of the Human Body, 1918, Retrieved from the Internet <http://www.bartleby.com/107/142.html>, Dec. 10, 2012, 5 pages.
Gray, H., The Heart, Anatomy of the Human Body, 1918, Retrieved from the Internet <http://education.yahoo.com/reference/gray/subjects/subject/138>, Aug. 10, 2012, 9 pages.
Greenhalgh, E. S., "Design and characterization of a biomimetic prosthetic aortic heart valve," 1994, ProQuest Dissertations and Theses, Department of Fiber and Polymer Science, North Carolina State University at Raleigh, 159 pages.
Inoue, K. et al., "Clinical Application of Transvenous Mitral Commissurotomy by a New Balloon Catheter," The Journal of Thoracic and Cardiovascular Surgery, 1984, 87:394-402.
Jin, X. Y. et al., "Aortic Root Geometry and Stentless Porcine Valve Competence," Seminars in Thoracic and Cardiovascular Surgery, Oct. 1999, 11(4):145-150.
Knudsen, L L. et al., "Catheter-implanted prosthetic heart valves. Transluminal catheter implantation of a new expandable artificial heart valve in the descending thoracic aorta in isolated vessels and closed chest pigs," The International Journal of Artificial Organs, 1993, 16(5):253-262.
Kolata, G., "Device That Opens Clogged Arteries Gets a Failing Grade in a New Study," New York Times [online], <http://www.nytimes.com/1991/01/03/health/device-that-opens-clogged-ar-teries-gets-a-faili ...,>, published Jan. 3, 1991,retrieved from the Internet on Feb. 5, 2016, 3 pages.
Lawrence, D. D., "Percutaneous Endovascular Graft: Experimental Evaluation," Radiology, 1987, 163:357-360.
Lozonschi, L., et al. "Transapical mitral valved stent implantation: A survival series in swine," The Journal of Thoracic and Cardiovascular Surgery, 140(2):422-426 (Aug. 2010) published online Mar. 12, 2010, 1 page.
Lutter, Georg, et al., Mitral valved stent implantation, European Journal of Cardio-Thoracic Surgery, 2010, vol. 38, pp. 350-355.
Ma, L. et al., "Double-crowned valved stents for off-pump mitral valve replacement," European Journal of Cardio-Thoracic Surgery, Aug. 2005, 28(2): 194-198.
Moazami, N. et al., "Transluminal aortic valve placement: A feasibility study with a newly designed collapsible aortic calve," ASAIO Journal, Sep./ Oct. 1996, 42(5):M381-M385.
Orton, C., "Mitralseal: Hybrid Transcatheter Mitral Valve Replacement," Symposium: Small Animal Proceedings, 2011, pp. 311-312.
Pavcnik, M.D., Ph.D., Dusan, et al. "Development and Initial Experimental Evaluation of a Prosthetic Aortic Valve for Transcatheter Placement," Cardiovascular Radiology 1992; 183:151-154.
Porstmann, W. et al., "Der Verschluβ des Ductus Arteriosus Persistens ohne Thorakotomie," Thoraxchirurgie Vaskuläre Chirurgie, Band 15, Heft 2, Stuttgart, Apr. 1967, pp. 199-203.
Rashkind, W. J., "Creation of an Atrial Septal Defect Without Thoracotomy," The Journal of the American Medical Association, Jun. 13, 1966, 196( 11 ): 173-174.
Rashkind, W. J., "Historical Aspects of Interventional Cardiology: Past, Present, Future," Texas Heart Institute Journal, Dec. 1986, 13(4):363-367.
Reul, H. et al., "The Geomety of the Aortic Root in Health, at Valve Disease and After Valve Replacement," J. Biomechanics, 1990, 23(2):181-191.
Rosch, J. et al., "The Birth, Early Years and Future of Interventional Radiology," J Vasc Interv Radiol., Jul. 2003, 4:841-853.
Ross, D. N., "Aortic Valve Surgery," Guy's Hospital, London, 1968, pp. 192-197.
Rousseau, E. P. M. et al., "A Mechanical Analysis of the Closed Hancock Heart Valve Prosthesis," Journal of Biomechanics, 1998, 21(7):545-562.
Sabbah, A. N. et al., "Mechanical Factors in the Degeneration of Porcine Bioprosthetic Valves: An Overview," Dec. 1989, Journal of Cardiac Surgery, 4(4):302-309.
Selby, M.D., J. Bayne, "Experience with New Retrieval Forceps for Foreign Body Removal in the Vascular, Urinary, and Biliary Systems," Radiology 1990; 176:535-138.
Serruys, P.W., et al., "Stenting of Coronary Arteries. Are we the Sorcerer's Apprentice?," European Heart Journal (1989) 10, 774-782, pp. 37-45, Jun. 13, 1989.
"Shape Memory Alloys," Retrieved from the Internet: <http://webdocs.cs.ualberta.ca/about.database/MEMS/sma.html>, Nov. 14, 2012, 3 pages.
Sigwart, U., "An Overview of Intravascular Stents: Old and New," Chapter 48, Interventional Cardiology, 2nd Edition, W.B. Saunders Company, Philadelphia, PA, © 1994, 1990, pp. 803-815.
Tofeig, M. et al., "Transcatheter Closure of a Mid-Muscular Ventricular Septal Defect with an Amplatzer VSD Occluder Device," Heart, 1999, 81:438-440.
Uchida, Barry T., et al., "Modifications of Gianturco Expandable Wire Stents," AJR:150, May 1988, Dec. 3, 1987, pp. 1185-1187.
Watt, A.H., et al. "Intravenous Adenosine in the Treatment of Supraventricular Tachycardia; a Dose-Ranging Study and Interaction with Dipyridamole," British Journal of Clinical Pharmacology (1986), 21, pp. 227-230.
Webb, J. G. et al., "Percutaneous Aortic Valve Implantation Retrograde from the Femoral Artery," Circulation, 2006, 113:842-850.
Wheatley, M.D., David J., "Valve Prostheses," Rob & Smith's Operative Surgery, Fourth Edition, pp. 415-424, ButtenNorths 1986.
Yoganathan, A. P. et al., "The Current Status of Prosthetic Heart

(56) References Cited

OTHER PUBLICATIONS

Valves," In Polymetric Materials and Artificial Organs, Mar. 20, 1983, pp. 111-150, American Chemical Society.

* cited by examiner

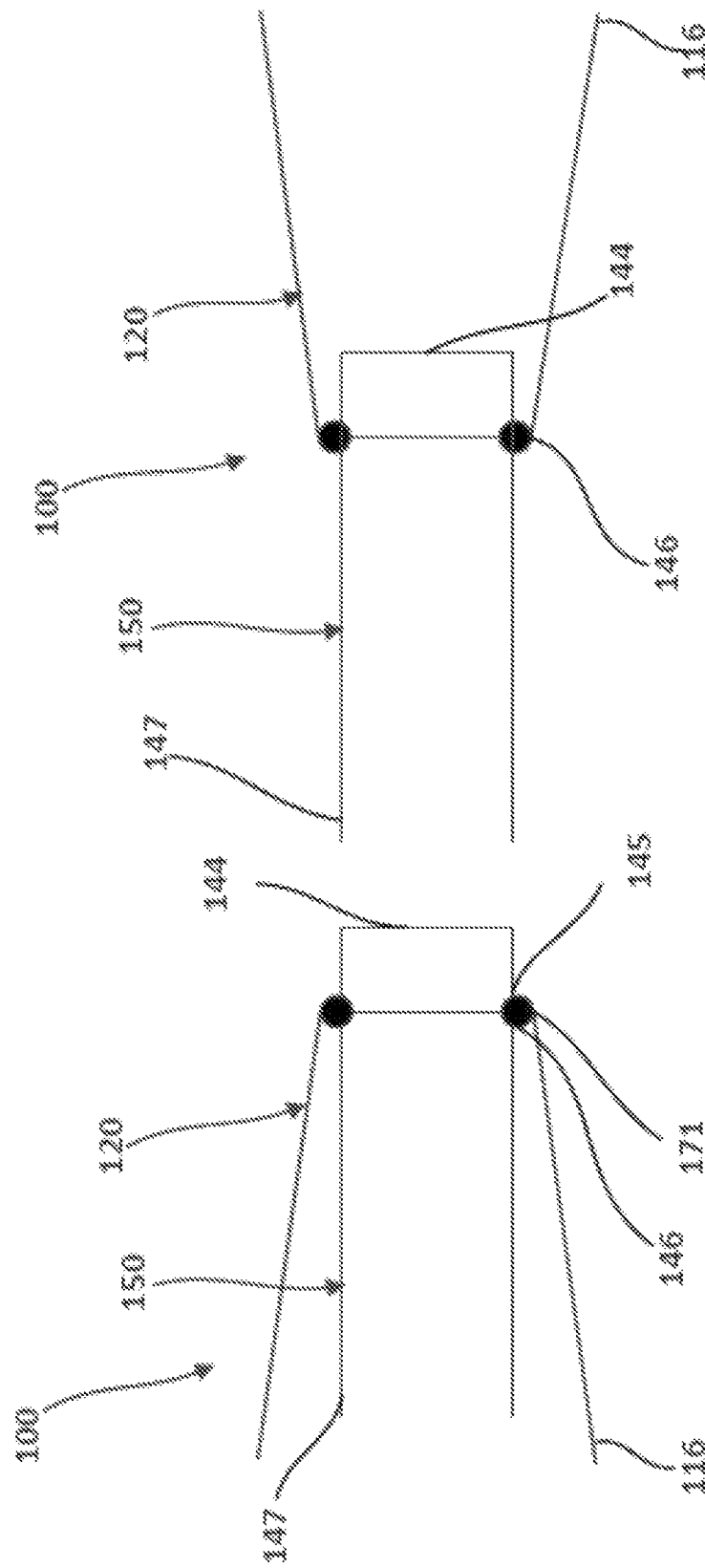

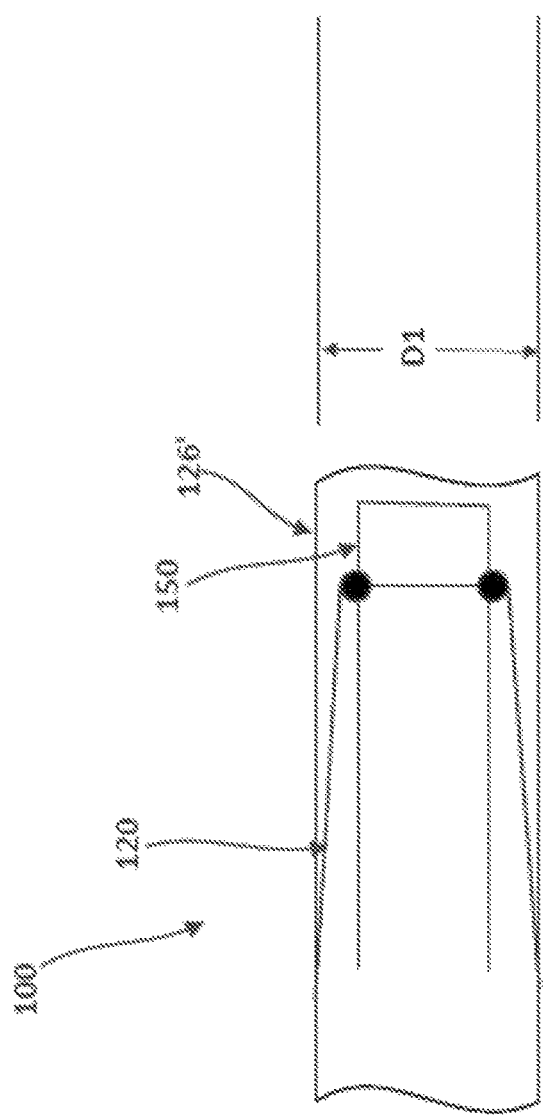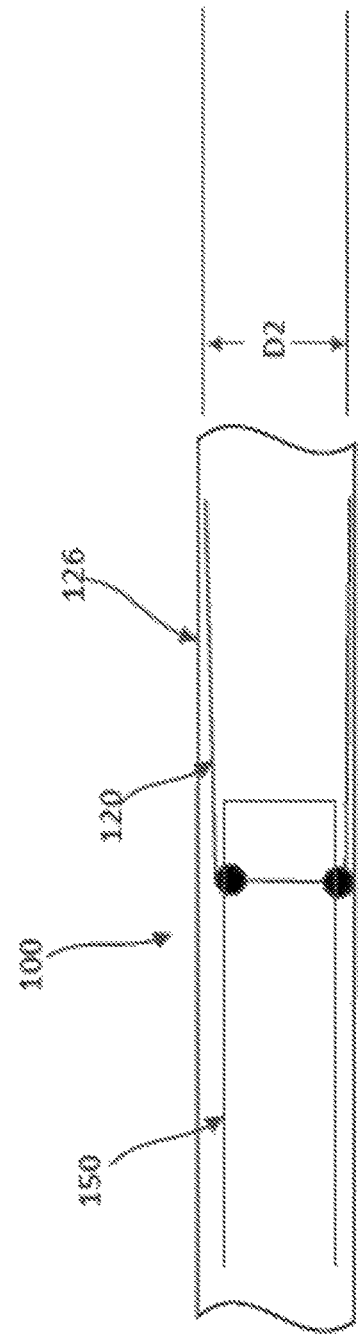

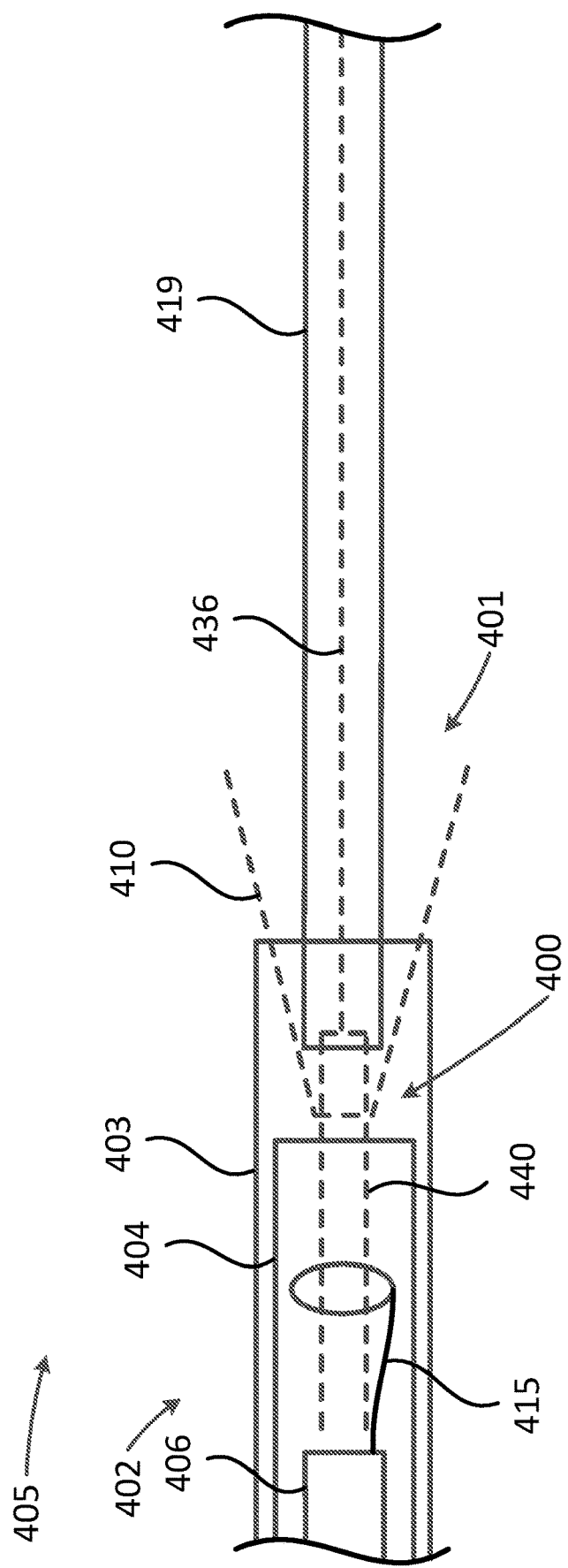

APPARATUS AND METHODS FOR TRANS-SEPTAL RETRIEVAL OF PROSTHETIC HEART VALVES

CROSS-REFERENCE TO RELATED APPLICATIONS

This application is a national phase entry under 35 U.S.C. § 371 of International Application No. PCT/US2017/041454 filed Jul. 11, 2017, published in English, which claims priority to and the benefit of U.S. Provisional Patent Application No. 62/361,228, entitled "Apparatus and Methods for Trans-Septal Retrieval of Prosthetic Mitral Valves," filed Jul. 12, 2016, the disclosures of which are incorporated herein by reference in their entireties.

BACKGROUND

Embodiments are described herein that relate to devices and methods for use in the retrieval of prosthetic valves, and particularly to devices and methods for trans-septal retrieval of expandable prosthetic mitral valves.

Prosthetic heart valves can pose particular challenges for delivery and deployment within a heart. Valvular heart disease, and specifically, aortic and mitral valve disease is a significant health issue in the United States (US); annually approximately 90,000 valve replacements are conducted in the US. Traditional valve replacement surgery involving the orthotopic replacement of a heart valve is considered an "open heart" surgical procedure. Briefly, the procedure necessitates surgical opening of the thorax, the initiation of extra-corporeal circulation with a heart-lung machine, stopping and opening the heart, excision and replacement of the diseased valve, and re-starting of the heart. While valve replacement surgery typically carries a 1-4% mortality risk in otherwise healthy persons, a significantly higher morbidity is associated to the procedure largely due to the necessity for extra-corporeal circulation. Further, open heart surgery is often poorly tolerated in elderly patients. Thus elimination of the extra-corporeal component of the procedure could result in reduction in morbidities and cost of valve replacement therapies could be significantly reduced.

While replacement of the aortic valve in a transcatheter manner is the subject of intense investigation, lesser attention has been focused on the mitral valve. This is in part reflective of the greater level of complexity associated to the native mitral valve apparatus, and thus, a greater level of difficulty with regards to inserting, anchoring, and retrieving the replacement prosthesis. In particular, repositioning of a collapsible replacement prosthesis and retrieval of a collapsible replacement prosthesis from the native mitral valve present challenges. For example, a prosthetic heart valve may be delivered and secured percutaneously or intravenously using a catheter and endoscope. The disengagement of the anchoring mechanisms and collapsing of the prosthetic heart valve, however, presents a need for more active prosthetic heart valve manipulation within the heart.

Thus, a need exists for delivery devices and methods for transcatheter mitral valve repositioning and/or retrieval.

SUMMARY

Apparatus and methods are described herein for use in the transvascular repositioning and retrieval of a previously-deployed prosthetic mitral valve. In some embodiments, a method for transfemoral retrieval of a prosthetic heart valve implanted within a heart includes inserting a retrieval assembly through the femoral vein and into a heart of a patient until a distal end portion of the retrieval assembly is disposed in the atrium of the heart. The prosthetic heart valve is formed with a shape-memory material. The retrieval assembly includes an outer catheter, a middle catheter, a snare catheter, and a snare member. The snare member is moved distally out of a lumen of the snare catheter and into engagement with an inner frame of the prosthetic heart valve. The retrieval assembly can be manipulated to invert an outer frame of the prosthetic heart valve such that the prosthetic heart valve can be collapsed and retracted into a lumen of the retrieval assembly. In some embodiments, a positioning catheter can be inserted through the apex of the heart to assist in positioning and inverting the prosthetic heart valve.

BRIEF DESCRIPTION OF THE FIGURES

FIGS. 1A and 1B are schematic illustrations of a portion of a prosthetic heart valve, according to an embodiment, shown in a first configuration and a second configuration, respectively.

FIGS. 1C and 1D are schematic illustrations of the portion of the prosthetic heart valve of FIGS. 1A and 1B, respectively, shown disposed within a delivery sheath.

FIG. 25C is a schematic illustration of the prosthetic mitral valve retrieval system of FIG. 25A with the prosthetic valve in a third configuration in which an outer frame of the prosthetic valve is in an inverted configuration.

DETAILED DESCRIPTION

Apparatus and methods are described herein for retrieval or repositioning of a previously-implanted prosthetic heart valve via a transfemoral approach. Such an approach can be similar to the transfemoral delivery approach for delivering a prosthetic heart valve as described in PCT International Application No. PCT/US2016/012305 (referred to herein as "the '305 PCT Application") with respect to, for example, FIGS. 43-61, and as described herein, with respect to, for example, FIGS. 22-24.

In some embodiments, a method for transfemoral retrieval of a prosthetic mitral valve includes inserting a retrieval assembly through the femoral vein and septum of a heart of a patient until a distal end portion of the retrieval assembly is disposed in the left atrium of the heart. The prosthetic mitral valve is formed with a shape-memory material. The retrieval assembly includes an outer catheter, a middle catheter, a snare catheter, and a snare member. The snare member is moved distally out of the retrieval assembly into engagement with an inner frame of the prosthetic mitral valve. The retrieval assembly can be manipulated to invert an outer frame of the prosthetic mitral valve such that the prosthetic mitral valve can be collapsed and retracted into a lumen of the retrieval assembly. In some embodiments, a positioning catheter can be inserted through the apex of the heart to assist in positioning and inverting the prosthetic mitral valve.

In some embodiments, an apparatus includes a retrieval system for a prosthetic heart valve previously deployed in a valve annulus. A retrieval assembly of the retrieval system can approach the deployed prosthetic heart valve transseptally, capture the prosthetic heart valve, dislodge the prosthetic heart valve from the valve annulus, and then either reposition and redeploy the prosthetic heart valve or remove the prosthetic heart valve from the heart. In some embodiments, the repositioning or removal of the previously-deployed prosthetic heart valve can be performed via an outpatient catheterization procedure without requiring major surgery.

Figure 2B:
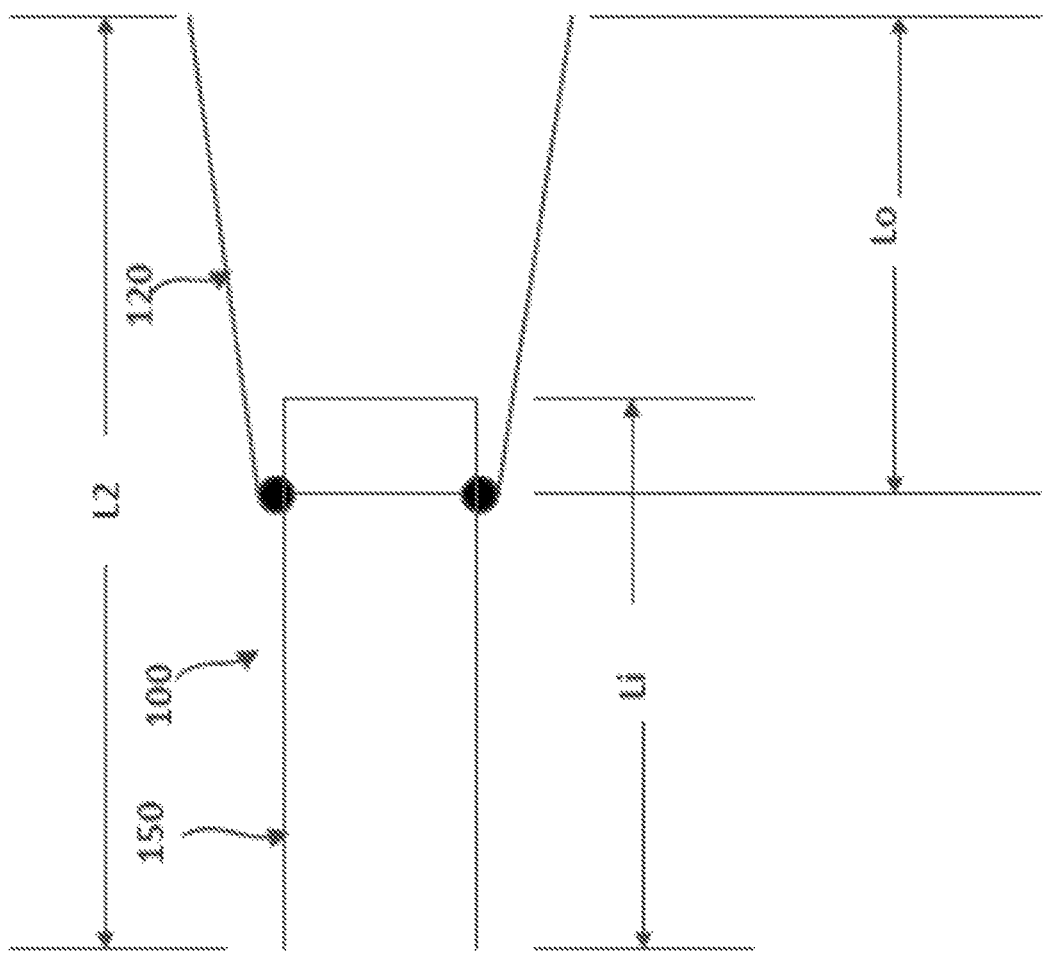
FIGS. 2A and 2B are schematic illustrations of the portion of a prosthetic heart valve of FIGS. 1A and 1B, shown in the first configuration and the second configuration, respectively.
Figure 2A:
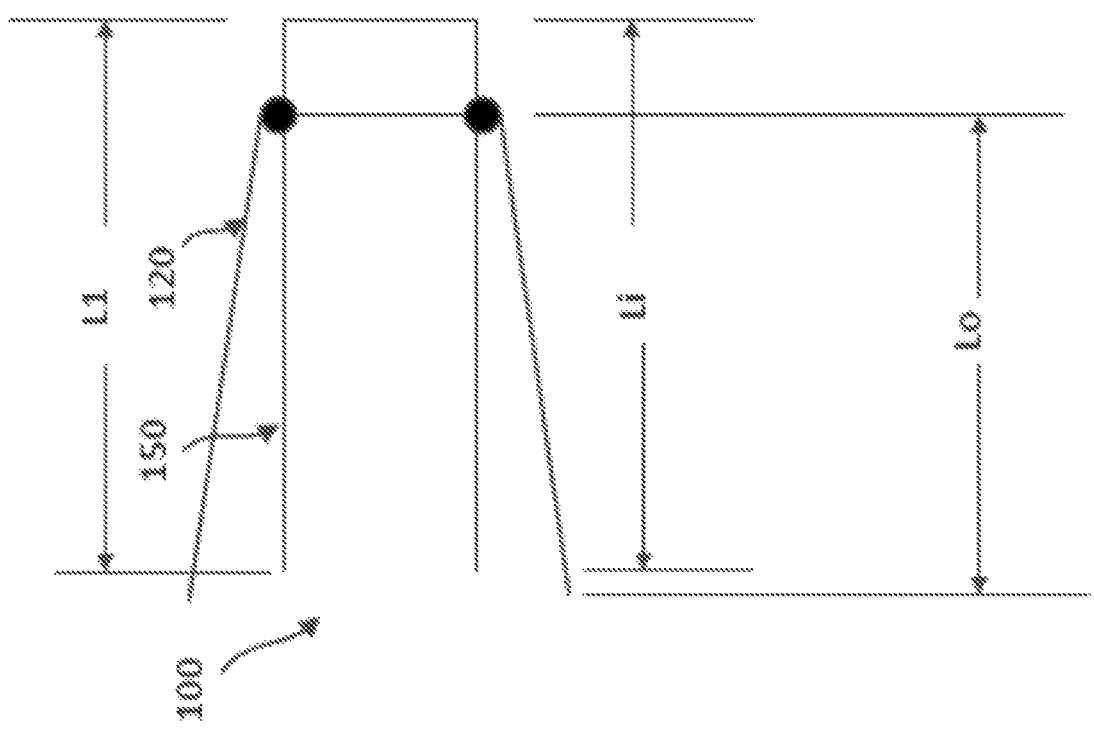

FIGS. 1A and 1B are schematic illustrations of a portion of a prosthetic heart valve 100, according to an embodiment, shown in a first configuration and a second configuration respectively, and FIGS. 1C and 1D illustrate the portions of the prosthetic heart valve 100 of FIGS. 1A and 1B, respectively, shown disposed within a lumen of a delivery sheath 126. FIGS. 2A and 2B illustrate a portion of the prosthetic heart valve 100 of FIGS. 1A and 1B, respectively, and show length dimensions for the prosthetic heart valve in each of the first configuration and the second configuration. The prosthetic heart valve 100 (also referred to herein as "prosthetic valve" or "valve") can be, for example, a prosthetic mitral valve. The valve 100 includes an outer frame 120 and an inner frame 150. The outer frame 120 and the inner frame 150 are each formed as a tubular structure as described in more detail below with reference to FIGS. 3-15. The outer frame 120 and the inner frame 150 can be coupled together at multiple coupling joints 146 disposed about a perimeter of the inner frame 150 and a perimeter of the outer frame 120 as described in more detail below. The valve 100 can also include other features, such as those described with respect to FIGS. 3-15 below. For illustration purposes, only the inner frame 150 and the outer frame 120 are discussed with respect to FIGS. 1A-2B. The various characteristics and features of valve 100 described with respect to FIGS. 1A-2B can apply to any of the prosthetic valves described here.

The outer frame 120 is configured to have a biased expanded or undeformed shape and can be manipulated and/or deformed (e.g., compressed or constrained) and, when released, return to its original (expanded or undeformed) shape. For example, the outer frame 120 can be formed of materials, such as metals or plastics, which have shape memory properties. With regards to metals, Nitinol® has been found to be especially useful since it can be processed to be austenitic, martensitic or super elastic. Other shape memory alloys, such as Cu—Zn—Al—Ni alloys, and Cu—Al—Ni alloys, may also be used. The inner frame 150 can be formed from a laser-cut tube of Nitinol®. The inner frame 150 can also have a biased expanded or undeformed shape and can be manipulated and/or deformed (e.g., compressed and/or constrained) and, when released, return to its original (expanded or undeformed) shape. Further details regarding the inner frame 150 and the outer frame 120 are described below with respect to valve 200 and FIGS. 3-15.

The valve 100 can be delivered and deployed within a left atrium of a heart using a variety of different delivery approaches including, for example, a transfemoral delivery approach, as described in the '305 PCT application, or a transatrial approach, as described in U.S. Provisional Patent Application Ser. No. 62/220,704, entitled "Apparatus and Methods for Transatrial Delivery of Prosthetic Mitral Valve," or a transjugular approach as described in U.S. Provisional Patent Application Ser. No. 62/305,678 and in U.S. Patent Application Pub. No. 2017/0079790, each incorporated by reference herein. As described above, in some situations, such as when delivering a prosthetic valve to the heart via a transfemoral or transatrial approach, because of the smaller size of the lumen of the delivery sheath, the size of the prosthetic valve during delivery should be sized accordingly. Thus, it is desirable to have a prosthetic valve that can be reconfigured between a biased expanded configuration for implantation in the heart (e.g., within a native mitral annulus) and a delivery configuration that has a smaller outer perimeter or profile to allow for delivery within the lumen of the delivery sheath. The prosthetic valve 100 and the embodiments of a prosthetic valve described herein can be constructed and formed to achieve these desired functions and characteristics.

More specifically, the valve 100 can have a biased expanded configuration (as shown in FIGS. 1A and 2A), an inverted configuration (as shown in FIGS. 1B and 2B), and a compressed or collapsed configuration (as shown in FIGS. 1C and 1D). The expanded configuration allows the valve 100 to function when implanted within the heart. The valve 100 can be moved to the inverted configuration and the compressed or collapsed configuration for delivery of the valve 100 to the heart of a patient.

To enable the valve 100 to be moved to the inverted configuration, the outer frame 120 can be coupled to the inner frame 150 in such a manner to allow the outer frame 120 to move relative to the inner frame 150. More specifically, the coupling joints 146 can couple the outer frame 120 to the inner frame 150 in such a manner to allow the outer frame 120 to be moved relative to the inner frame 150. For example, in some embodiments, the coupling joints 146 can be configured to allow the outer frame 120 to rotate about the coupling joint 146 relative to the inner frame 150. In some embodiments, coupling joints can provide a pivotal coupling between the outer frame 120 and the inner frame 150. In some embodiments, the coupling joints can provide a flexible attachment between the outer frame 120 and the inner frame 150. The coupling joints 146 can be a variety of different types and configurations as described herein with reference to the various embodiments of a prosthetic valve. For example, the coupling joints 146 can include a living hinge, a flexible member, sutures, a suture wrapped through an opening, a pin or tab inserted through an opening, or any combinations thereof.

To move the valve 100 from the expanded configuration (FIG. 1A) to the inverted configuration (FIG. 1B), the outer frame 120 is moved to a prolapsed or inverted configuration relative to the inner frame 150, as shown in FIGS. 1B, 1D and 2B, by moving (e.g., rotating, pivoting, flexing) the outer frame 120 about the coupling joints 146. The elastic or superelastic structure of outer frame 120 of valve 100 also allows the outer frame 120 to be moved to, and disposed in, the prolapsed or inverted configuration relative to the inner frame 150. To move the outer frame 120 to the inverted configuration relative to the inner frame 150, the outer frame 120 is folded or inverted distally (to the right in FIG. 1B) relative to the inner frame 150 via the coupling joints 146. As shown in FIGS. 1A and 2A, the outer frame 120 is in a first position relative to the inner frame 150 prior to being inverted in which an open or free end portion 116 (also referred to as the atrium portion 116 of the outer frame 120) is disposed proximally or to the left of the coupling joints 146 and in the same direction as a free end portion 147 (also referred to as a second end portion of the inner frame) of the inner frame 150. When the outer frame 120 is moved to an inverted configuration (i.e., second position relative to the inner frame 150), the free end portion 116 is disposed distally of the coupling joints 146 (or to the right in FIGS. 1B and 2B) and in an opposite direction as the free end portion 147 of the inner frame 150. Said another way, when the valve 100 is in a biased expanded configuration (e.g., FIG. 1A), the coupling joints 146 are disposed between a first end portion 144 (also referred to as a tether coupling portion) of the inner frame 150 and the free end portion 116 of the outer frame 120. When the valve 100 is in the inverted configuration (e.g., FIG. 1B) (i.e., the outer frame 120 has been moved to an inverted configuration or position), the coupling joints 146 are disposed between the free end portion or second end portion 147 of the inner frame 150 and the free end portion 116 of the outer frame 120.

When in the inverted configuration, an overall length of the valve 100 is increased, but a length of the inner frame 150 and a length of the outer frame 120 remains the same (or substantially the same). For example, as shown in FIGS. 2A and 2B an overall length L1 of the valve 100 in the biased expanded configuration (prior to being inverted as shown in FIG. 2A) is less than the overall length L2 of the valve 100 when in the inverted configuration (FIG. 2B). A length Li of the inner frame 150 and a length Lo of the outer frame 120 is substantially the same (or the same) when the valve 100 is in both the biased expanded configuration and the inverted configuration. In addition, in some instances, depending on the specific configuration of the outer frame, an overall outer perimeter or outer diameter of the valve 100 can be smaller when the valve 100 is in the inverted configuration.

With the valve 100 in the inverted configuration, the valve 100 can be placed within a lumen of the delivery sheath 126 for delivery of the valve 100 to the left atrium of the heart, as shown in FIG. 1D. When placed within the lumen of the delivery sheath 126, the valve 100 is moved to the collapsed or compressed configuration in which the outer diameter or outer perimeter of the valve 100 is reduced. Because the valve 100 is in the inverted configuration, the valve 100 is able to be placed within a smaller delivery sheath 126 than would otherwise be possible. For example, for comparison purposes, FIG. 1C illustrates the valve 100 placed within a lumen of a delivery sheath 126' where the valve 100 has not been moved to an inverted configuration prior to being disposed within the delivery sheath 126'. As shown in FIG. 1C, an outer diameter of the valve 100 is reduced, but not to as small of a diameter as for the valve 100 when placed in a delivery sheath 126 when in the inverted configuration. Thus, in FIG. 1C, the valve 100 has an overall outer perimeter or outer diameter D1 and in FIG. 1D, the valve 100 has an overall outer perimeter or outer diameter D2, which is less than D1.

Thus, by disposing the outer frame 120 in the inverted configuration, the valve 100 can be collapsed into a smaller overall diameter, i.e. placed in a smaller diameter delivery sheath 126, than would be possible if the valve 100 were merely collapsed radially. This is because when the valve is in the biased expanded configuration, the inner frame 150 is nested within an interior of the outer frame 120, and thus the outer frame 120 must be collapsed around the inner frame 150. In some embodiments, the inner frame 150 and the outer frame 120 are disposed concentrically. Whereas in the inverted configuration, the inner frame 150 and the outer frame 120 are arranged axially with respect to each other (i.e., the inner frame is not nested within the outer frame 150), such that the outer frame 120 can be collapsed without needing to accommodate all of the structure of the inner frame 150 inside it. In other words, with the inner frame 150 disposed mostly inside or nested within the outer frame 120, the layers or bulk of the frame structures cannot be compressed to as small a diameter. In addition, if the frames are nested, the structure is less flexible, and therefore, more force is needed to bend the valve, e.g. to pass through tortuous vasculature or to make tight turn in the left atrium after passing through the atrial septum to be properly oriented for insertion into the mitral valve annulus.

Figure 3:
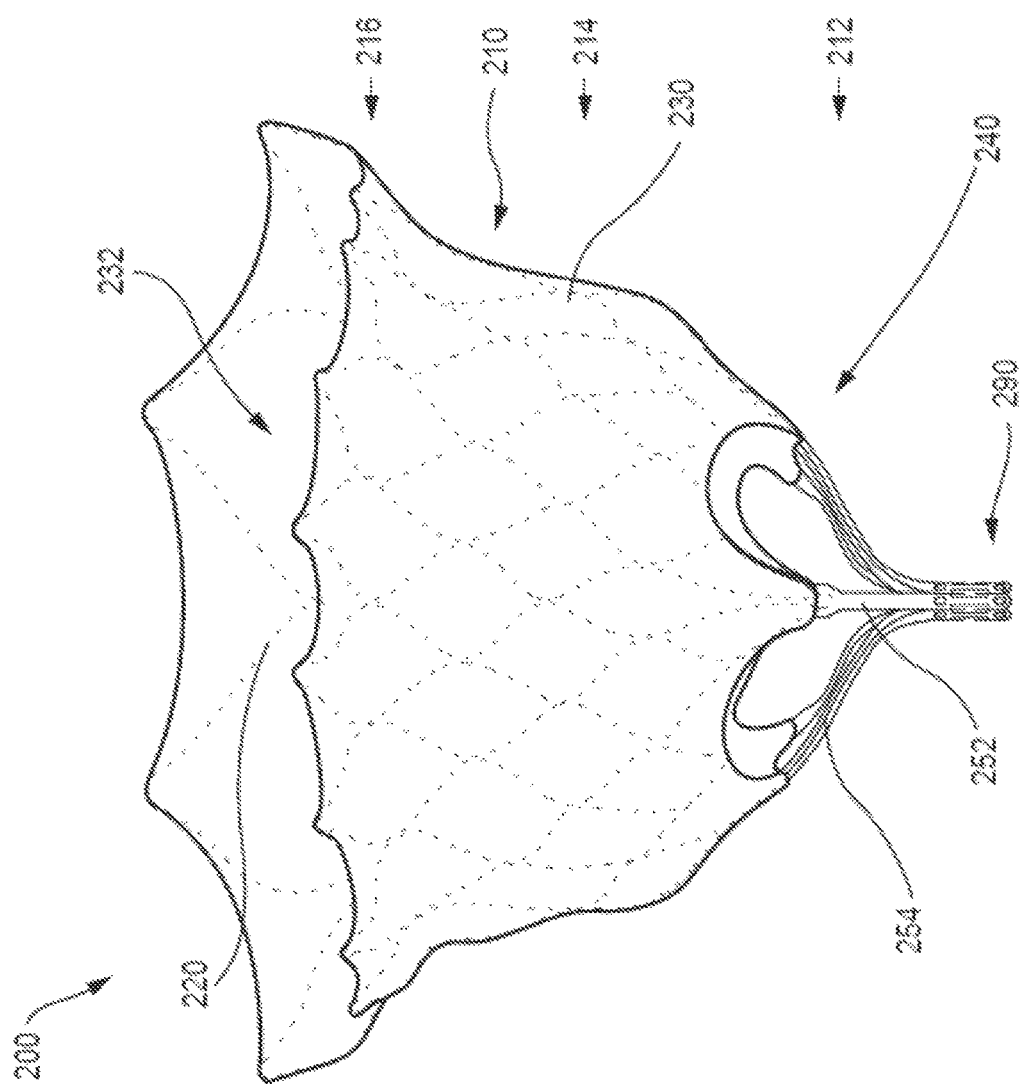
FIGS. 3-5 are front, bottom, and top views of a prosthetic heart valve according to an embodiment.
Figure 4:
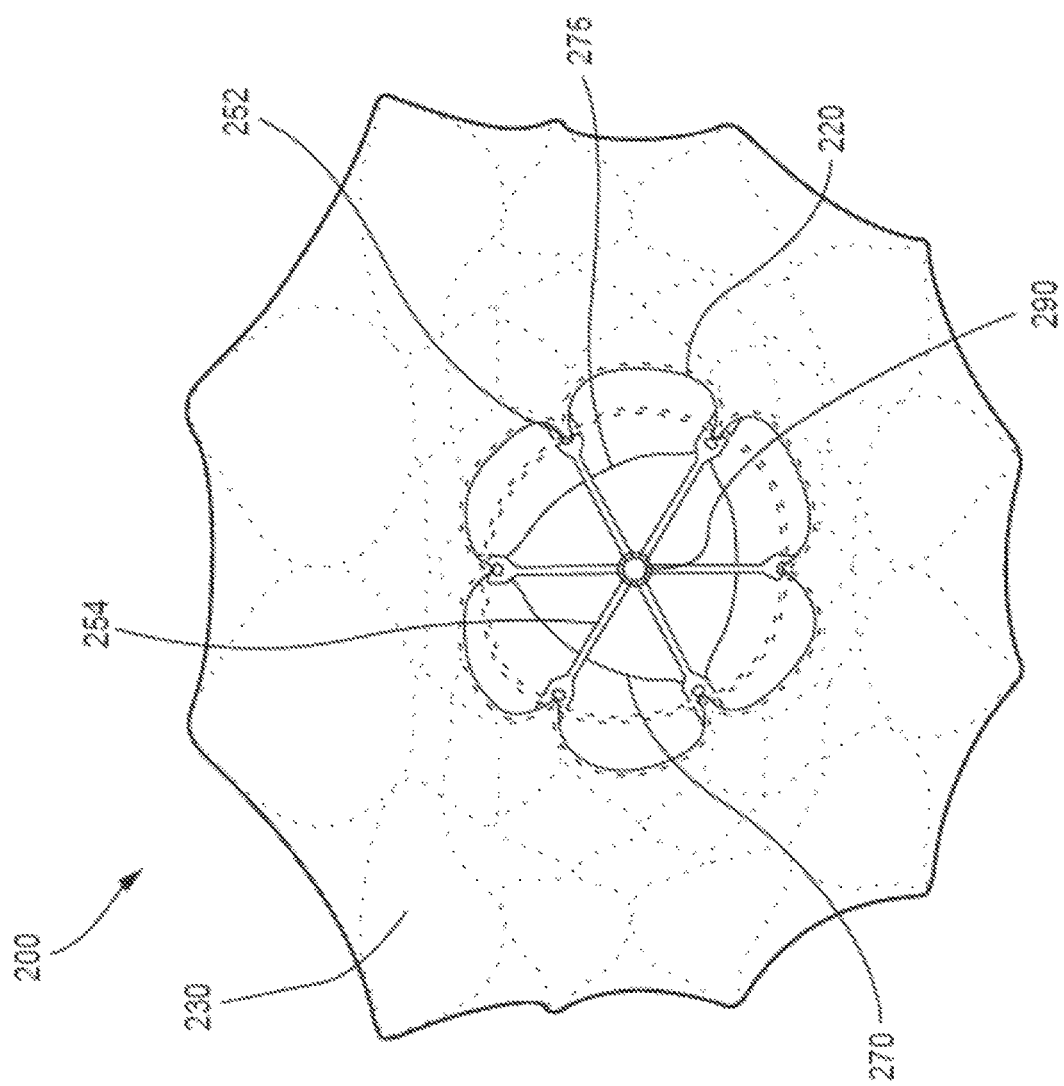
Figure 5:
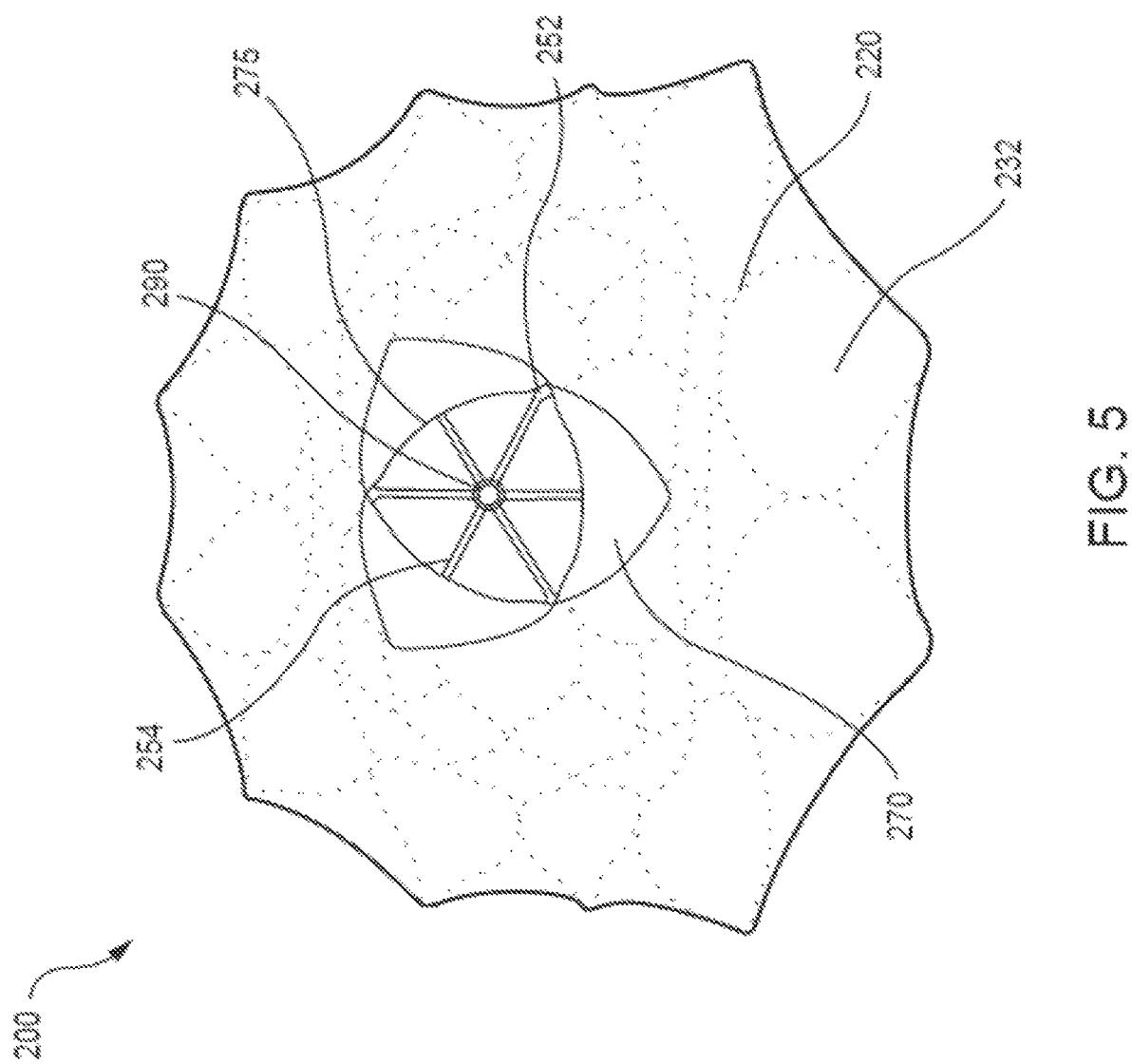

FIGS. 3-14 illustrate another embodiment of a prosthetic heart valve that can be delivered and deployed within a left atrium of a heart using a variety of different delivery approaches including, for example, a transfemoral delivery approach, a transatrial delivery approach, or a transjugular approach. FIGS. 3-5 are front, bottom, and top views, respectively, of a prosthetic heart valve 200 according to an embodiment. Prosthetic heart valve 200 (also referred to herein as "valve" or "prosthetic valve") is designed to replace a damaged or diseased native heart valve such as a mitral valve. Valve 200 includes an outer frame assembly 210 and an inner valve assembly 240 coupled to the outer frame assembly 210.

As shown, outer frame assembly 210 includes an outer frame 220, covered on all or a portion of its outer face with an outer covering 230, and covered on all or a portion of its inner face by an inner covering 232. Outer frame 220 can provide several functions for prosthetic heart valve 200, including serving as the primary structure, as an anchoring mechanism and/or an attachment point for a separate anchoring mechanism to anchor the valve to the native heart valve apparatus, a support to carry inner valve assembly 240, and/or a seal to inhibit paravalvular leakage between prosthetic heart valve 200 and the native heart valve apparatus.

Outer frame 220 has a biased expanded configuration and can be manipulated and/or deformed (e.g., compressed and/or constrained) and, when released, return to its original unconstrained shape. To achieve this, outer frame 220 can be formed of materials, such as metals or plastics, which have shape memory properties. With regards to metals, Nitinol® has been found to be especially useful since it can be processed to be austenitic, martensitic or super elastic. Other shape memory alloys, such as Cu—Zn—Al—Ni alloys, and Cu—Al—Ni alloys, may also be used.

As best shown in FIG. 3, outer frame assembly 210 has an upper end (e.g., at the atrium portion 216), a lower end (e.g., at the ventricle portion 212), and a medial portion (e.g., at the annulus portion 214) therebetween. The upper end or atrium portion 216 (also referred to as "outer free end portion") defines an open end portion of the outer frame assembly 210. The medial or annulus portion 214 of the outer frame assembly 210 has a perimeter that is configured (e.g., sized, shaped) to fit into an annulus of a native atrioventricular valve. The upper end of the outer frame assembly 210 has a perimeter that is larger than the perimeter of the medial portion. In some embodiments, the perimeter of the upper end of the outer frame assembly 210 has a perimeter that is substantially larger than the perimeter of the medial portion. As shown best in FIG. 5, the upper end and the medial portion of the outer frame assembly 210 has a D-shaped cross-section. In this manner, the outer frame assembly 210 promotes a suitable fit into the annulus of the native atrioventricular valve.

Inner valve assembly 240 includes an inner frame 250, an outer covering (not shown), and leaflets 270. As shown, the inner valve assembly 240 includes an upper portion having a periphery formed with multiple arches. The inner frame 250 includes six axial posts or frame members that support the outer covering and leaflets 270. Leaflets 270 are attached along three of the posts, shown as commissure posts 252 (best illustrated in FIG. 4), and the outer covering is attached to the other three posts, 254 (best illustrated in FIG. 4), and optionally to commissure posts 252. Each of the outer covering and leaflets 270 are formed of approximately rectangular sheets of material, which are joined together at their upper, or atrium end. The lower, ventricle end of outer covering may be joined to inner covering 232 of outer frame assembly 210, and the lower, ventricle end of leaflets 270 may form free edges 275, though coupled to the lower ends of commissure posts 252.

Although inner valve assembly 240 is shown as having three leaflets, in other embodiments, an inner valve assembly can include any suitable number of leaflets. The leaflets 270 are movable between an open configuration and a closed configuration in which the leaflets 270 coapt, or meet in a sealing abutment.

Outer covering 230 of the outer frame assembly 210 and inner covering 232 of outer frame assembly 210, outer covering of the inner valve assembly 240 and leaflets 270 of the inner valve assembly 240 may be formed of any suitable material, or combination of materials, such as those discussed above. In this embodiment, the inner covering 232 of the outer frame assembly 210, the outer covering of the inner valve assembly 240, and the leaflets 270 of the inner valve assembly 240 are formed, at least in part, of porcine pericardium. Moreover, in this embodiment, the outer covering 230 of the outer frame assembly 210 is formed, at least in part, of polyester.

Figure 6:
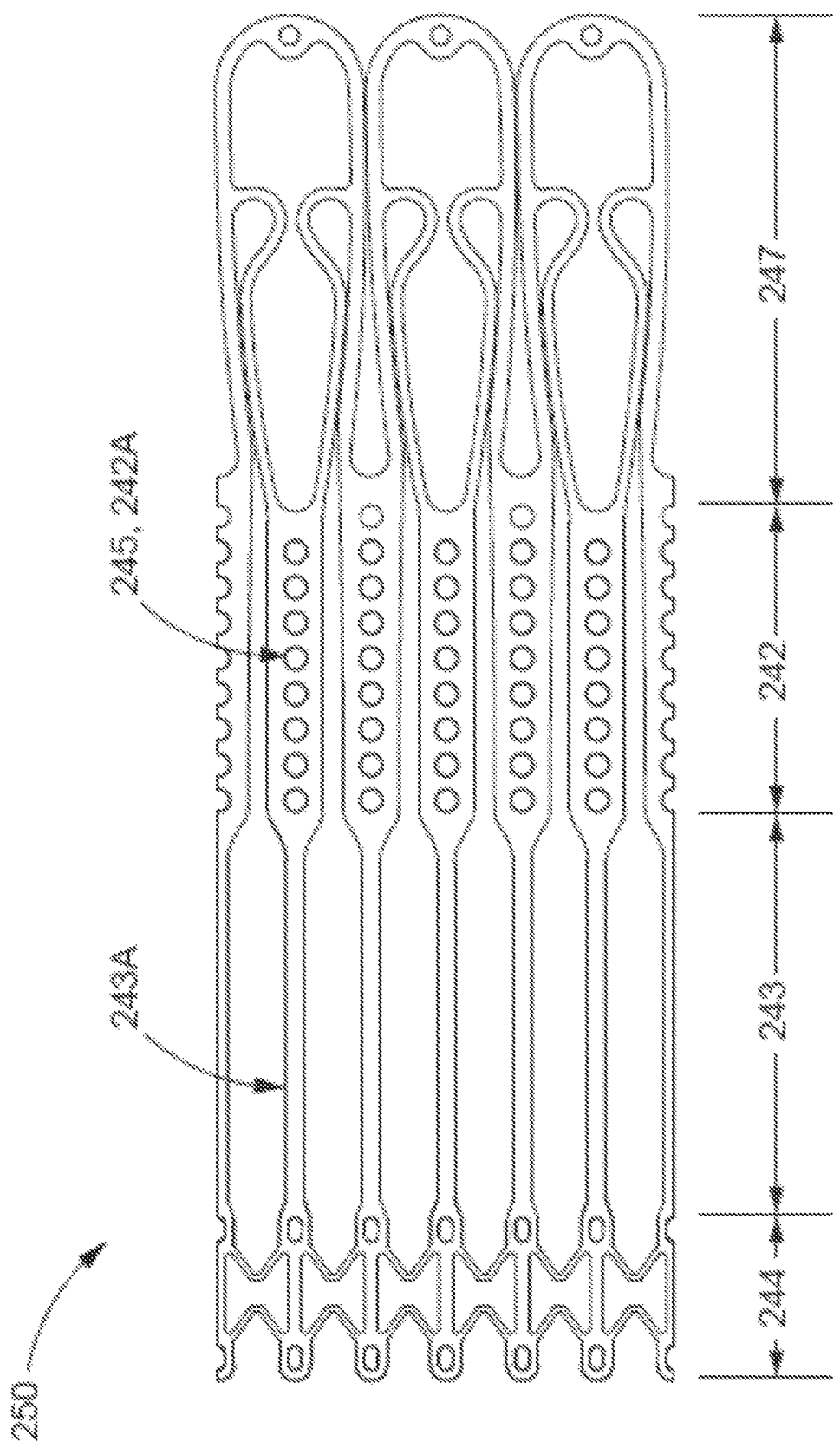
FIG. 6 is an opened and flattened view of the inner frame of the prosthetic heart valve of FIGS. 3-5, in an unexpanded configuration.
Figure 7:
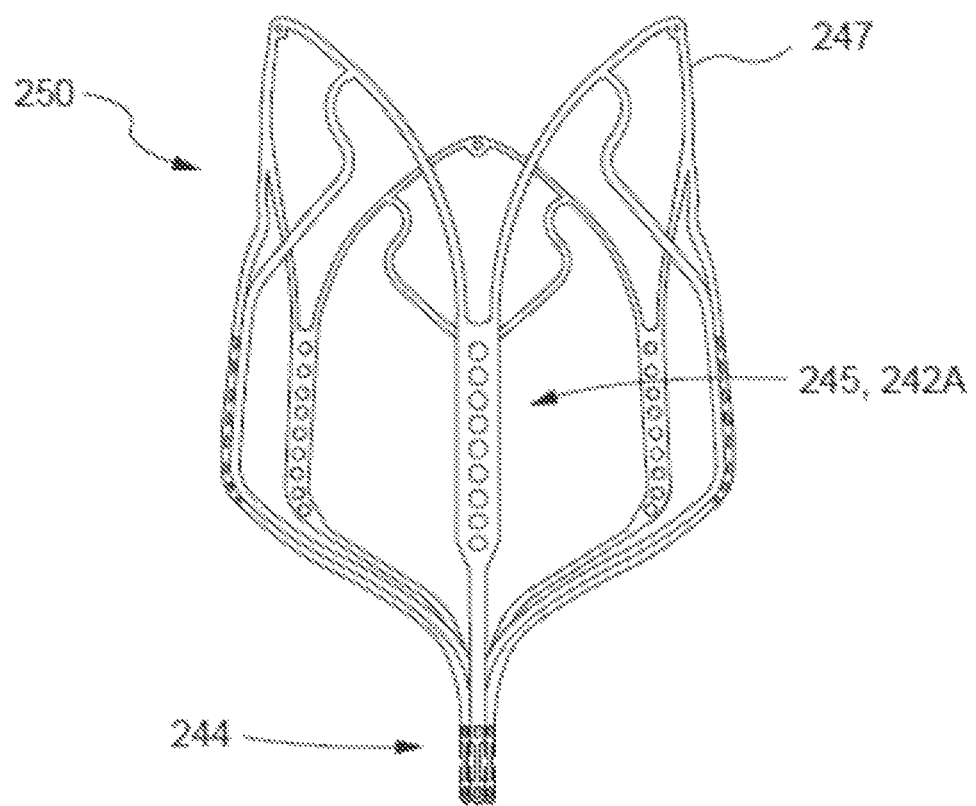
FIGS. 7 and 8 are side and bottom views, respectively, of the inner frame of FIG. 6 in an expanded configuration.
Figure 8:
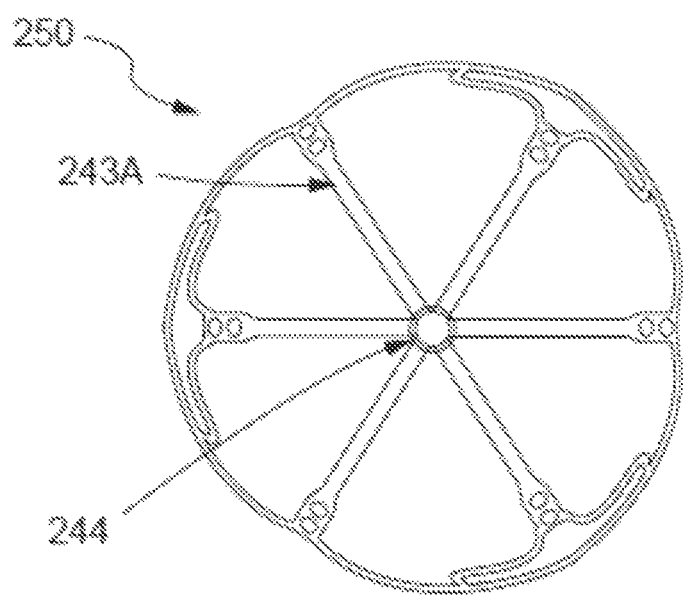

Inner frame 250 is shown in more detail in FIGS. 6-8. Specifically, FIGS. 6-8 show inner frame 250 in an undeformed, initial state (FIG. 6), a side view of the inner frame 250 in an expanded configuration (FIG. 7), and a bottom view of the inner frame 250 in the expanded configuration (FIG. 8), respectively, according to an embodiment.

In this embodiment, inner frame 250 is formed from a laser-cut tube of Nitinol®. Inner frame 250 is illustrated in FIG. 6 in an undeformed, initial state, i.e. as laser-cut, but cut and unrolled into a flat sheet for ease of illustration. Inner frame 250 can be divided into four portions, corresponding to functionally different portions of the inner frame 250 in final form: atrial portion 247, body portion 242, strut portion 243, and tether clamp or connecting portion 244. Strut portion 243 includes six struts, such as strut 243A, which connect body portion 242 to tether connecting portion 244.

Tether connecting portion 244 (also referred to as first end portion of inner frame) includes longitudinal extensions of the struts, connected circumferentially by pairs of opposed, slightly V-shaped connecting members (or "micro-Vs"). Tether connecting portion 244 is configured to be radially collapsed by application of a compressive force, which causes the micro-Vs to become more deeply V-shaped, with the vertices moving closer together longitudinally and the open ends of the V shapes moving closer together circumferentially. Thus, tether connecting portion 244 can be configured to compressively clamp or grip one end of a tether, either connecting directly onto a tether line (e.g. braided filament line) or onto an intermediate structure, such as a polymer or metal piece that is in turn firmly fixed to the tether line.

In contrast to tether connecting portion 244, atrial portion 247 (also referred to as "inner frame free end portion") and body portion 242 are configured to be expanded radially. Strut portion 243 forms a longitudinal connection and radial transition between the expanded body portion and the compressed tether connecting portion 244. Body portion 242 provides an inner frame coupling portion 245 that includes six longitudinal posts, such as post 242A. The inner frame coupling portion 245 can be used to attach leaflets 270 to inner frame 240, and/or can be used to attach inner assembly 240 to outer assembly 210, such as by connecting inner frame 250 to outer frame 220. In the illustrated embodiment, the posts include openings through which connecting members (such as suture filaments and/or wires) can be passed to couple the posts to other structures.

Inner frame 250 is shown in a fully deformed, i.e. the final, deployed configuration, in side view and bottom view in FIGS. 7 and 8, respectively.

Figure 9:
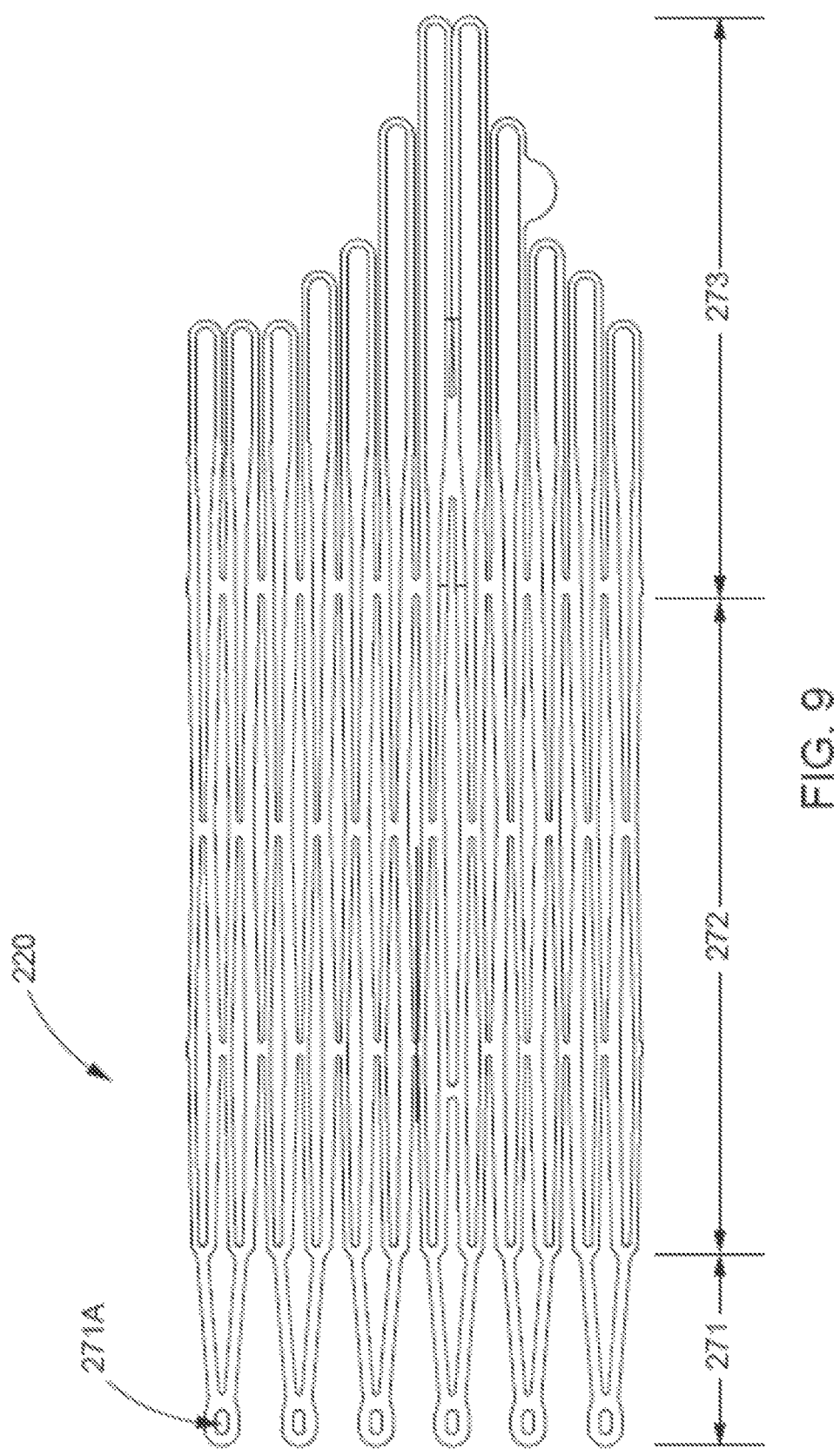
FIG. 9 is an opened and flattened view of the outer frame of the valve of FIGS. 3-5, in an unexpanded configuration.
Figure 10:
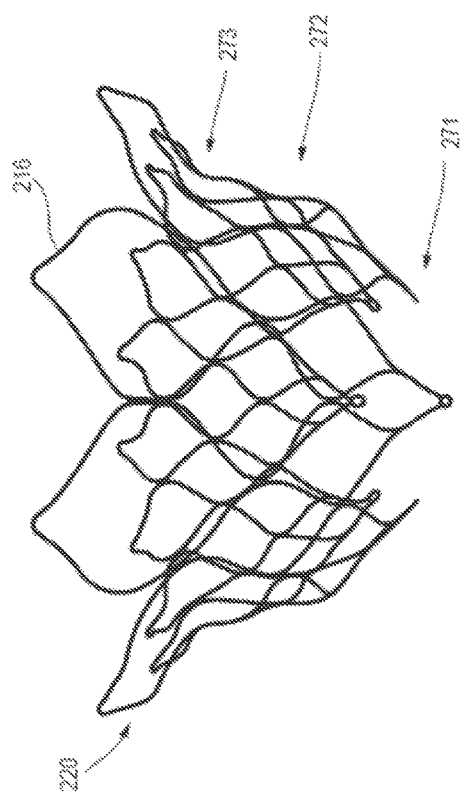
FIGS. 10 and 11 are side and top views, respectively, of the outer frame of FIG. 9 in an expanded configuration.
Figure 11:
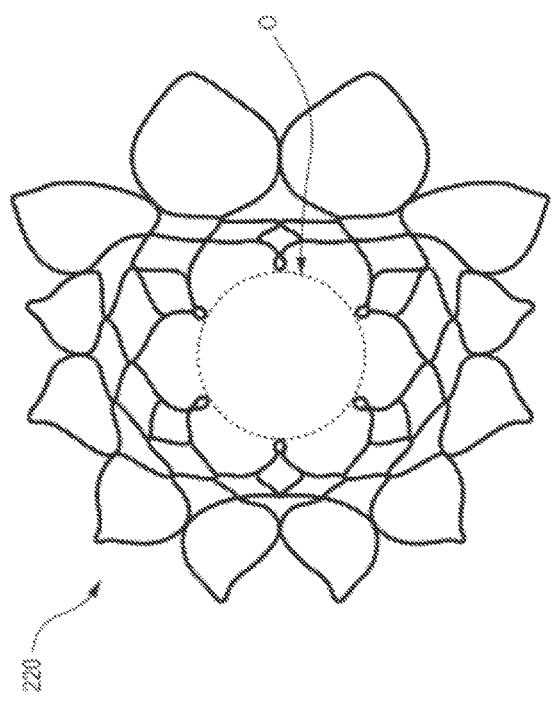

Outer frame 220 of valve 200 is shown in more detail in FIGS. 9-11. In this embodiment, outer frame 220 is also formed from a laser-cut tube of Nitinol®. Outer frame 220 is illustrated in FIG. 9 in an undeformed, initial state, e.g., as laser-cut, but cut and unrolled into a flat sheet for ease of illustration. Outer frame 220 can be divided into an outer frame coupling portion 271, a body portion 272, and a cuff portion 273 (which includes the atrium or free end portion 216), as shown in FIG. 9. Outer frame coupling portion 271 includes multiple openings or apertures, such as 271A, by which outer frame 220 can be coupled to inner frame 250, as discussed in more detail below.

Outer frame 220 is shown in a fully deformed, e.g., the final, deployed configuration, in side view and top view in FIGS. 10 and 11, respectively. As best seen in FIG. 11, the lower end of outer frame coupling portion 271 forms a roughly circular opening (identified by "O" in FIG. 11). The diameter of this opening preferably corresponds approximately to the diameter of body portion 242 of inner frame 250, to facilitate coupling of the two components of valve 200.

Figure 12:
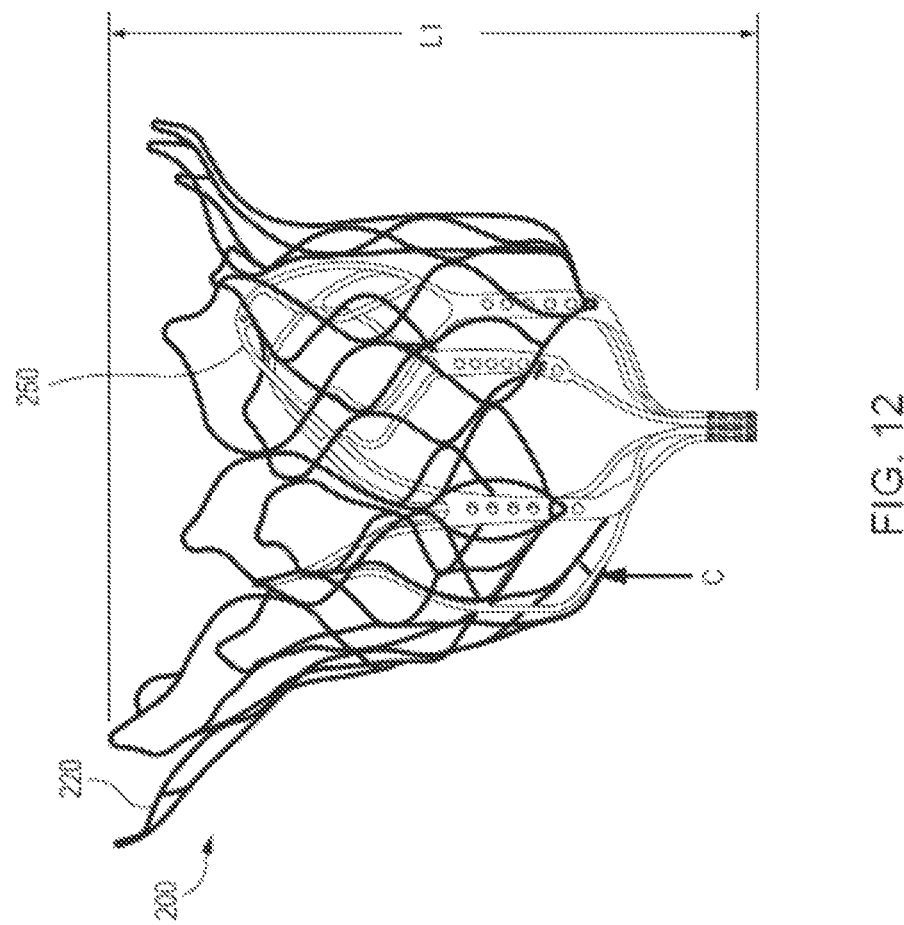
FIGS. 12-14 are side, front, and top views of an assembly of the inner frame of FIGS. 6-8 and the outer frame of FIGS. 9-11.
Figure 13:
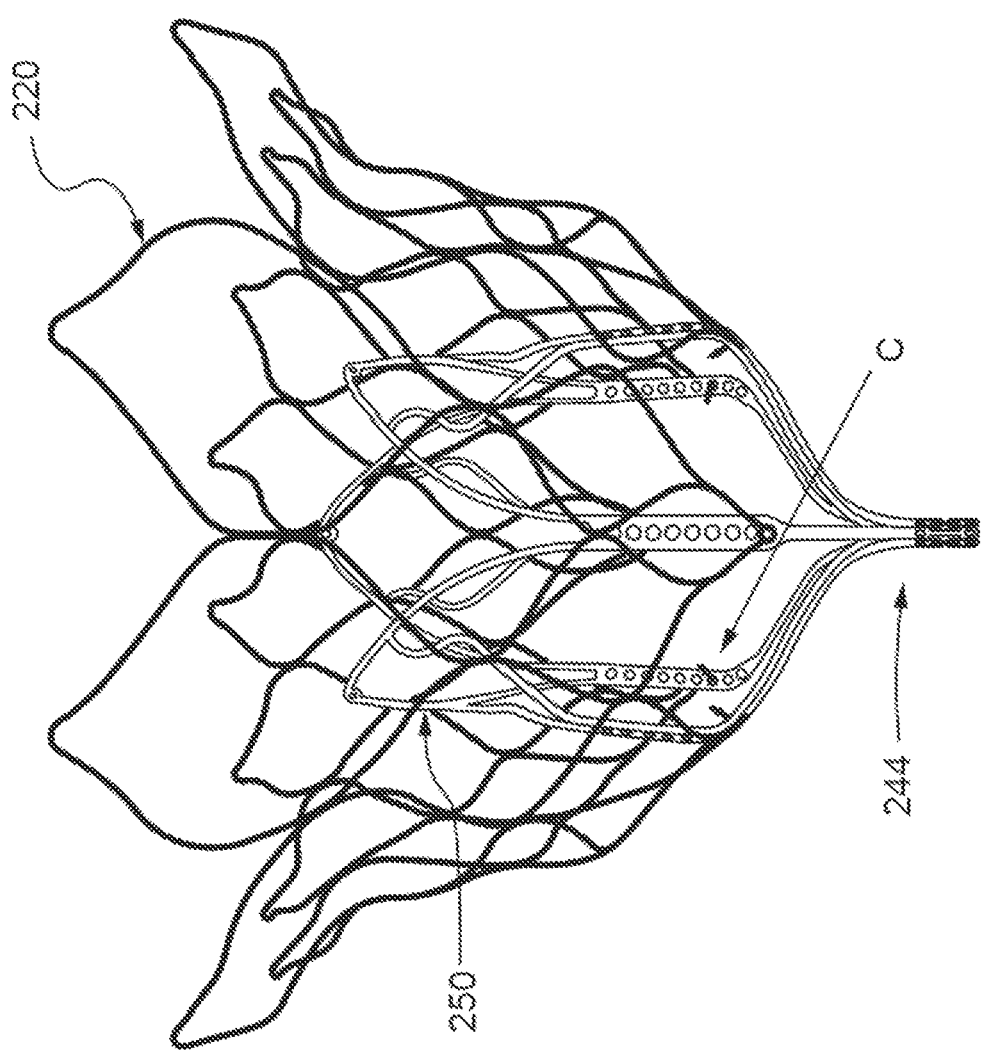
Figure 14:
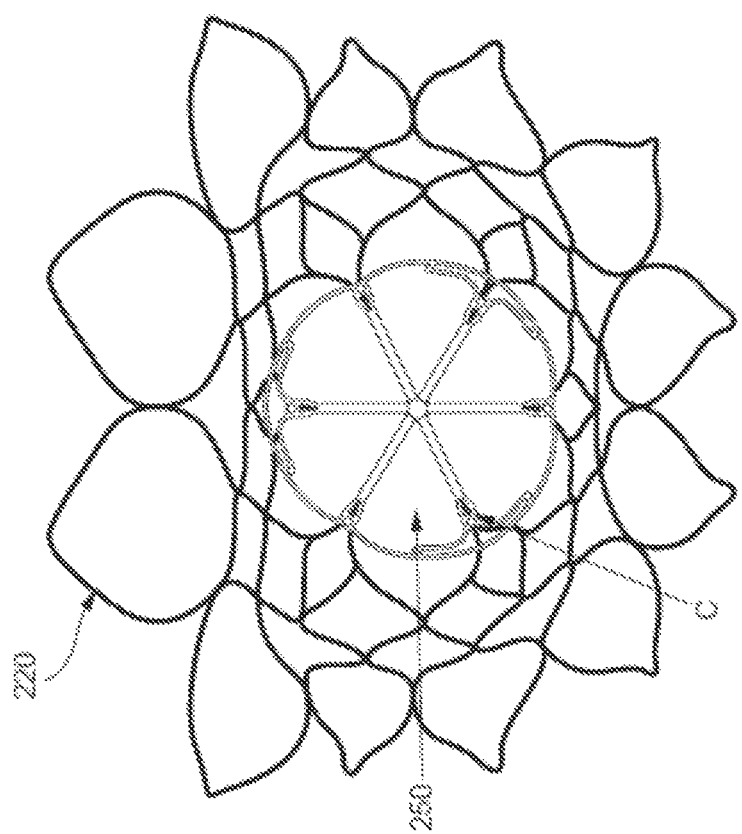

Outer frame 220 and inner frame 250 are shown coupled together in FIGS. 12-14, in front, side, and top views, respectively. The two frames collectively form a structural support for a prosthetic valve such as valve 200. The frames support the valve leaflet structure (e.g., leaflets 270) in the desired relationship to the native valve annulus, support the coverings (e.g., outer covering 230, inner covering 232, outer covering of the inner valve assembly 240) for the two frames to provide a barrier to blood leakage between the atrium and ventricle, and couple to the tether (e.g., tether assembly 290) (by the inner frame 250) to aid in holding the prosthetic valve 200 in place in the native valve annulus by the tether connection to the ventricle wall. The outer frame 220 and the inner frame 250 are connected at six coupling points (representative points are identified as "C"). In this embodiment, the coupling points are implemented with a mechanical fastener, such as a short length of wire, passed through an aperture (such as aperture 271A) in outer frame coupling portion 271 and corresponding openings in inner frame coupling portion 245 (e.g., longitudinal posts, such as post 242A) in body portion 242 of inner frame 250. Inner frame 250 is thus disposed within the outer frame 220 and securely coupled to it.

FIGS. 15-21 illustrate a method of reconfiguring a prosthetic heart valve 300 (e.g., prosthetic mitral valve) prior to inserting the prosthetic heart valve 300 into a delivery sheath 326 (see, e.g., FIGS. 17-21) for delivery into the atrium of the heart. The prosthetic heart valve 300 (also referred to herein as "valve") can be constructed the same as or similar to, and function the same as or similar to the valves 100 and 200 described above. Thus, some details regarding the valve 300 are not described below. It should be understood that for features and functions not specifically discussed, those features and functions can be the same as or similar to the valve 200.

Figure 15:
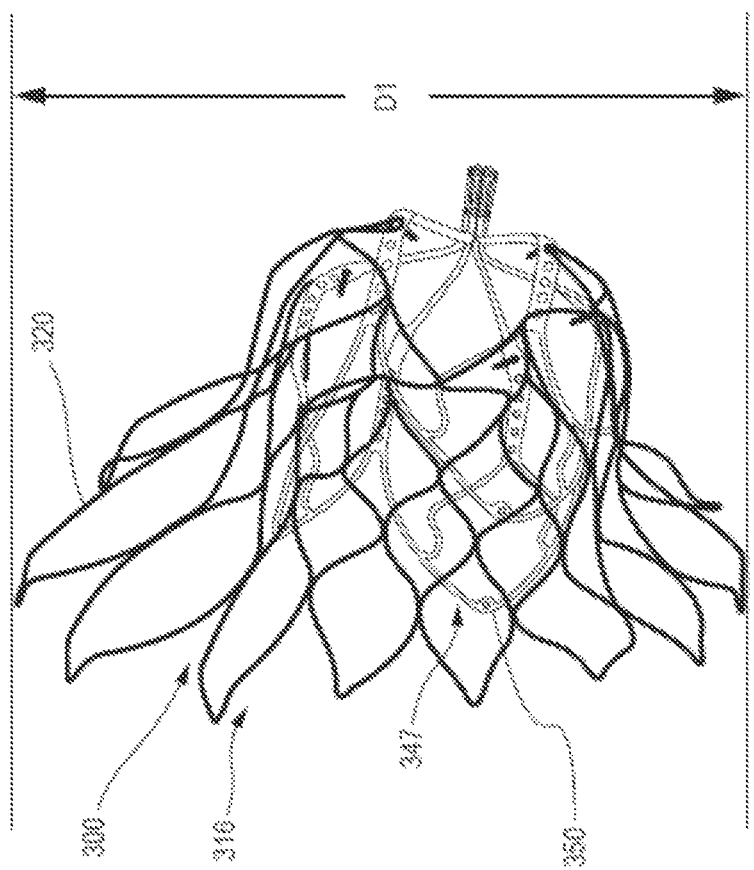
FIG. 15 is a side perspective view of an assembly of an inner frame and an outer frame shown in a biased expanded configuration, according to an embodiment.
Figure 16:
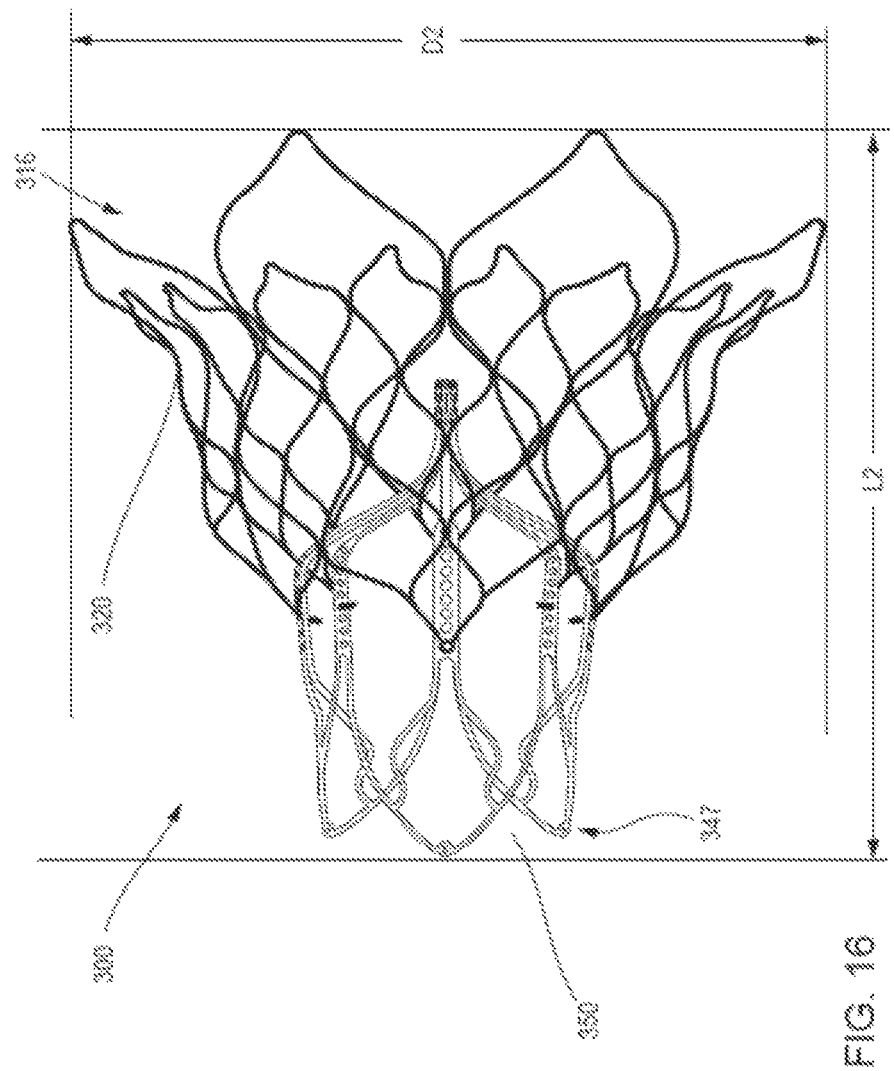
FIG. 16 is a side perspective view of the assembly of FIG. 15 with the outer frame shown inverted.
Figure 17:
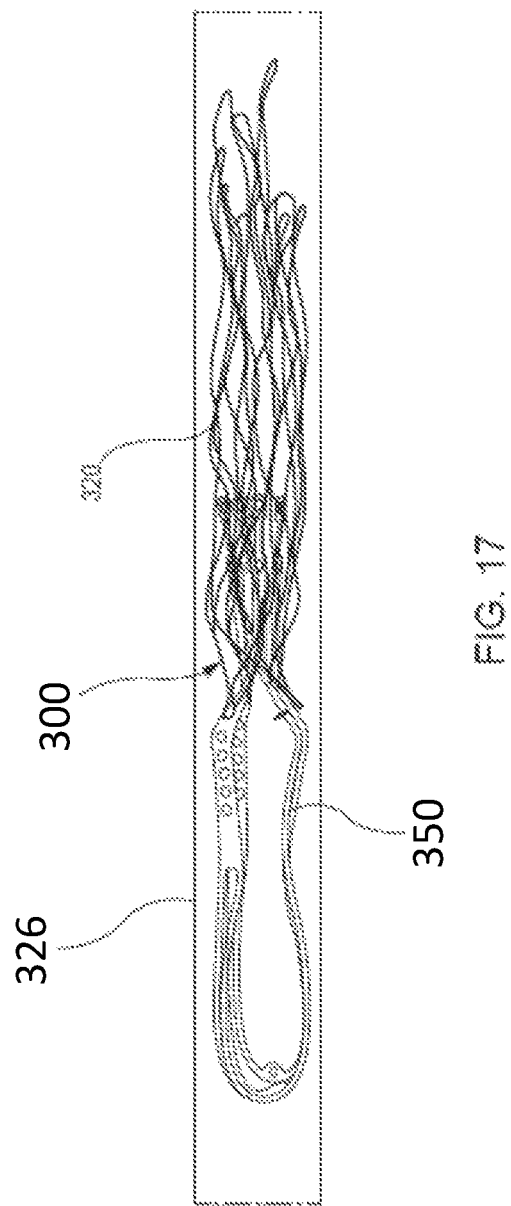
FIG. 17 is side view of the assembly of FIG. 16 shown in a collapsed configuration within a lumen of a delivery sheath.

As shown in FIG. 15, the valve 300 has an outer frame 320 and an inner frame 350. As discussed above for valves 100 and 200, the outer frame 320 and the inner frame 350 of valve 300 can each be formed with a shape-memory material and have a biased expanded configuration. The outer frame 320 and the inner frame 350 can be moved to a collapsed configuration for delivery of the valve 300 to the heart. In this example method of preparing the valve 300 for delivery to the heart, the outer frame 320 of the valve 300 is first disposed in a prolapsed or inverted configuration as shown in FIG. 16. Specifically, the elastic or superelastic structure of outer frame 320 of valve 300 allows the outer frame 320 to be disposed in the prolapsed or inverted configuration prior to the valve 300 being inserted into the lumen of the delivery sheath 326. As shown in FIG. 16, to dispose the outer frame 320 in the inverted configuration, the outer frame 320 is folded or inverted distally (to the right in FIG. 16) such that an open free end 316 of the outer frame 320 is pointed away from an open free end 347 of the inner frame 350. As described above for valve 100, in this inverted configuration, the overall outer perimeter or outer diameter of the valve 300 is reduced and the overall length is increased. For example, the diameter D1 shown in FIG. 15 is greater than the diameter D2 shown in FIG. 16, and the length L1 (shown in FIG. 12 for valve 200) is less than the length L2 shown in FIG. 16 for valve 300. With the outer frame 320 in the inverted configuration relative to the inner frame 350, the valve 300 can be placed within a lumen of a delivery sheath 326 as shown in FIG. 17 for delivery of the valve 300 to the left atrium of the heart. By disposing the outer frame 320 in the inverted configuration relative to the inner frame 350, the valve 300 can be collapsed into a smaller overall diameter, i.e. when placed in a smaller diameter delivery sheath, than would be possible if the valve 300 in the configuration shown in FIG. 15 were collapsed radially without being inverted. This is because in the configuration shown in FIG. 15, the two frames are concentric or nested, and thus the outer frame 320 must be collapsed around the inner frame 350, whereas in the configuration shown in FIG. 16, the two frames are substantially coaxial but not concentric or nested. Thus, in the configuration shown in FIG. 16, the outer frame 320 can be collapsed without the need to accommodate the inner frame 350 inside of it. In other words, with the inner frame 350 disposed mostly inside or nested within the outer frame 320, the layers or bulk of the frame structures cannot be compressed to as small a diameter. In addition, if the frames are nested, the structure is less flexible, and therefore, more force is needed to bend the valve, e.g. to pass through tortuous vasculature or to make tight turn in the left atrium after passing through the atrial septum to be properly oriented for insertion into the mitral valve annulus.

Figure 22:
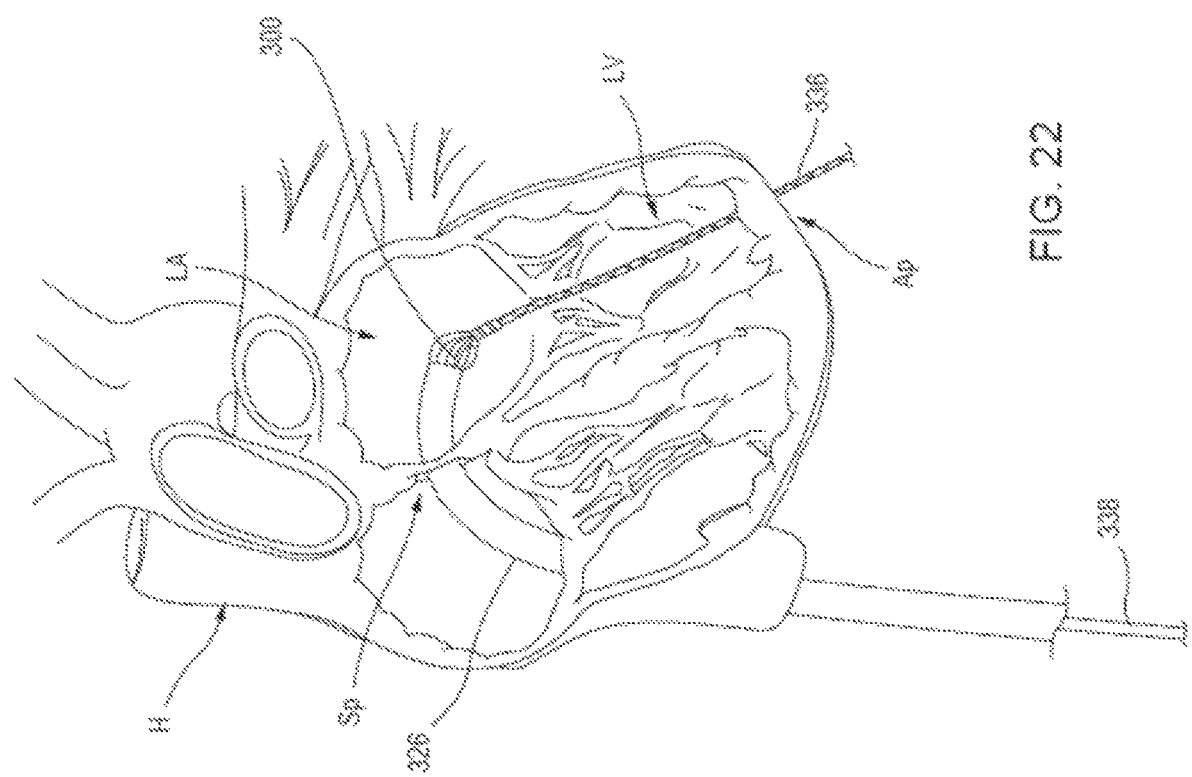
FIGS. 22-24 illustrate steps of a portion of a method to deliver the prosthetic valve of FIGS. 15-21 to an atrium of a heart and within the native mitral annulus.
Figure 23:
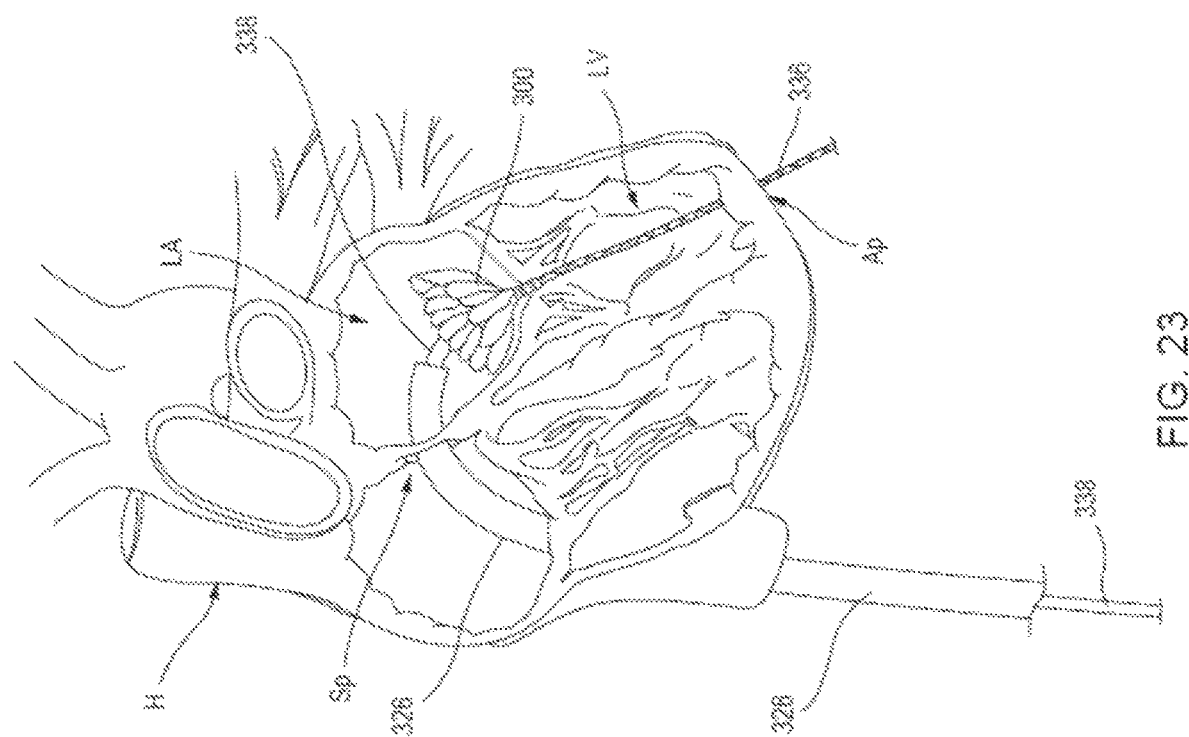
Figure 24:
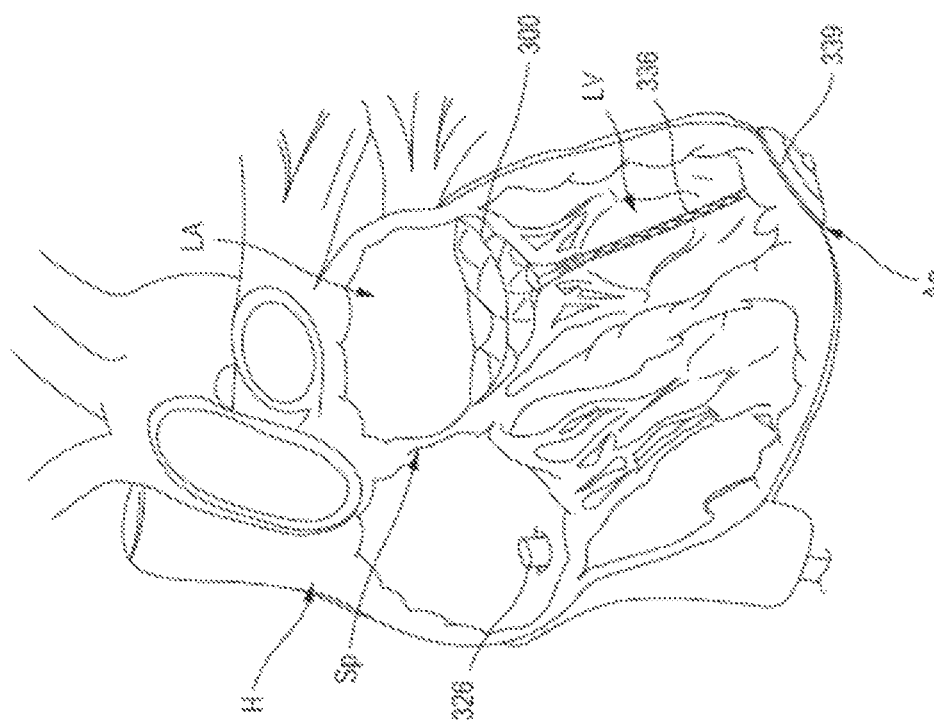

FIGS. 22-24 illustrate a portion of a procedure to deliver the valve 300 to the heart. In this embodiment, the valve 300 is shown being delivered via a transfemoral delivery approach as described, for example, in the '305 PCT application incorporated by reference above. The delivery sheath 326, with the valve 300 disposed within a lumen of the delivery sheath 326 and in an inverted configuration as shown in FIG. 17, can be inserted into a femoral puncture, through the femoral vein, through the inferior vena cava, into the right atrium, through the septum Sp and into the left atrium LA of the heart. With the distal end portion of the delivery sheath 326 disposed within the left atrium of the heart, the valve 300 can be deployed outside a distal end of the delivery sheath 326. For example, in some embodiments, a pusher device 338 (shown in FIG. 23) can be used to move or push the valve 300 out the distal end of the delivery sheath 326. As shown in FIGS. 22-24, a tether 336 can be attached to the valve 300, and extend though the mitral annulus, through the left ventricle LV, and out a puncture site at the apex Ap. In some embodiments, the valve 300 can be moved out of the delivery sheath 326 by pulling proximally on the tether 336. In some embodiments, the valve 300 can be deployed by pushing with the pusher device and pulling with the tether.

Figure 18:
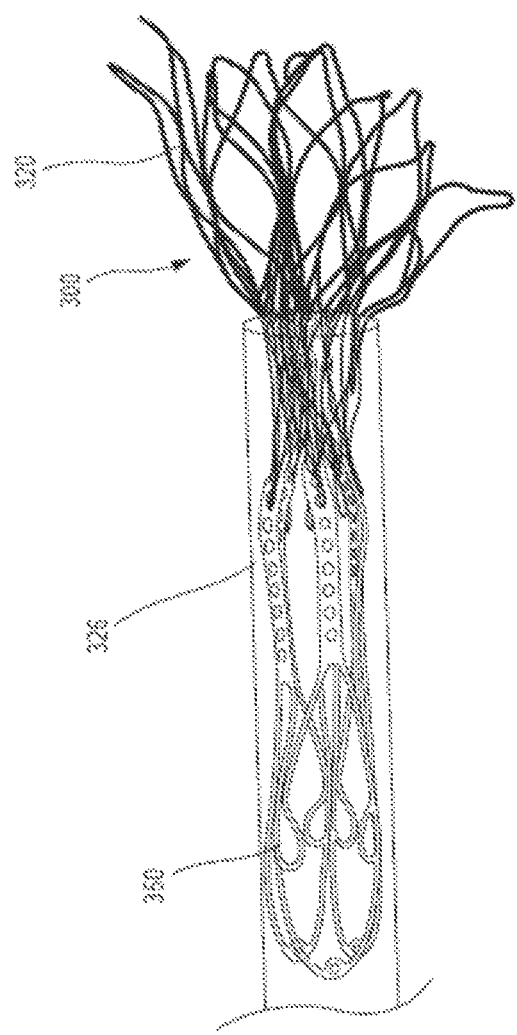
FIG. 18 is a side view of the assembly of FIG. 17 shown in a first partially deployed configuration.
Figure 19:
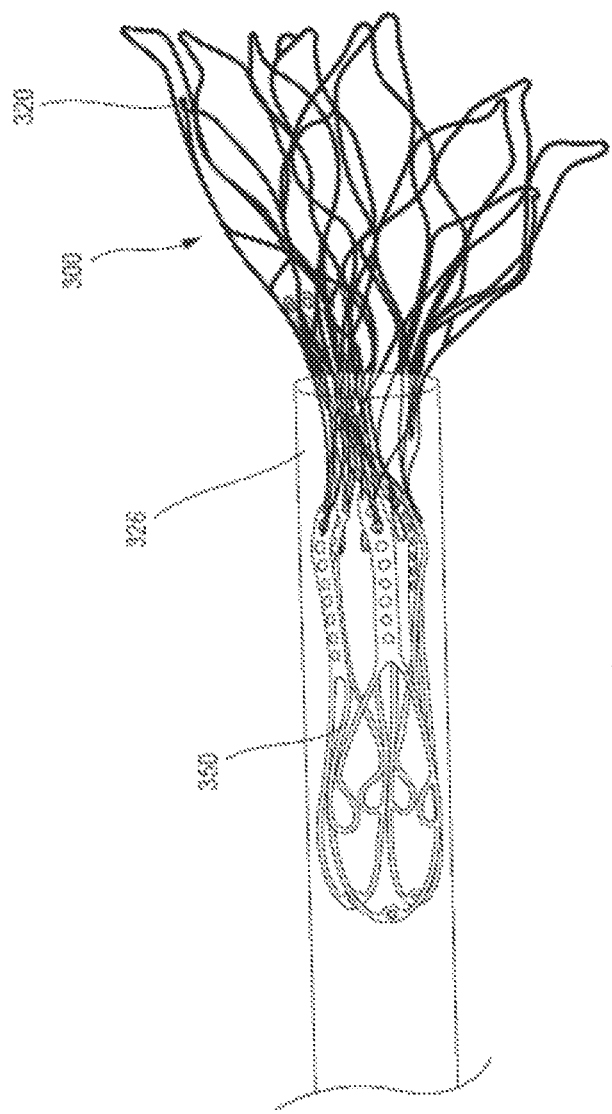
FIG. 19 is a side view of the assembly of FIG. 17 shown in a second partially deployed configuration.
Figure 20:
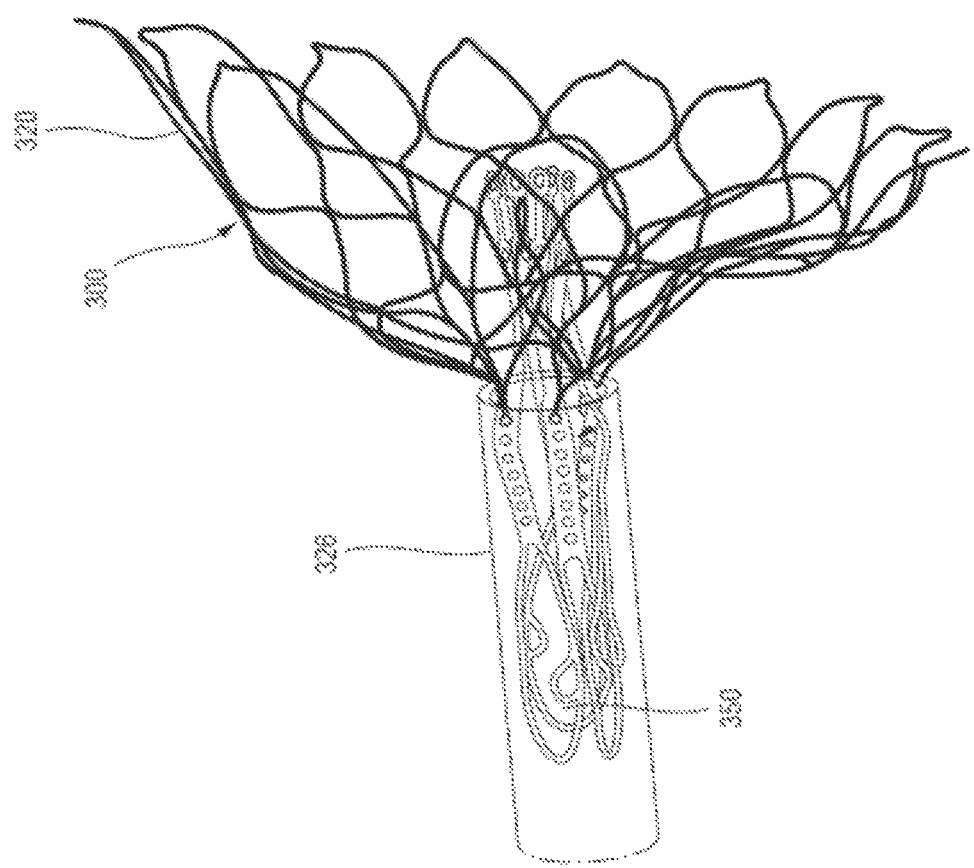
FIG. 20 is a side view of the assembly of FIG. 17 shown in a third partially deployed configuration in which the inverted outer frame is substantially deployed outside of the delivery sheath.
Figure 21:
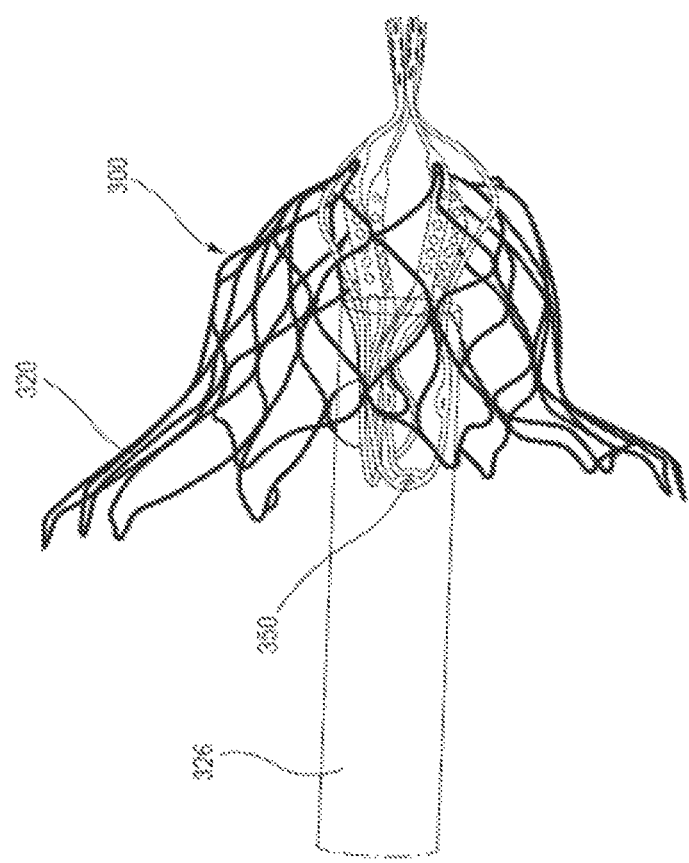
FIG. 21 is a side view of the assembly of FIG. 17 shown in a fourth partially deployed configuration in which the outer frame has reverted and assumed a biased expanded configuration.

As the valve 300 exits the lumen of the delivery sheath 326, the outer frame assembly 310 exits first in its inverted configuration as shown in the progression of FIGS. 18-20 (see also FIG. 22). After the outer frame assembly 310 is fully outside of the lumen of the delivery sheath 326, the outer frame 320 can revert to its expanded or deployed configuration as shown in FIGS. 21, 23 and 24. In some embodiments, the outer frame 320 can revert automatically after fully exiting the lumen of the delivery sheath due to its shape-memory properties. In some embodiments, a component of the delivery sheath or another device can be used to aid in the reversion of the outer frame assembly 310. In some embodiments, the pusher device 338 and/or the tether 336 can be used to aid in the reversion of the outer frame assembly 310. The valve 300 can continue to be deployed until the inner frame 350 is fully deployed with the left atrium and the valve 300 is in the expanded or deployed configuration (as shown, e.g., in FIGS. 15 and 24). The valve 300 and the tether 336 can then be secured to the apex of the heart with an epicardial pad device 339 as shown in FIG. 24 and as described in more detail in the '305 PCT application.

Figure 25A:
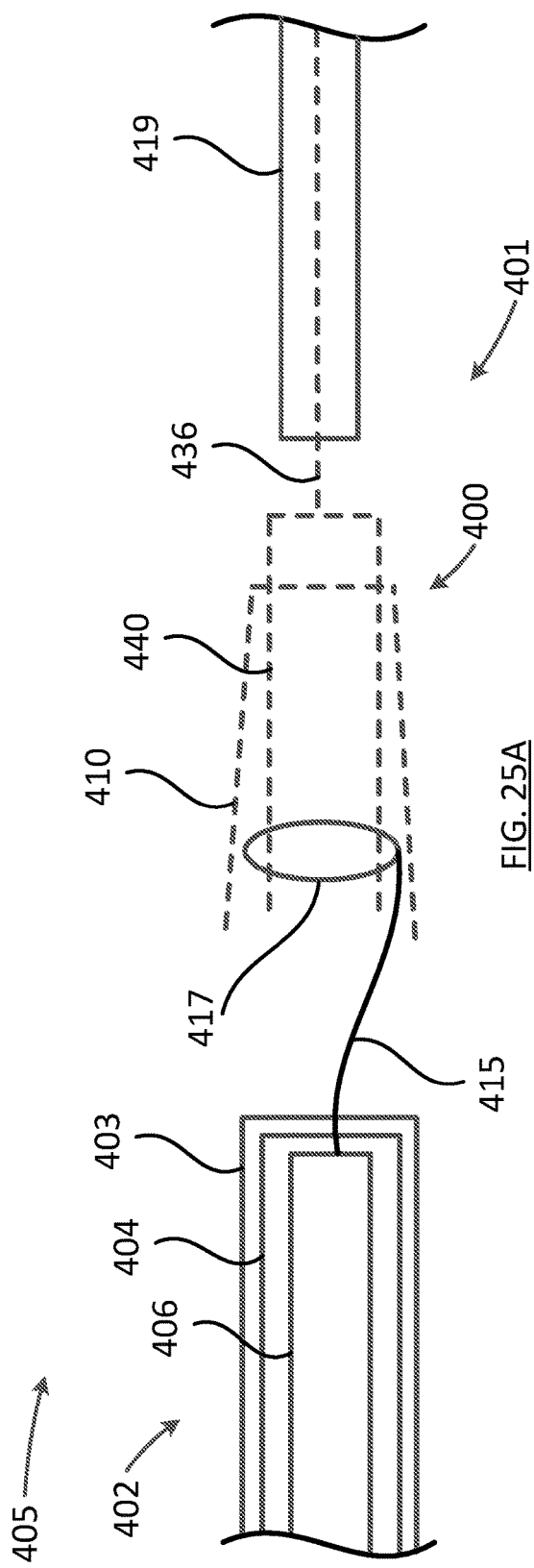
FIG. 25A is a schematic illustration of a prosthetic mitral valve retrieval system engaged with a prosthetic valve in a first configuration, according to an embodiment.
Figure 25B:
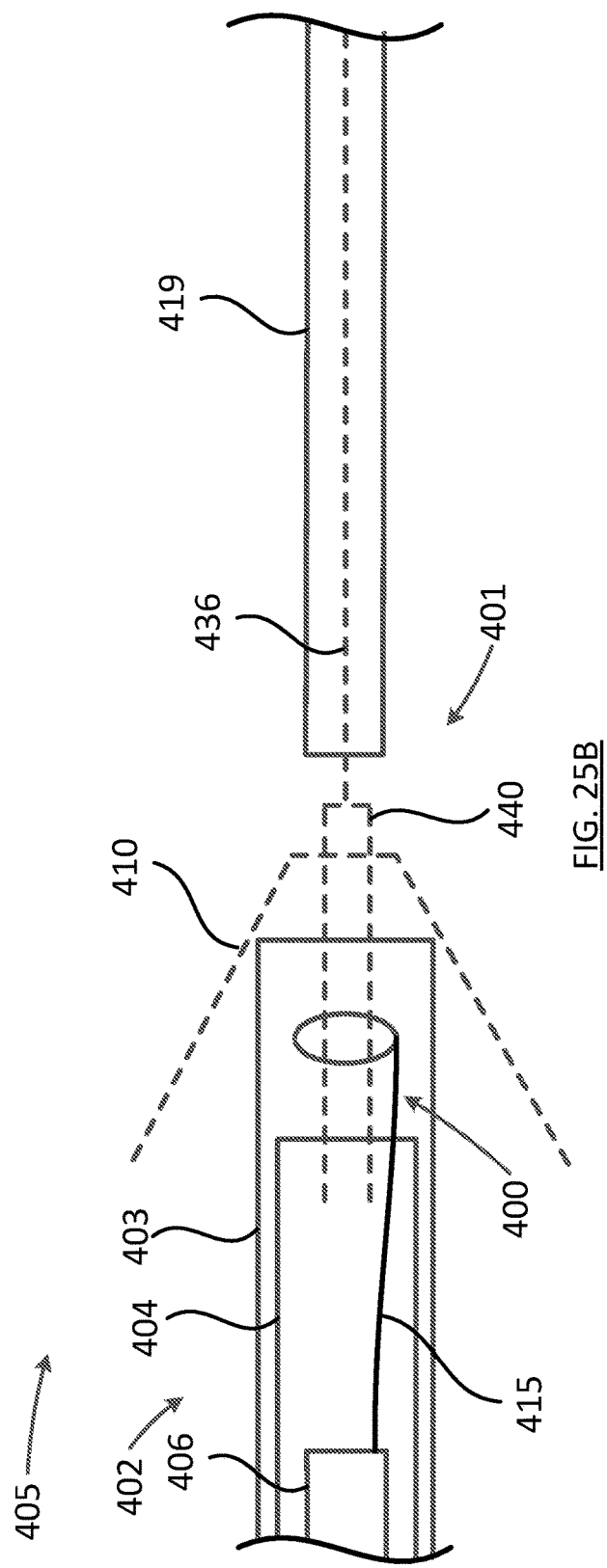
FIG. 25B is a schematic illustration of the prosthetic mitral valve retrieval system of FIG. 25A with the prosthetic valve in a second configuration in which an inner frame of the prosthetic valve is partially disposed within the retrieval system.

FIGS. 25A-25C are schematic illustrations of a retrieval system 405 during various stages of a procedure to engage, capture, and remove a prosthetic heart valve after it has been deployed within a heart (not shown in FIGS. 25A-25C). As shown in FIG. 25A, the retrieval system 405 can include a retrieval assembly 402. The retrieval assembly 402 can include an outer catheter 403, a middle catheter 404, a snare catheter 406, and a snare member 415. The snare member 415 can be movably disposed within a lumen of the snare catheter 406 and the snare catheter 406 can be movably disposed within a lumen of the middle catheter 404. Similarly, the middle catheter 404 can be movably disposed within a lumen of the outer catheter 403. The outer catheter 403 can have a rigid distal tip. Optionally, in some embodiments, the retrieval system 405 can also include an apical positioning catheter 419.

The retrieval system 405 can engage with a valve assembly (e.g., a prosthetic heart valve) such that the retrieval system 405 can be used to control the position and configuration of the valve assembly. In particular, as shown in FIG. 25A, the retrieval system 405 can engage with and retrieve a previously-implanted valve assembly 401 from, for example, a mitral annulus. The valve assembly 401 can include a valve 400 and a tether 436. The valve 400 and the tether 436 can be constructed the same as or similar to, and function the same as or similar to, any of the valves and tethers described herein and in the '305 PCT Application incorporated by reference above. For example, the valve 400 can include an inner frame 440 and an outer frame 410. Additionally, in some embodiments, the inner frame 440 can include a body portion and a tether connecting portion. The tether 436 can be coupled to the inner frame 440 via the tether connecting portion. A strut portion of the inner frame 440 can connect the tether connecting portion to the body portion. The outer frame 410 and the inner frame 440 can be formed with a shape-memory material. As a result, the outer frame 410 can be movably coupled to the inner frame 440 such that the valve 400 can be moved between a biased expanded or deployed configuration, an inverted configuration, and a collapsed or compressed configuration. The expanded configuration allows the valve assembly 401 to function when implanted within the heart. The valve 400 can be moved to the inverted configuration and/or the compressed or collapsed configuration for delivery of the valve assembly 401 to, or retrieval of the valve assembly 401 from, the heart of a patient.

More specifically, for delivery of the valve assembly 401 to the heart via a delivery sheath and/or retrieval of the valve assembly 401 from the heart via the retrieval assembly 402, the outer frame 410 can be moved to a prolapsed or inverted configuration relative to the inner frame 440 by folding or distally inverting the outer frame 410 via, for example, coupling joints. Prior to being inverted, the outer frame 410 can be in a first position relative to the inner frame 440 in which an open or free end portion is disposed in the same direction as a free end portion of the inner frame 440, as shown in FIG. 25A. When the outer frame 410 is moved to an inverted configuration, the free end portion of the outer frame 410 is disposed in an opposite direction as the free end portion of the inner frame 440, as shown in FIG. 25C.

When in the inverted configuration, an overall length of the valve 400 is increased, but a length of the inner frame 440 and a length of the outer frame 410 remain the same (or substantially the same). In addition, in some instances, depending on the specific configuration of the outer frame 410, an overall outer perimeter or outer diameter of the valve 400 can be smaller when the valve 400 is in the inverted configuration. For example, with the valve 400 in the inverted configuration, the valve 400 can be placed within a lumen of a delivery sheath or the retrieval assembly 402 for delivery to or retrieval from, respectively, the left atrium of the heart. Before inserting the valve 400 into a lumen of the delivery sheath or the retrieval assembly 402, the valve 400 can first be moved to the inverted configuration and then to a collapsed or compressed configuration within the lumen of the delivery sheath or retrieval assembly 402 in which the outer diameter or outer perimeter of the valve 400 is reduced. Because the valve 400 is in the inverted configuration, the valve 400 can be placed within a smaller delivery sheath or retrieval assembly 402 than would be possible if the valve 400 were merely collapsed radially. This is because when the valve 400 is in the biased expanded configuration, the inner frame 440 is nested within an interior of the outer frame 410, and thus the outer frame 410 must be collapsed around the inner frame 440 if merely collapsed radially. Whereas, in the inverted configuration, the inner frame 440 and the outer frame 410 are arranged axially with respect to each other (i.e., the inner frame is not nested within the outer frame 410), such that the outer frame 410 can be collapsed without needing to accommodate all of the structure of the inner frame 440 inside the outer frame 410. In other words, with the inner frame 440 disposed mostly inside or nested within the outer frame 410, the layers or bulk of the frame structures cannot be compressed to as small a diameter. In addition, the valve 400 is more flexible in the inverted configuration. In other words, less force is required to bend the valve 400 for the valve 400 to pass through tortuous vasculature or to make a tight turn (e.g., into the left atrium after passing through the atrial septum to be properly oriented for insertion into the mitral valve annulus or, for retrieval, out of the mitral valve annulus to be properly oriented to pass through the atrial septum). Conversely, if the outer frame 410 and the inner frame 440 are nested, the valve 400 is less flexible and more force is needed to bend the valve 400.

The snare member 415 can be any suitable shape and can include an engagement portion 417. The engagement portion 417 can be extendable from an undeployed configuration (not shown) when disposed within the lumen of the snare catheter 419 to a deployed configuration when disposed outside of the snare catheter 419, as shown in FIG. 25A. In some embodiments, the undeployed configuration of the engagement portion 417 can be a collapsed configuration where the engagement portion 417 is bent, squeezed, or otherwise reduced in diameter to fit into the lumen of the snare catheter 419. The engagement portion 417 can be formed with a shape-memory material and have a biased expanded or deployed configuration such that the engagement portion 417 automatically expands as it is moved out of the lumen of the snare catheter 419.

The engagement portion 417 of the snare member 415 is shaped and sized such that, in the expanded or deployed configuration, the engagement portion 417 can surround and engage with a portion of the inner frame 440 of the valve 400. As shown in FIG. 25A, as the engagement portion 417 is pushed or moved outside the distal end of the snare catheter 406, the engagement portion 417 can transition to the expanded configuration. In the expanded configuration, the engagement portion 417 can be positioned relative to the inner frame 440 of the valve 400 such that the snare member 415 engages with the inner frame 440. For example, the engagement portion 417 can be positioned such that the engagement portion 417 surrounds the inner frame 440. When the engagement portion 417 is positioned around the inner frame 440, the engagement portion 417 can be manipulated such that the engagement portion 417 grasps the inner frame 440 (e.g., the engagement portion 417 can be reduced in diameter to securely engage with the inner frame 440). When the engagement portion 417 is securely engaged with the inner frame 440, the engagement portion 417 can be further manipulated to control the position of the inner frame 440. Additionally, the engagement portion 417 can apply a compressive force to partially collapse the inner frame 440, reducing the outer diameter of the inner frame 440 such that the inner frame 440 can be retracted into the middle catheter 404 and/or the outer catheter 403 via proximal movement of the snare member 415 as shown in FIG. 25B.

In some embodiments, as shown in FIGS. 25A-25C, the engagement portion 417 of the snare member 415 can be formed as a loop or lariat. In such embodiments, the engagement portion 417 can have a biased expanded configuration such that the engagement portion 417 automatically transitions to a loop configuration upon being pushed or otherwise moved out of the distal end of the snare catheter 406. The engagement portion 417 can be reduced in diameter to capture and/or compress a portion of the valve 400. For example, the snare member 415 can be disposed within a lumen of a pusher tube (not shown). The pusher tube can be translated distally along the snare member 415 to reduce the diameter of the engagement portion 417 such that the engagement portion 417 applies an engagement and/or compressive force on the inner frame 440.

Although the snare member 415 is shown in FIGS. 25A-25C as including a single loop or lariat, in other embodiments, the engagement portion 417 or, alternatively, the entire snare member 415 can be shaped as a coil and sized such that, in the expanded or deployed configuration, the engagement portion 417 can surround the inner frame 440 and engage with the inner frame 440. In such an embodiment, the engagement portion 417 can be formed with a shape-memory material and the coil shape can be elongated in a delivery configuration inside the snare catheter 406. The coil shape can include multiple loops having the same or different diameters when expanded. As the engagement portion 417 is pushed outside the distal end of the snare catheter 406, the portion of the engagement portion 417 outside of the distal end of the snare catheter 406 can transition to an expanded coil configuration. For example, in some embodiments, as a length of the engagement portion 417 is pushed outside of the distal end of the snare catheter 406, the diameter of the engagement portion 417 can enlarge such that the inner frame 440 can be received within the coil shape formed by the engagement portion 417. When the engagement portion 417 is a sufficient size to receive the inner frame 440, the coil can be moved further distally to surround the inner frame 440. Then, the snare catheter 406 can be moved distally relative to the snare member 415 such that the engagement portion 417 is partially withdrawn into a lumen of the snare member 415. As a result, the diameter of the engagement portion 417 can decrease, causing the engagement portion 417 to engage with and apply a compressive force to the inner frame 440. Thus, the snare member 415 can be used to control the position and/or diameter of the inner frame 440.

As described above and as shown in FIG. 25B, the inner frame 440 of the valve 400 can be retracted into the middle catheter 404 and/or the outer catheter 403 via a proximal movement of the snare member 415, while the engagement portion 417 applies a compressive force to the inner frame 440. The snare member 415 can be pulled further proximally such that the outer frame 410 is pulled into abutting contact with the rigid distal tip of the distal end of the outer catheter 403. As the snare member 415 pulls the inner frame 440 further proximally relative to the outer catheter 403, the outer frame 410 can be moved (i.e., flipped) into the inverted configuration as a result of the force applied by the rigid distal tip of the outer catheter 403 against the outer frame 410, as shown in FIG. 25C. The snare member 415 can continue to be retracted until the outer frame 410 is fully within the outer catheter 403.

In some embodiments, the apical positioning catheter 419 (also referred to herein as "the positioning catheter 419") can be used to position and/or orient the valve assembly 401 for repositioning and/or retrieval of the valve assembly 401. The positioning catheter 419 can be inserted through the apex of the heart and translated along the tether 436 (i.e., the tether 436 can be threaded through a lumen of the positioning catheter 419). The positioning catheter 419 can be pushed into abutting contact with the valve 400 such that a portion of the valve 400 is disposed within a lumen of the positioning catheter 419. The positioning catheter 419 can then be used to help move the valve 400 toward the retrieval assembly 402 or reposition the valve 400. In some embodiments, the positioning catheter 419 can engage with the valve 400 such that the positioning catheter 419 can control the movement of the valve 400 in some or all directions (e.g., distal, proximal, rotational, and/or lateral movement). For example, in some embodiments, the positioning catheter 419 can be moved towards the valve 400 along the tether 436 while the tether 436 is simultaneously pulled taut away from the valve 400 such that the valve 400 is positioned in abutting contact with the distal end of the positioning catheter 419. With the tether 436 continuing to be held taut, the positioning catheter 419 can then be used to control the position of the valve 400. In some embodiments, the positioning catheter 419 can be used to aid in transitioning the outer frame 410 between the unbiased, expanded configuration and the inverted configuration. For example, in some embodiments, the positioning catheter 419 can be pushed towards the valve 400 along the tether 436 while the tether 436 is simultaneously pulled taut away from the valve 400 such that the distal end of the positioning catheter 419 can compress or partially collapse a portion of the valve 400, such as, for example, the strut portion. The positioning catheter 419 can then assist in pushing the valve 400 toward and/or into the retrieval assembly 402, assisting in providing the force required to transition the valve 400 to the inverted configuration.

In use, the valve assembly 401 can be delivered to a heart as described above (e.g., with respect to FIGS. 22-24) and as described in the '305 PCT Application. For example, the valve assembly 401 can be placed in the distal end of a delivery sheath in the inverted configuration and the delivery sheath can be introduced through a femoral vein puncture and extended through the femoral vein, through the inferior vena cava, into the right atrium, through a trans-septal puncture of the septum of the heart, and into the left atrium or left ventricle of the heart. With the distal end portion of the delivery sheath disposed within the left atrium or left ventricle of the heart, the valve 400 can be deployed outside a distal end of the delivery sheath. For example, in some embodiments, a pusher device can be used to move or push the valve 400 out of the distal end of the delivery sheath. In some embodiments, the tether 436 can extend through the mitral annulus, through the left ventricle, and out of a puncture site at the apex of the heart. In such embodiments, the valve 400 can be moved out of the delivery sheath by pulling proximally on the tether 436. In some embodiments, the valve 400 can be deployed by pushing with the pusher device and pulling the tether 436. As the valve 400 exits the lumen of the delivery sheath, the outer frame 410 exits first in the inverted configuration. After the outer frame 410 is fully outside of the lumen of the delivery sheath, the outer frame 410 can revert to its expanded or deployed configuration. In some embodiments, the outer frame 410 can revert automatically after fully exiting the lumen of the delivery sheath due to its shape-memory properties. In some embodiments, a component of the delivery sheath or another device can be used to aid in the reversion of the outer frame 410. In some embodiments, the pusher device and/or the tether 436 can be used to aid in reversion of the outer frame 410. The valve 400 can continue to be deployed until the inner frame 440 is fully deployed within the left atrium and the valve 400 is in the expanded or deployed configuration. The valve 400 can then be securely implanted in the mitral annulus. Additionally, the tether 436 of the valve assembly 401 can then be secured to the apex of the heart with an epicardial pad device, similarly as shown and described with reference to FIG. 24 above. The delivery sheath and any other delivery instruments can then be removed.

With the valve assembly 401 in the deployed configuration within the mitral annulus, the retrieval system 405 can be used to reposition and/or retrieve the valve assembly 401. In some embodiments, the retrieval assembly 402 can approach the left atrium of the heart transfemorally along the transfemoral trans-septal route (i.e., the same path described above for the delivery of the valve assembly 401). In other words, the outer catheter 403, middle catheter 404, and snare catheter 406 of the retrieval assembly 402 can be introduced through a femoral vein puncture and extended through the femoral vein, through the inferior vena cava, into the right atrium, through a trans-septal puncture of the septum of the heart, and into the left atrium of the heart. In other embodiments, the retrieval assembly 402 can approach the valve assembly 401 transatrially, transjugularly, or along any other suitable path. Additionally, in embodiments in which the tether 436 has been secured to the apex of the heart via an epicardial pad device, the tether 436 can be separated from the epicardial pad device through any suitable means.

As described above, the valve 400 can be transitioned to the inverted configuration before being moved into the retrieval assembly 402 so that the valve 400 can fit within a smaller diameter retrieval assembly 402 and so that the retrieval assembly 402 and valve 400 can bend more easily when being maneuvered through the body. To transition the valve 400 to the inverted configuration, once the distal end of the retrieval assembly 402 is within the left atrium of the heart, the snare member 415 can be extended outside of the distal end of the snare catheter 406. As the snare member 415 is pushed out of the distal end of the snare catheter 406, the engagement portion 417 of the snare member 415 can transition from the undeployed configuration to the deployed configuration. With the engagement portion 417 in the deployed configuration, the snare member 415 can be moved toward the valve 400 such that the engagement portion 417 surrounds the inner frame 440, as shown in FIG. 25A. The engagement portion 417 can then be manipulated such that the engagement portion 417 grasps the inner frame 440 (e.g., the engagement portion 417 can be reduced in diameter to securely engage with the inner frame 440). When the engagement portion 417 is securely engaged with the inner frame 440, the engagement portion 417 can be further manipulated to apply a compressive force to reduce the diameter of the inner frame 440 to a diameter sufficiently small to fit within the middle catheter 404.

While compressing the inner frame 440, the snare member 415 can be retracted proximally relative to the snare catheter 406 and/or the snare catheter 406 can be retracted proximally relative to the middle catheter 404. As a result, at least a portion of the inner frame 440 can be pulled into a lumen of the middle catheter 404, as shown in FIG. 25B. The snare member 415, snare catheter 406, and middle catheter 404 can then be pulled proximally relative to the outer catheter 403 such that the outer frame 410 transitions to the inverted configuration. More specifically, the proximal movement of the inner frame 440 can cause the outer frame 410 to be pulled against the rigid tip of the distal end of the outer catheter 403 as shown in FIG. 25B. As the inner frame 440 is pulled further proximally, the rigid tip of the outer catheter 403 can force the outer frame 410 to flip into the inverted configuration, as shown in FIG. 25C. The snare member 415, snare catheter 406, and middle catheter 404 can then continue to be retracted until the outer frame 410 is fully within the outer catheter 403.

Optionally, the positioning catheter 419 can be used to aid in positioning and orienting the valve assembly 401 for repositioning and/or retrieval. In such embodiments, as shown in FIG. 25C, the positioning catheter 419 can be inserted through the apex of the heart (not shown) and translated along the tether 436. With the tether 436 pulled taut through the positioning catheter 419, the positioning catheter 419 can be moved into abutting contact with the valve 400 such that the positioning catheter 419 can be used to help move the valve 400 toward and/or into the retrieval assembly 402. Additionally, in some embodiments, the positioning catheter 419 can be used to aid in transitioning the outer frame 410 between the expanded or deployed configuration and the inverted configuration. For example, as shown in FIGS. 25B and 25C, the positioning catheter 419 can push the inner frame 440 and/or a central portion of the outer frame 410 into the outer catheter 403 to assist the outer frame 410 in transitioning (i.e., flipping) to the inverted position. Additionally, in some embodiments, the positioning catheter 419 can be pushed towards the valve 400 such that the positioning catheter 419 compresses or partially collapses a portion of the valve 400, such as, for example, the strut portion. The positioning catheter 419 can then assist in pushing the valve 400 toward and/or into the retrieval assembly 402 by assisting in providing the force required to transition the valve 400 to the inverted configuration. When the outer frame 410 is fully within the outer catheter 403, the positioning catheter 419 can be removed via the apex of the heart and the retrieval assembly 402 can be removed via the transfemoral trans-septal route.

In some embodiments, rather than removing the valve 400 from the heart with the retrieval assembly 402, the retrieval assembly 402 and/or the positioning catheter 419 can be used to reposition the valve 400 within the mitral valve annulus. For example, in some embodiments, the snare member 415 can be used to capture the inner frame 440 of the valve 400 and apply a compressive force to the inner frame 440 to reduce the diameter of the inner frame 440. The valve 400 can then be repositioned via movement of the snare member 415 and/or the positioning catheter 419. In some embodiments, the valve 400 can be partially or fully retracted into the outer catheter 403 and transitioned into the inverted configuration, as shown in FIG. 25C, and then redeployed to the desired location within the left atrium or left ventricle via pulling the tether 436 toward the apex of the heart and/or pushing the snare member 415 and/or the middle catheter 404 distally of the outer catheter 403 and into the left atrium or left ventricle. Upon redeploying from the outer catheter 403, the valve 400 can transition from the inverted configuration to the expanded configuration similarly as described above for the initial deployment of the valve 400.

Figure 26:
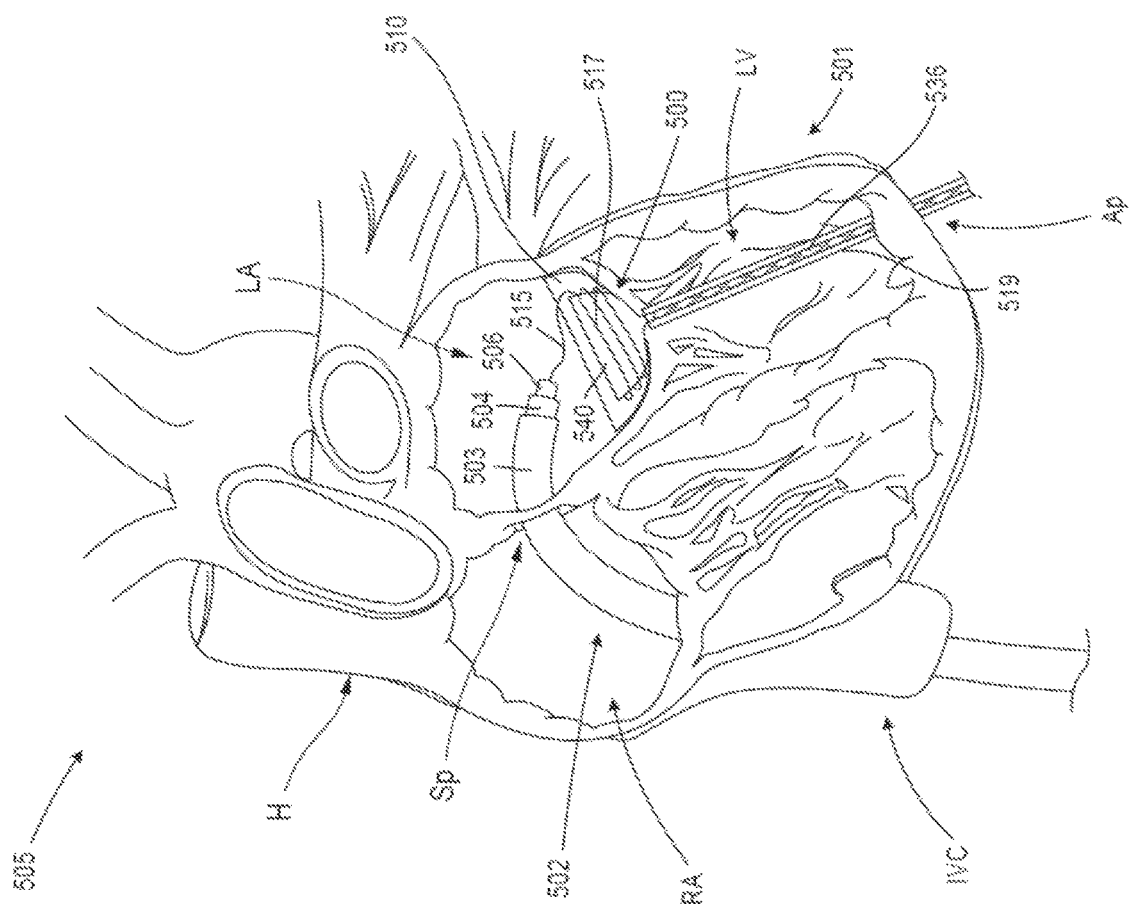
FIG. 26 is a cross-sectional illustration of a heart with a prosthetic mitral valve retrieval system engaged with a prosthetic mitral valve during a procedure to remove the prosthetic mitral valve from the heart, according to an embodiment.
Figure 27:
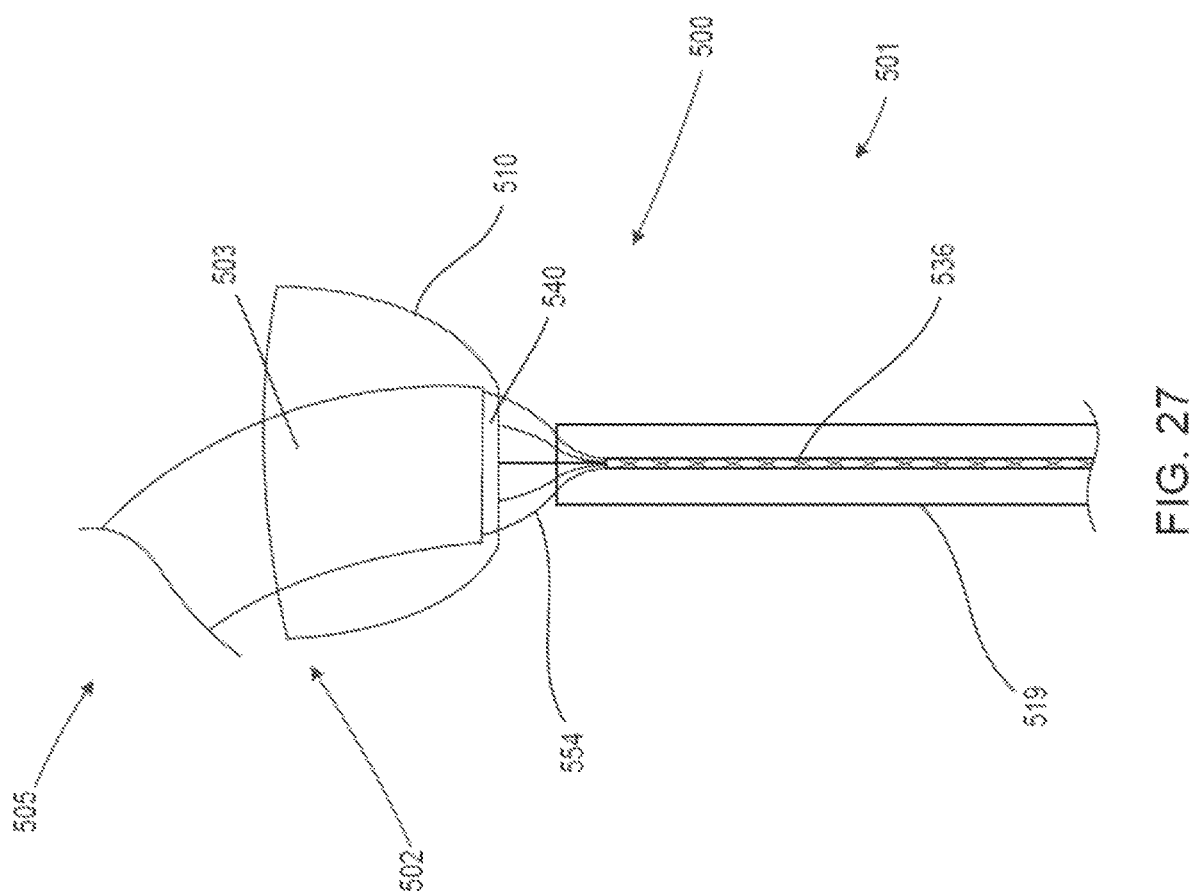
FIG. 27 is a cross-sectional illustration of the prosthetic mitral valve retrieval system of FIG. 26 during the procedure to remove the prosthetic mitral valve from the heart, with an inner frame of the prosthetic valve disposed partially within the retrieval system.
Figure 28:
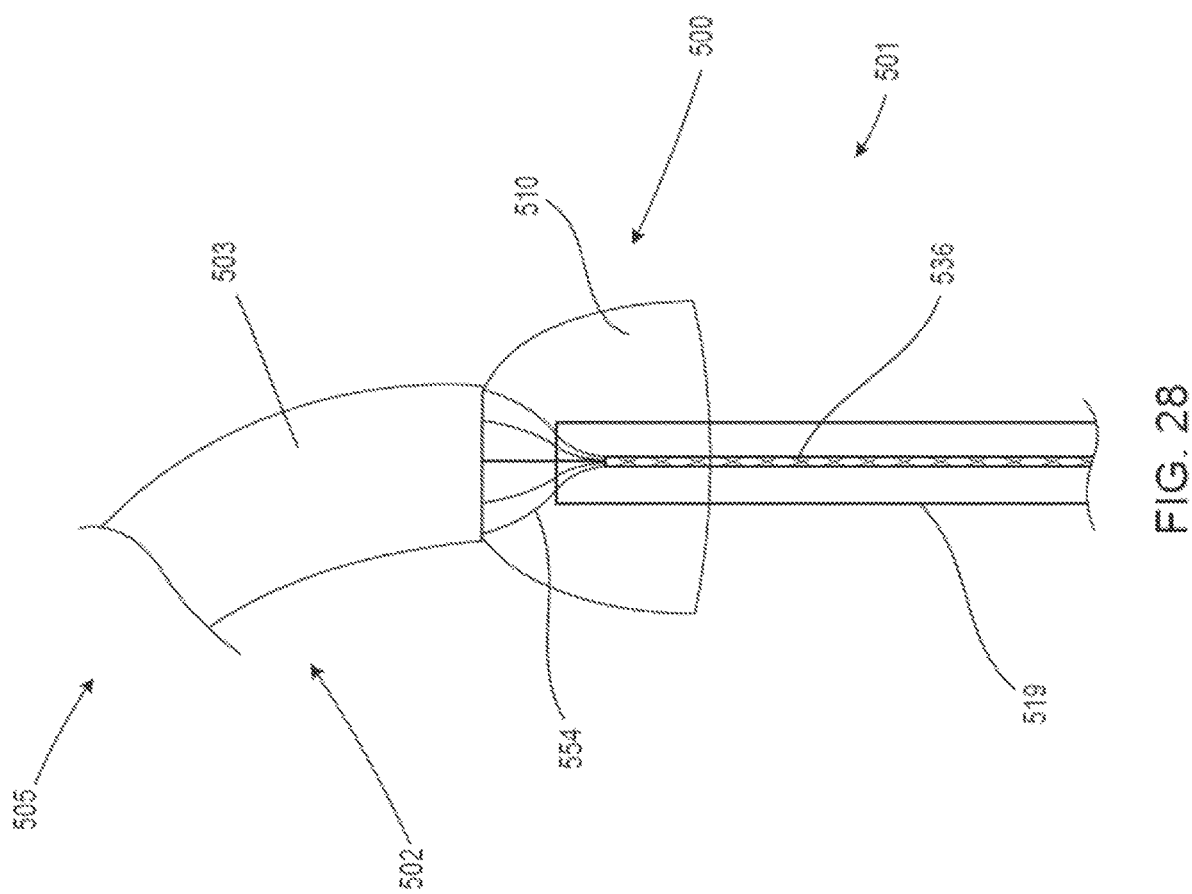
FIG. 28 is a cross-sectional illustration of the prosthetic mitral valve retrieval system of system of FIG. 26 during the procedure to remove the prosthetic mitral valve from the heart, with an outer frame of the prosthetic mitral valve moved to an inverted configuration relative to the inner frame.

FIGS. 26-28 are schematic illustrations of a prosthetic mitral valve retrieval system 505 during various stages of a procedure to engage, capture, and remove a prosthetic mitral valve 500 after it has been deployed within a heart H (shown in FIG. 26).

As shown in FIG. 26, the retrieval system 505 can include a retrieval assembly 502. The retrieval assembly 502 can include an outer catheter 503, a middle catheter 504, a snare catheter 506, and a snare member 515. The snare member 515 can be movably disposed within a lumen of the snare catheter 506 and the snare catheter 506 can be movably disposed within a lumen of the middle catheter 504. Similarly, the middle catheter 504 can be movably disposed within a lumen of the outer catheter 503. The outer catheter 503 can have a rigid distal tip. Optionally, in some embodiments, the retrieval system 505 can also include an apical positioning catheter 519.

The retrieval system 505 can engage with a valve assembly (e.g., a prosthetic heart valve) such that the retrieval system 505 can be used to control the position and configuration of the valve assembly. In particular, as shown in FIG. 26, the retrieval system 505 can engage with and retrieve a previously-implanted valve assembly 501 from, for example, a mitral annulus. The valve assembly 501 can include a valve 500 and a tether 536. The valve 500 and the tether 536 can be constructed the same as or similar to, and function the same as or similar to, any of the valves and tethers described herein and in the '305 PCT Application incorporated by reference above. For example, the valve 500 can include an inner frame 540 and an outer frame 510. Additionally, in some embodiments, the inner frame 540 can include a body portion and a tether connecting portion. The tether 536 can be coupled to the inner frame 540 via the tether connecting portion. A strut portion 554 (shown in FIG. 27) (also referred to herein as commissure posts 554) of the inner frame 540 can connect the tether connecting portion to the body portion. The outer frame 510 and the inner frame 540 can be formed with a shape-memory material. As a result, the outer frame 510 can be movably coupled to the inner frame 540 such that the valve 500 can be moved between a biased expanded or deployed configuration, an inverted configuration, and a collapsed or compressed configuration. The expanded configuration allows the valve assembly 501 to function when implanted within the heart H. The valve 500 can be moved to the inverted configuration and/or the compressed or collapsed configuration for delivery of the valve assembly 501 to, or retrieval of the valve assembly 501 from, the heart H of a patient.

More specifically, for delivery of the valve assembly 501 to the heart H via a delivery sheath and/or retrieval of the valve assembly 501 from the heart H via the retrieval assembly 502, the outer frame 510 can be moved to a prolapsed or inverted configuration relative to the inner frame 540 by folding or distally inverting the outer frame 510 via, for example, coupling joints. Prior to being inverted, the outer frame 510 can be in a first position relative to the inner frame 540 in which an open or free end portion is disposed in the same direction as a free end portion of the inner frame 540, as shown in FIGS. 26 and 27. When the outer frame 510 is moved to an inverted configuration, the free end portion of the outer frame 510 is disposed in an opposite direction as the free end portion of the inner frame 540, as shown in FIG. 28.

When in the inverted configuration, an overall length of the valve 500 is increased, but a length of the inner frame 540 and a length of the outer frame 510 remain the same (or substantially the same). In addition, in some instances, depending on the specific configuration of the outer frame 510, an overall outer perimeter or outer diameter of the valve 500 can be smaller when the valve 500 is in the inverted configuration. For example, with the valve 500 in the inverted configuration, the valve 500 can be placed within a lumen of a delivery sheath or the retrieval assembly 502 for delivery to or retrieval from, respectively, the left atrium LA of the heart H. Before inserting the valve 500 into a lumen of the delivery sheath or the retrieval assembly 502, the valve 500 can first be moved to the inverted configuration and then to a collapsed or compressed configuration within the lumen of the delivery sheath or retrieval assembly 502 in which the outer diameter or outer perimeter of the valve 500 is reduced. Because the valve 500 is in the inverted configuration, the valve 500 can be placed within a smaller delivery sheath or retrieval assembly 502 than would be possible if the valve 500 were merely collapsed radially. This is because when the valve 500 is in the biased expanded configuration, the inner frame 540 is nested within an interior of the outer frame 510, and thus the outer frame 510 must be collapsed around the inner frame 540 if merely collapsed radially. Whereas, in the inverted configuration, the inner frame 540 and the outer frame 510 are arranged axially with respect to each other (i.e., the inner frame is not nested within the outer frame 510), such that the outer frame 510 can be collapsed without needing to accommodate all of the structure of the inner frame 540 inside the outer frame 510. In other words, with the inner frame 540 disposed mostly inside or nested within the outer frame 510, the layers or bulk of the frame structures cannot be compressed to as small a diameter. In addition, the valve 500 is more flexible in the inverted configuration. In other words, less force is required to bend the valve 500 for the valve 500 to pass through tortuous vasculature or to make a tight turn (e.g., into the left atrium after passing through the atrial septum Sp to be properly oriented for insertion into the mitral valve annulus or, for retrieval, out of the mitral valve annulus to be properly oriented to pass through the atrial septum Sp). Conversely, if the outer frame 510 and the inner frame 540 are nested, the valve 500 is less flexible and more force is needed to bend the valve 500.

The snare member 515 can be any suitable shape and can include an engagement portion 517. The engagement portion 517 can be extendable from an undeployed configuration (not shown) when disposed within the lumen of the snare catheter 519 to a deployed configuration when disposed outside of the snare catheter 519. In some embodiments, the undeployed configuration of the engagement portion 517 can be a collapsed configuration where the engagement portion 517 is bent, squeezed, or otherwise reduced in diameter to fit into the lumen of the snare catheter 519. The engagement portion 517 can be formed with a shape-memory material and have a biased expanded or deployed configuration such that the engagement portion 517 automatically expands as it is moved out of the lumen of the snare catheter 519.

The engagement portion 517 of the snare member 515 is shaped and sized such that, in the expanded or deployed configuration, the engagement portion 517 can surround and engage with a portion of the inner frame 540 of the valve 500. As shown in FIG. 26, the engagement portion 517 or, alternatively, the entire snare member 515 can be shaped as a coil and sized such that, in the expanded or deployed configuration, the engagement portion 517 can surround the inner frame 540 and engage with the inner frame 540. In such an embodiment, the engagement portion 517 can be formed with a shape-memory material and the coil shape can be elongated in a delivery configuration inside the snare catheter 506. The coil shape can include multiple loops having the same or different diameters when expanded. As the engagement portion 517 is pushed or moved outside the distal end of the snare catheter 506, the portion of the engagement portion 517 outside of the distal end of the snare catheter 506 can transition to an expanded coil configuration. For example, in some embodiments, as a length of the engagement portion 517 is pushed outside of the distal end of the snare catheter 506, the diameter of the engagement portion 517 can enlarge such that the inner frame 540 can be received within the coil shape formed by the engagement portion 517. When the engagement portion 517 is a sufficient size to receive the inner frame 540, the coil can be moved further distally to surround the inner frame 540. Then, the snare catheter 506 can be moved distally relative to the snare member 515 such that the engagement portion 517 is partially withdrawn into a lumen of the snare member 515. As a result, the diameter of the engagement portion 517 can decrease, causing the engagement portion 517 to engage with and apply a compressive force to the inner frame 540, as shown in FIG. 26. Thus, the snare member 515 can be used to control the position and/or diameter of the inner frame 540.

As shown in FIG. 27, the inner frame 540 of the valve 500 can be retracted into the outer catheter 503 via a proximal movement of the snare member 515 while the engagement portion 517 applies a compressive force to the inner frame 540. The snare member 515 can be pulled further proximally such that the outer frame 510 is pulled into abutting contact with the rigid distal tip of the distal end of the outer catheter 503, as shown in FIG. 27. As the snare member 515 pulls the inner frame 540 further proximally relative to the outer catheter 503, the outer frame 510 can be moved (i.e., flipped) into the inverted configuration as a result of the force applied by the rigid distal tip of the outer catheter 503 against the outer frame 510, as shown in FIG. 28. The snare member 515 can continue to be retracted until the outer frame 510 is fully within the outer catheter 503.

In some embodiments, the apical positioning catheter 519 (also referred to herein as "the positioning catheter 519") can be used to position and/or orient the valve assembly 501 for repositioning and/or retrieval of the valve assembly 501. The positioning catheter 519 can be inserted through the apex Ap of the heart H and translated along the tether 536 (i.e., the tether 536 can be threaded through a lumen of the positioning catheter 519). The positioning catheter 519 can be pushed into abutting contact with the valve 500 such that a portion of the valve is disposed within a lumen of the positioning catheter 519. The positioning catheter 519 can then be used to help move the valve 500 toward the retrieval assembly 502 or reposition the valve 500. In some embodiments, the positioning catheter 519 can engage with the valve 500 such that the positioning catheter 519 can control the movement of the valve 500 in some or all directions (e.g., distal, proximal, rotational, and/or lateral movement). For example, in some embodiments, the positioning catheter 519 can be moved towards the valve 500 along the tether 536 while the tether 536 is simultaneously pulled taut away from the valve 500 such that the valve 500 is positioned in abutting contact with the distal end of the positioning catheter 519. With the tether 536 continuing to be held taut, the positioning catheter 519 can then be used to control the position of the valve 500. In some embodiments, the positioning catheter 519 can be used to aid in transitioning the outer frame 510 between the unbiased, expanded configuration and the inverted configuration. For example, in some embodiments, the positioning catheter 519 can be pushed towards the valve 500 along the tether 536 while the tether 536 is simultaneously pulled taut away from the valve 500 such that the distal end of the positioning catheter 519 can compress or partially collapse a portion of the valve 500, such as, for example, the strut portion 554. The positioning catheter 519 can then assist in pushing the valve 500 toward and/or into the retrieval assembly 502, assisting in providing the force required to transition the valve 500 to the inverted configuration.

In use, the valve assembly 501 can be delivered to a heart H as described above and in the '305 PCT Application. For example, the valve assembly 501 can be placed in the distal end of a delivery sheath in the inverted configuration and the delivery sheath can be introduced through a femoral vein puncture and extended through the femoral vein, through the inferior vena cava IFC, into the right atrium RA, through a trans-septal puncture of the septum of the heart Sp, and into the left atrium LA or left ventricle LV of the heart H. With the distal end portion of the delivery sheath disposed within the left atrium LA or left ventricle LV of the heart H, the valve 500 can be deployed outside a distal end of the delivery sheath. For example, in some embodiments, a pusher device can be used to move or push the valve 500 out of the distal end of the delivery sheath. In some embodiments, the tether 536 can extend through the mitral annulus, through the left ventricle LV, and out of a puncture site at the apex Ap of the heart H. In such embodiments, the valve 500 can be moved out of the delivery sheath by pulling proximally on the tether 536. In some embodiments, the valve 500 can be deployed by pushing with the pusher device and pulling the tether 536. As the valve 500 exits the lumen of the delivery sheath, the outer frame 510 exits first in the inverted configuration. After the outer frame 510 is fully outside of the lumen of the delivery sheath, the outer frame 510 can revert to its expanded or deployed configuration. In some embodiments, the outer frame 510 can revert automatically after fully exiting the lumen of the delivery sheath due to its shape-memory properties. In some embodiments, a component of the delivery sheath or another device can be used to aid in the reversion of the outer frame 510. In some embodiments, the pusher device and/or the tether 536 can be used to aid in reversion of the outer frame 510. The valve 500 can continue to be deployed until the inner frame 540 is fully deployed within the left atrium and the valve 500 is in the expanded or deployed configuration. The valve 500 can then be securely implanted in the mitral annulus. Additionally, the tether 536 of the valve assembly 501 can then be secured to the apex Ap of the heart H with an epicardial pad device, similarly as shown and described with reference to FIG. 24. The delivery sheath and any other delivery instruments can then be removed.

With the valve assembly 501 in the deployed configuration within the mitral annulus, the retrieval system 505 can be used to reposition and/or retrieve the valve assembly 501. In some embodiments, the retrieval assembly 502 can approach the left atrium of the heart transfemorally along the transfemoral trans-septal route (i.e., the same path described above for the delivery of the valve assembly 501). In other words, the outer catheter 503, middle catheter 504, and snare catheter 506 of the retrieval assembly 502 can be introduced through a femoral vein puncture and extended through the femoral vein, through the inferior vena cava IVC, into the right atrium RA, through a trans-septal puncture of the septum Sp of the heart H, and into the left atrium LA of the heart H. In other embodiments, the retrieval assembly 502 can approach the valve assembly 501 transatrially, transjugularly, or along any other suitable path. Additionally, in embodiments in which the tether 536 has been secured to the apex Ap of the heart H via an epicardial pad device, the tether 536 can be separated from the epicardial pad device through any suitable means.

As described above, the valve 500 can be transitioned to the inverted configuration before being moved into the retrieval assembly 502 so that the valve 500 can fit within a smaller diameter retrieval assembly 502 and so that the retrieval assembly 502 and valve 500 can bend more easily when being maneuvered through the body. To transition the valve 500 to the inverted configuration, once the distal end of the retrieval assembly 502 is within the left atrium of the heart, the snare member 515 can be extended outside of the distal end of the snare catheter 506. As the snare member 515 is pushed out of the distal end of the snare catheter 506, the engagement portion 517 of the snare member 515 can transition from the undeployed configuration to the deployed configuration. With the engagement portion 517 in the deployed configuration, the snare member 515 can be moved toward the valve 500 such that the engagement portion 517 surrounds the inner frame 540, as shown in FIG. 2. The engagement portion 517 can then be manipulated such that the engagement portion 517 grasps the inner frame 540 (e.g., the engagement portion 517 can be reduced in diameter to securely engage with the inner frame 540). When the engagement portion 517 is securely engaged with the inner frame 540, the engagement portion 517 can be further manipulated to apply a compressive force to reduce the diameter of the inner frame 540 to a diameter sufficiently small to fit within the middle catheter 504.

While compressing the inner frame 540, the snare member 515 can be retracted proximally relative to the snare catheter 506 and/or the snare catheter 506 can be retracted proximally relative to the middle catheter 504. As a result, at least a portion of the inner frame 540 can be pulled into a lumen of the middle catheter 504, as shown in FIG. 27. The snare member 515, snare catheter 506, and middle catheter 504 can then be pulled proximally relative to the outer catheter 503 such that the outer frame 510 transitions to the inverted configuration, as shown in FIG. 28. More specifically, the proximal movement of the inner frame 540 can cause the outer frame 510 to be pulled against the rigid tip of the distal end of the outer catheter 503. As the inner frame 540 is pulled further proximally, the rigid tip of the outer catheter 503 can force the outer frame 510 to flip into the inverted configuration. The snare member 515, snare catheter 506, and middle catheter 504 can then continue to be retracted until the outer frame 510 is fully within the outer catheter 503.

Optionally, the positioning catheter 519 can be used to aid in positioning and orienting the valve assembly 501 for repositioning and/or retrieval. In such embodiments, as shown in FIG. 26, the positioning catheter 519 can be inserted through the apex Ap of the heart H and translated along the tether 536. With the tether 536 pulled taut through the positioning catheter 519, the positioning catheter 519 can be moved into abutting contact with the valve 500 such that the positioning catheter 519 can be used to help move the valve 500 toward and/or into the retrieval assembly 502. Additionally, in some embodiments, the positioning catheter 519 can be used to aid in transitioning the outer frame 510 between the expanded or deployed configuration and the inverted configuration. For example, as shown in FIGS. 27 and 28, the positioning catheter 519 can push the inner frame 540 and/or a central portion of the outer frame 510 into the outer catheter 503 to assist the outer frame 510 in transitioning (i.e., flipping) to the inverted position. Additionally, in some embodiments, the positioning catheter 519 can be pushed towards the valve 500 such that the positioning catheter 519 compresses or partially collapses a portion of the valve 500, such as, for example, the strut portion 554. The positioning catheter 519 can then assist in pushing the valve 500 toward and/or into the retrieval assembly 502 by assisting in providing the force required to transition the valve 500 to the inverted configuration. When the outer frame 510 is fully within the outer catheter 503, the positioning catheter 519 can be removed via the apex Ap of the heart H and the retrieval assembly 502 can be removed via the transfemoral trans-septal route.

In some embodiments, rather than removing the valve 500 from the heart H with the retrieval assembly 502, the retrieval assembly 502 and/or the positioning catheter 519 can be used to reposition the valve 500 within the mitral valve annulus. For example, in some embodiments, the snare member 515 can be used to capture the inner frame 540 of the valve 500 and apply a compressive force to the inner frame 540 to reduce the diameter of the inner frame 540. The valve 500 can then be repositioned via movement of the snare member 515 and/or the positioning catheter 519. In some embodiments, the valve 500 can be partially or fully retracted into the outer catheter 503 and transitioned into the inverted configuration, as shown in FIG. 28, and then redeployed to the desired location within the left atrium LA or left ventricle LV via pulling the tether 536 toward the apex Ap of the heart H and/or pushing the snare member 515 and/or the middle catheter 504 distally of the outer catheter 503 and into the left atrium LA or left ventricle LV. Upon redeploying from the outer catheter 503, the valve 500 can transition from the inverted configuration to the expanded configuration similarly as described above for the initial deployment of the valve 500.

Figure 29:
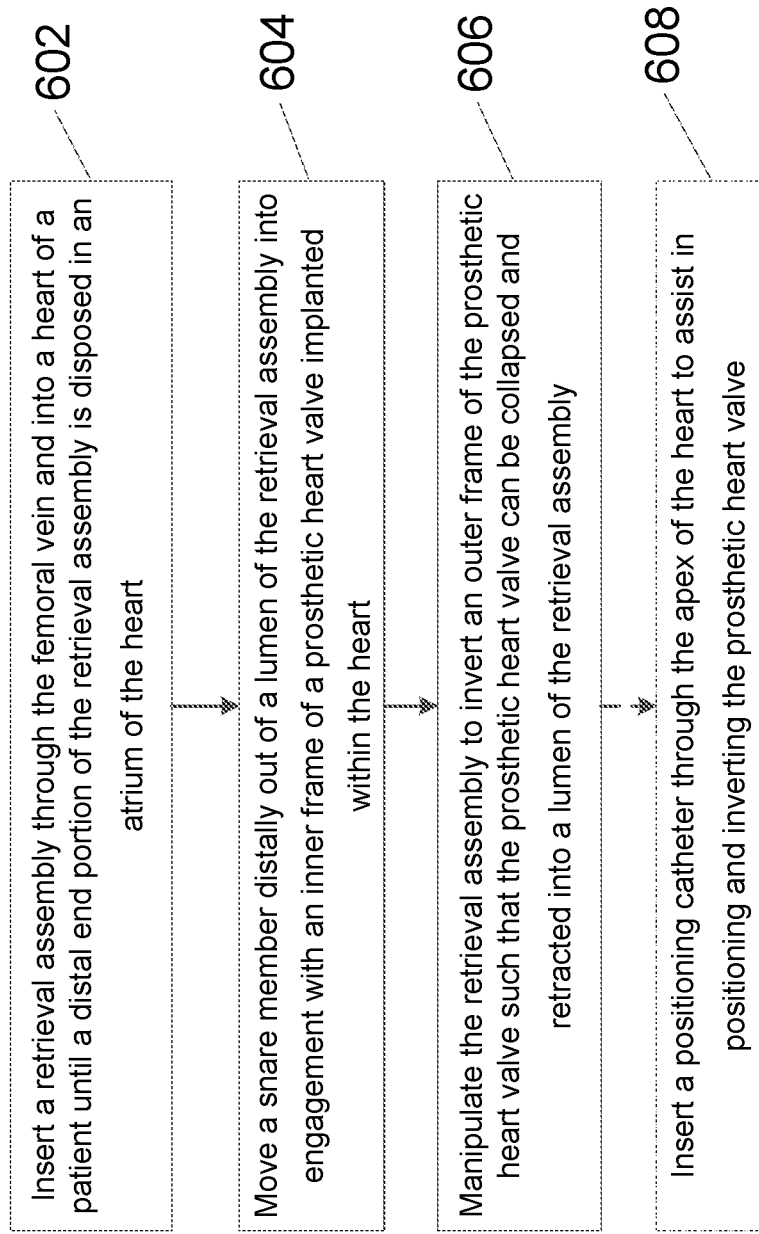
FIG. 29 is a flowchart illustrating a method of retrieving an implanted prosthetic heart valve, according to an embodiment.

FIG. 29 is a flowchart illustrating a method of retrieving an implanted prosthetic mitral heart valve, according to an embodiment. The method includes at 602, inserting a retrieval assembly through the femoral vein and into a heart of a patient until a distal end portion of the retrieval assembly is disposed in an atrium of the heart. The prosthetic heart valve can be formed with a shape-memory material. In some embodiments, the prosthetic heart valve is a prosthetic mitral valve and the inserting includes inserting the retrieval assembly through a septum of the heart and into a left atrium of the heart. The retrieval assembly can include an outer catheter, a middle catheter, a snare catheter, and a snare member. The snare member can be moved distally out of a lumen of the retrieval assembly into engagement with an inner frame of the prosthetic heart valve, at 604. For example, the snare member can be moved distally out of a lumen of the snare catheter. At 606, the retrieval assembly can be manipulated to invert an outer frame of the prosthetic mitral valve such that the prosthetic heart valve can be collapsed and retracted into a lumen of the retrieval assembly. In some embodiments, a positioning catheter can be inserted through the apex of the heart and moved into engagement with a portion of the prosthetic heart valve (e.g., a portion extending into a ventricle or closest to the ventricle of the heart) to assist in positioning and inverting the prosthetic valve, at 608.

Although the specific embodiments described herein refer to devices and methods for retrieving and repositioning a prosthetic mitral valve, the devices and methods can also be used to retrieve and reposition other prosthetic heart valves, such as, for example, tricuspid heart valves.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or features of the different embodiments described.

What is claimed is:

1. A method, comprising:
   inserting a retrieval assembly through a femoral vein and into a heart of a patient until a distal end portion of the retrieval assembly is disposed in an atrium of the heart, the retrieval assembly including a snare member;
   moving the snare member distally out of a lumen of the retrieval assembly and into engagement with an inner frame of a prosthetic heart valve implanted within the heart;
   manipulating the retrieval assembly to invert an outer frame of the prosthetic heart valve such that the prosthetic heart valve is collapsed and at least a portion of the prosthetic heart valve is retracted into a lumen of the retrieval assembly.

2. The method of claim 1, further comprising:
   inserting a positioning catheter through an apex of the heart and engaging the distal end of the positioning catheter with the prosthetic heart valve to assist in inverting the prosthetic heart valve with the retrieval assembly.

3. The method of claim 1, further comprising:
   after the manipulating, withdrawing the retrieval assembly back through the femoral vein with the prosthetic heart valve disposed in a collapsed configuration within the lumen of the retrieval assembly.

4. The method of claim 1, wherein the prosthetic heart valve is a prosthetic mitral valve, the inserting the retrieval assembly through a femoral vein and into the heart includes inserting the retrieval assembly through a femoral vein, into the heart of the patient, and through a septum of the heart until a distal end portion of the retrieval assembly is disposed in a left atrium of the heart.

5. The method of claim 1, wherein the prosthetic heart valve is a prosthetic tricuspid valve, the inserting the retrieval assembly through a femoral vein and into the heart includes inserting the retrieval assembly through a femoral vein and into the heart of the patient until a distal end portion of the retrieval assembly is disposed in a right atrium of the heart.

6. The method of claim 1, wherein the prosthetic heart valve is a prosthetic mitral valve, the method further comprising:
   after the manipulating, repositioning the prosthetic mitral valve within a native mitral annulus of the heart;
   releasing the prosthetic mitral valve from the retrieval assembly; and
   withdrawing the retrieval assembly back through the femoral vein.

7. The method of claim 1, wherein the prosthetic heart valve is a prosthetic mitral valve, the method further comprising:
   during the manipulating, the prosthetic mitral valve is dislodged from a native mitral annulus of the heart.

8. The method of claim 1, wherein the retrieval assembly further includes an outer catheter, a middle catheter movably disposable within a lumen of the outer catheter and a snare catheter, the snare member being movably disposable within the lumen of the snare catheter,
   the moving the snare member distally out of the lumen of the retrieval assembly includes moving the snare member distally out of the lumen of the snare catheter.

9. The method of claim 8, wherein the manipulating the retrieval assembly to invert an outer frame of the prosthetic heart valve further includes retracting at least a portion of the prosthetic heart valve into the lumen of the outer catheter.

10. The method of claim 1, wherein the retrieval assembly further includes an outer catheter, a middle catheter movably disposable within a lumen of the outer catheter and a snare catheter, the snare member being movably disposable within the lumen of the snare catheter,
    the manipulating the retrieval assembly to invert an outer frame of the prosthetic heart valve includes moving the snare member distally within the lumen of the snare catheter such that the at least a portion of the prosthetic heart valve is retracted into the lumen of the middle catheter.

11. A method, comprising:
    advancing a snare member out of a lumen of a catheter and into engagement with an inner frame of a prosthetic heart valve;
    manipulating the snare member such that at least a portion of the inner frame of the prosthetic heart valve is retracted into the lumen of the catheter;

withdrawing the snare member proximally within the lumen of the catheter such that an outer frame of the prosthetic heart valve is pulled into abutting contact with a distal tip of the catheter; and inverting the outer frame of the prosthetic heart valve relative to the inner frame of the prosthetic heart valve by moving the inner frame proximally relative to the distal tip of the catheter and within the lumen of the catheter.

12. The method of claim 11, further comprising:
withdrawing the snare member further proximally such that the prosthetic heart valve is in a collapsed configuration within the lumen of the catheter.

13. The method of claim 11, wherein the catheter is an outer catheter and, during the manipulating of the snare member, the inner frame of the prosthetic heart valve is retracted into a middle catheter movably disposed within the outer catheter.

14. The method of claim 11, wherein the inverting includes pushing the catheter distally relative to the prosthetic heart valve.

15. The method of claim 11, wherein the snare member includes an engagement portion, the manipulating of the snare member includes applying a compressive force to the inner frame with the engagement portion of the snare member such that the inner frame of the prosthetic heart valve is moved to a collapsed configuration.

16. The method of claim 11, wherein the inverting includes pushing the prosthetic mitral valve proximally and further into the lumen of the catheter with a positioning catheter.

* * * * *